(12) United States Patent
Hasumi et al.

(10) Patent No.: US 8,110,596 B2
(45) Date of Patent: Feb. 7, 2012

(54) TRIPRENYL PHENOL COMPOUND, PROCESS FOR PRODUCTION OF TRIPRENYL PHENOL COMPOUND, AND THROMBOLYSIS ENHANCER

(75) Inventors: Keiji Hasumi, Inagi (JP); Yoshikazu Kitano, Fuchu (JP); Hideo Ohishi, Sayama (JP); Haruki Koide, Hachioji (JP); Keiko Hasegawa, Zama (JP); Ritsuko Narasaki, Fuchu (JP)

(73) Assignee: Tokyo University of Agriculture and Technology TLO Co., Ltd., Tokyo (JP)

( * ) Notice: Subject to any disclaimer, the term of this patent is extended or adjusted under 35 U.S.C. 154(b) by 91 days.

(21) Appl. No.: 11/991,406

(22) PCT Filed: Mar. 20, 2007

(86) PCT No.: PCT/JP2007/055749
§ 371 (c)(1),
(2), (4) Date: Jan. 29, 2009

(87) PCT Pub. No.: WO2007/111203
PCT Pub. Date: Oct. 4, 2007

(65) Prior Publication Data
US 2009/0216028 A1 Aug. 27, 2009

(30) Foreign Application Priority Data

Mar. 27, 2006 (JP) .................. 2006-086434
Nov. 30, 2006 (JP) .................. 2006-324870

(51) Int. Cl.
*A61K 31/407* (2006.01)
*C07D 491/052* (2006.01)

(52) U.S. Cl. ...................... 514/411; 548/431

(58) Field of Classification Search .............. None
See application file for complete search history.

(56) References Cited

FOREIGN PATENT DOCUMENTS

| JP | A 2002-065288 | 3/2002 |
| JP | A 2004-224737 | 8/2004 |
| JP | A 2004-224738 | 8/2004 |
| WO | WO 98/56940 A1 | 12/1998 |

OTHER PUBLICATIONS

Xu et al. J. org. Chem. vol. 57, pp. 6700-6703 (1992).*
Xu, Xuemin et al., "Stachybotrins A and B: Novel Bioactive Metabolites from a Brackish Water Isolate of the Fungus *Stachybotrys* sp.," J. Org. Chem, vol. 57, pp. 6700-6703 (1992).
Takayasu, Ritsuko et al., "Enhancement of Fibrin Binding and Activation of Plasminogen by Staplabin through Induction of a Conformational Change in Plasminogen," FEBS Letters, vol. 418, p. 58-62 (1997).
Inoue, Seiichi et al., "Synthesis of Tricyclic Pyrano[2,3-e]isoindolin-3-ones as the Core Structure of Stachybotrin A, B, and C," Chem. Commun., No. 18, p. 1974-1976 (2006).

Shinohara, Chikara et al., "Staplabin, a Novel Fungal Triprenyl Phenol which Stimulates the Binding of Plasminogen to Fibrin and U937 Cells," The Journal of Antibiotics, vol. 49, p. 961-966 (1996).
Kohyama, Tomoo et al., "SMTP-1 and -2, Novel Analogs of Staplabin Produced by *Stachybotrys microspora* IFO 30018," The Journal of Antibiotics, vol. 50, No. 2, p. 172-174 (Feb. 1997).
Hasumi, Keiji et al., "Isolation of SMTP-3, 4, 5 and -6, Novel Analogs of Staplabin, and Their Effects on Plasminogen Activation and Fibrinolysis," The Journal of Antibiotics, vol. 51, No. 12, p. 1059-1068 (Dec. 1998).

(Continued)

*Primary Examiner* — Rebecca Anderson
*Assistant Examiner* — Alicia L Otton
(74) *Attorney, Agent, or Firm* — Oliff & Berridge, PLC

(57) ABSTRACT

The present invention provides a triprenyl phenol compound represented by the following formula (II) and (III) and having a thrombolysis-enhancing activity, and an efficient method for producing the triprenyl phenol compound. In formula (II) and (III), $R^1$ represents an aromatic group having as a substituent or as a part of a substituent at least one member selected from the group consisting of a carboxyl group, a hydroxyl group, a sulfonic acid group and a secondary amino group, or an aromatic group which comprises a secondary amino group and may comprise nitrogen; $R^4$ in the general formula (III) represents an aromatic amino acid residue represented by the general formula (III-1) below; X represents —CHY—$(CH_3)_2Z$; and Y and Z are respectively —H or —OH or together form a single bond: (III-1) wherein $R^5$ represents a hydroxyl group which may be present or absent; and n represents an integer of 0 or 1.

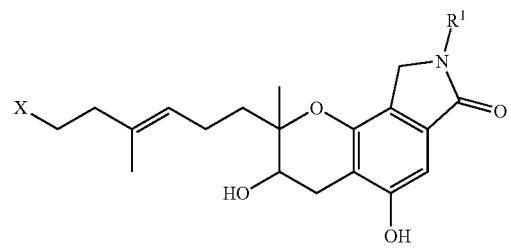

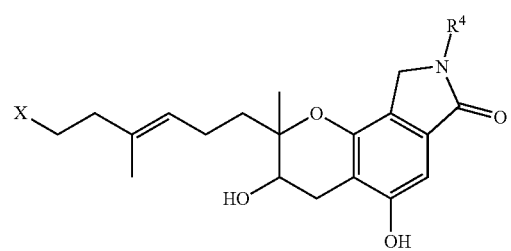

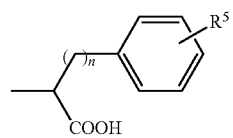

7 Claims, 4 Drawing Sheets

OTHER PUBLICATIONS

Hu, Weimin et al., "Activation of Fibrinolysis by SMTP-7 and -8, Novel Staplabin Analogs with a Pseudosymmetric Structure," The Journal of Antibiotics, vol. 53, No. 3, p. 241-247 (Mar. 2000).

Hu, Weimin et al., "Selective Production of Staplabin and SMTPs in Cultures of *Stachybotrys microspora* Fed with Precursor Amines," The Journal of Antibiotics, vol. 54, No. 11, p. 962-966 (Nov. 2001).

Hu, Weimin et al., "SMTP -4D, -5D, -6D, -7D and -8D, a New Series of the Non-lysine-analog Plasminogen Modulators with a D-Amino Acid Moiety," The Journal of Antibiotics, vol. 56, No. 10, p. 832-837 (Oct. 2003).

Ohyama, Shigeki et al., "Nonlysine-analog Plasminogen Modulators Promote Autoproteolytic Generation of Plasmin(ogen) Fragments with Angiostatin-like Activity," Eur. J. Biochem. vol. 271, p. 809-820 (2004).

Yuriko Nozawa et al., "Stachybotrin C and Parvisporin, Novel Neuritogenic Compounds. I. Taxonomy, Isolation, Physico-chemical and Biological Properties," Journal of Antibiotics, vol. 50, No. 8, 1997, pp. 635-640, XP002661234.

Oct. 27, 2011 Supplementary European Search Report issued in European Application No. EP 07 73 9192.8.

\* cited by examiner

TRIPRENYL PHENOL COMPOUND, PROCESS FOR PRODUCTION OF TRIPRENYL PHENOL COMPOUND, AND THROMBOLYSIS ENHANCER

TECHNICAL FIELD

The present invention relates to a triprenyl phenol compound, a process for production of a triprenyl phenol compound, and a thrombolysis enhancer.

BACKGROUND ART

Among microbiotic metabolites having a triprenyl phenol skeleton, there are species having important physiological activities. For example, specific triprenyl phenol compounds obtained from filamentous fungi are known to have physiologically active effects on phenomena that are important to the living body, such as a thrombolysis enhancing action or an angiogenesis suppressive action (Patent Documents 1 to 3).

Furthermore, as another triprenyl phenol compound differing from the above-mentioned triprenyl phenol compounds in stereostructure, Patent Document 4 discloses a triprenyl phenol compound having hair growth activity. Non-Patent Document 1 also discloses a triprenyl phenol compound having antibacterial activity and antifungal activity.

It has been suggested that triprenyl phenol compounds obtained from cultures using filamentous fungi induce changes in the conformation of plasminogen (Plg), and as a result, increase sensitivity to activation by plasminogen activators (PA) and the ability of plasminogen to bind fibrin, thus enhancing thrombolysis (Non-patent Document 2). A compound having two triprenyl phenol skeletons, which is obtained by adding ornithine as the amino acid (hereinafter, referred to as orniplabin), is, in particular, known to have a significantly strong thrombolysis enhancing action (Patent document 2).

In this way, since compounds having a triprenyl phenol skeleton exhibit a variety of activities in accordance with their stereostructure or substituents, the compounds are extremely useful.

These triprenyl phenol compounds having various activity types have complicated structures, and thus there is demand for a method to obtain the compounds more efficiently. As such a production method, methods for producing the compounds by culturing microorganisms are being developed. However, in methods using microorganisms, typically, the compounds are produced together with numerous analogs and, therefore, various measures are being implemented so as to obtain the compounds efficiently in large amounts. In particular, in order to produce active triprenyl phenol compounds having physiological activities such as a thrombolysis enhancing action or an angiogenesis inhibitory action, Patent Documents 1 to 3 disclose a culture system to which an amino acid or amino alcohol corresponding to the substituent is added during the early phase of the culture of filamentous fungi, such as immediately after the initiation of culture.

Patent Document 1: Japanese Patent Application Laid-Open (JP-A) No. 2002-65288

Patent Document 2: JP-A No. 2004-22473.7

Patent Document 3: JP-A No. 2004-224738

Patent Document 4: International Patent Publication WO 98/56940

Non-Patent Document 1: J. Org. Chem., (1992), Vol. 57, pp. 6700-6703

Non-Patent Document 2: FEBS Letter, (1997), Vol. 418, pp. 58-62

DISCLOSURE OF THE INVENTION

Problems to be Solved by the Invention

However, since orniplabin is a dimer having a molecular weight of greater than 800, it is believed to be disadvantageous from the viewpoint of absorption to the living body.

Furthermore, in conventional culture methods using filamentous fungi, the type of the product obtained in accordance with type of the amino acid and amino alcohol that can be added, is limited. The amount of generation also cannot be said to be sufficient. Further, since active triprenyl phenol compounds have a complicated structure, chemical synthesis of the entire process is very inefficient.

Therefore, it is an object of the invention to provide a novel triprenyl phenol compound which can exhibit a high thrombolysis enhancing action even at low molecular weight, and to provide a thrombolysis enhancer containing the same.

It is another object of the invention to efficiently produce an active triprenyl phenol compound having high physiological activity.

Means for Solving the Problems

A first triprenyl phenol compound of the invention is a triprenyl phenol compound which is represented by the following formula (I), and has a negative optical rotation. In the following formula (I), X is —CHY—(CH$_3$)$_2$Z; Y and Z are respectively —H or —OH, or together form a single bond.

The first triprenyl phenol compound is preferably a compound represented by the following formula (I-A).

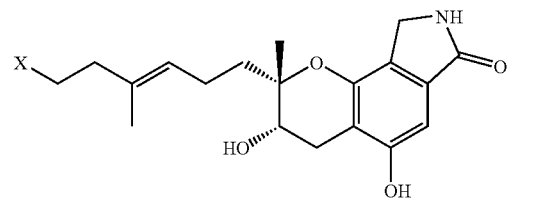

(I)

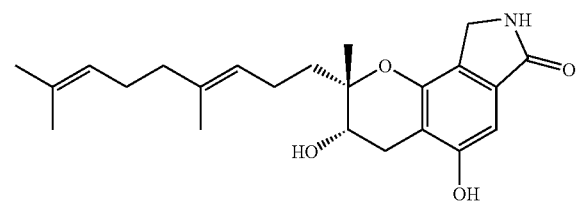

(I-A)

A second triprenyl phenol compound of the invention is a triprenyl phenol compound represented by the following formula (II). In the following formula (II), R$^1$ represents an aromatic group having as a substituent or as a part of a substituent at least one group selected from the group consisting of a carboxyl group, a hydroxyl group, a sulfonic acid group and a secondary amino group, or an aromatic group which contains a secondary amino group, and may contain nitrogen; X is —CHY—(CH$_3$)$_2$Z; and Y and Z are respectively —H or —OH, or together form a single bond.

(II)

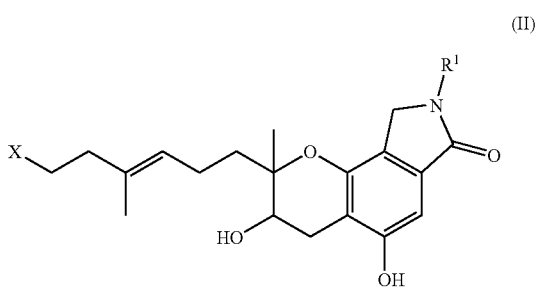

A third triprenyl phenol compound of the invention is a triprenyl phenol compound represented by the following formula (III). In the following formula (III), $R^4$ represents an aromatic amino acid residue represented by the following formula (III-1), while in the following formula (III-1), $R^5$ represents a hydroxyl group which may be present or absent; n represents an integer of 0 or 1; X is —CHY—(CH$_3$)$_2$Z; and Y and Z are respectively —H or —OH, or together form a single bond.

(III)
(III-1)

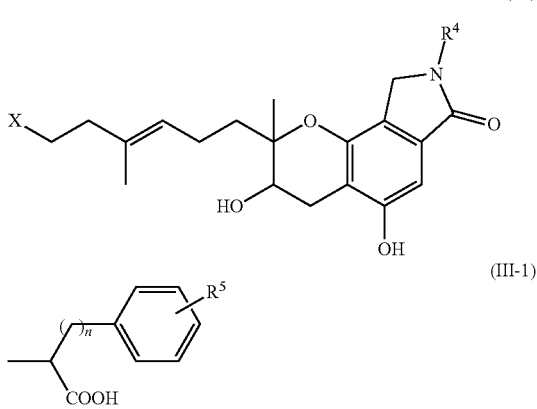

The thrombolysis enhancer of the invention is a thrombolysis enhancer containing the triprenyl phenol compound represented by the formula (II) or (III) as an active ingredient.

A method for producing the second triprenyl phenol compound of the invention includes culturing a filamentous fungus in a culture solution containing an additive amine compound selected from the group consisting of aminophenol, aminobenzoic acid, adenine, adenosine, aminodihydrophthalazinedione, aminonaphtholsulfonic acid, sulfanilic acid and derivatives thereof, and separating the present triprenyl phenol compound from the culture after the culturing.

A method for producing the third triprenyl phenol compound of the invention includes culturing a filamentous fungus in a culture solution containing an additive amine compound selected from the group consisting of aromatic amino acids and derivatives thereof, and separating the subject triprenyl phenol compound from the culture after the culturing.

The second and third triprenyl phenol compounds of the invention may also be produced according to the production method described above, wherein the culturing of a filamentous fungus includes a first culturing process using a restricted medium having a content of amine compound of 0.5% by mass or less, and a second culturing process using a production medium containing an additive amine compound, which process commences at an intermediate stage of culture.

The method for producing a triprenyl phenol compound of the invention includes culturing a filamentous fungus in a first culturing process using a restricted medium in which at least one of the type and the amount of amine compound is restricted, culturing the filamentous fungus in a second culturing process using a production medium containing an amine compound, which process commences at an intermediate stage of culture, and obtaining a triprenyl phenol compound from the culture obtained after the second culturing process.

The restricted medium used in the first culturing process may contain 0.5% by mass or less of an amine compound, and the production medium may contain an organic amine compound.

Furthermore, the first triprenyl phenol compound of the invention is preferably produced according to the present production method, wherein the restricted medium used in the first culturing process contains 0.5% by mass or less of an organic amine compound and the production medium used in the second culturing process contains an inorganic primary amine compound.

In any of the production methods of the invention, the restricted medium and the production medium may further contain metal ions of at least one species selected from the group consisting of magnesium, cobalt, iron and calcium.

Furthermore, in any of the production methods of the invention, the filamentous fungus may be *Stachybotrys microspora* IFO30018.

Effects of the Invention

According to the invention, a novel triprenyl phenol compound which can exhibit a high thrombolysis enhancing action even at low molecular weight can be provided, and a thrombolysis enhancer containing the compound can be provided.

According to the invention, an active triprenyl phenol compound having high physiological activity can be efficiently produced.

BEST MODE FOR CARRYING OUT THE INVENTION

Figure 1:
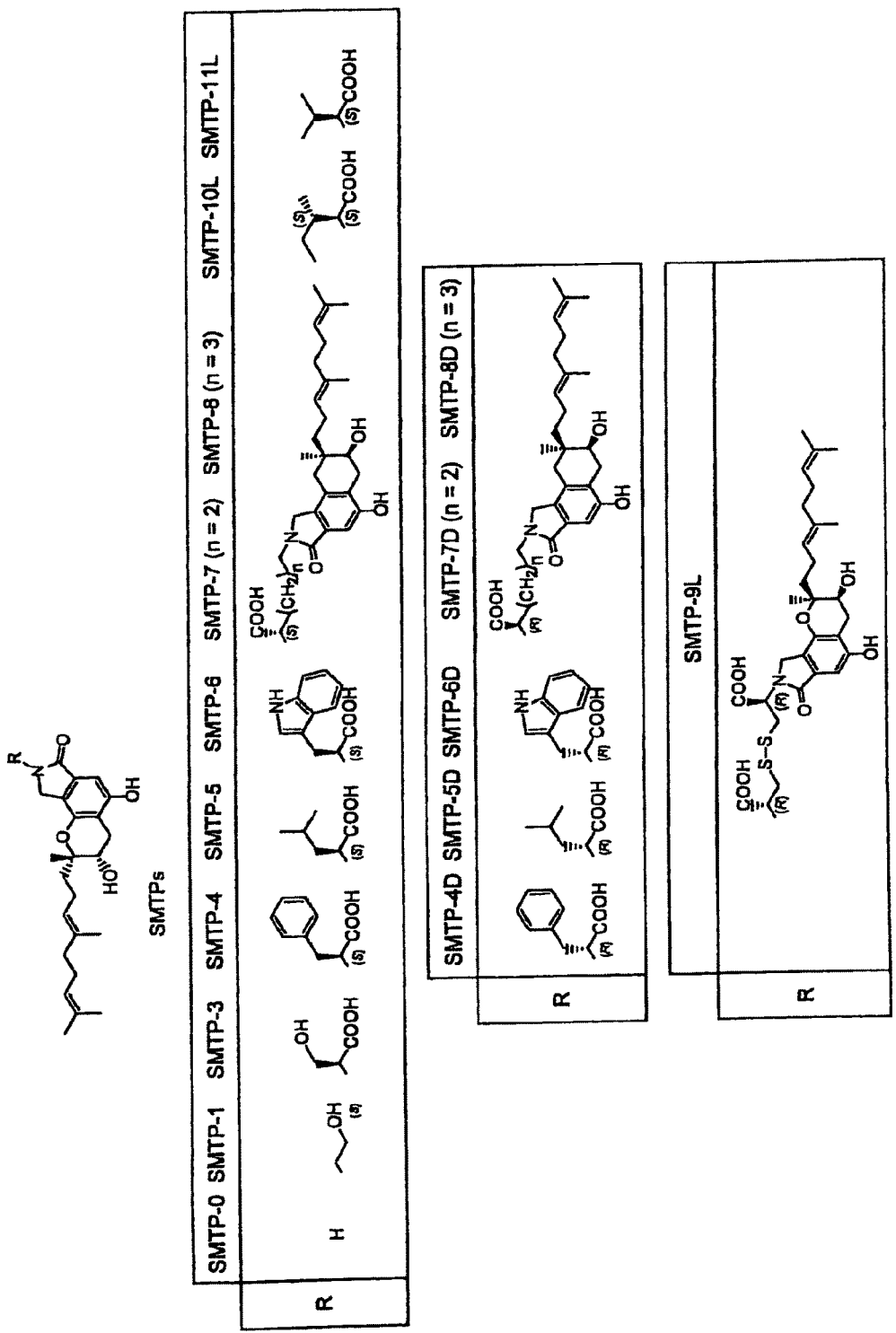
FIG. 1 is a list of the structures of various SMTP compounds according to the invention.

<Method for Producing Triprenyl Phenol Compound, and First Triprenyl Phenol Compound>

The production method for producing a triprenyl phenol compound of the invention is characterized by including culturing a filamentous fungus in a first culturing process using a restricted medium in which at least one of the type and the amount of amine compound is restricted, culturing the filamentous fungus in a second culturing process using a production medium containing an amine compound, which process commences at an intermediate stage of culture, and obtaining a triprenyl phenol compound from the culture obtained after the second culturing process.

In the production method described above, since a restricted medium in which at least one of the type and the amount of amine compound is restricted is used as the medium used in the first culturing process, after the intermediate stage of culture at which the second culturing process commences, larger amounts of an intermediate compound can be obtained, compared to conventional methods. Thereafter, when the second culturing process is performed using a production medium containing an amine compound, a desired triprenyl phenol compound can be obtained efficiently with good selectivity.

The first triprenyl phenol compound of the invention is a compound which is represented by the following formula (I) and has a negative (−) optical rotation. In the formula, X is —CHY—(CH$_3$)$_2$Z; and Y and Z are respectively —H or —OH, or together form a single bond.

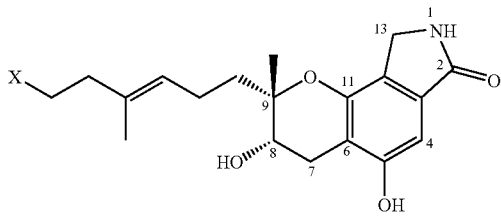

(I)

In the triprenyl phenol compound represented by formula (I), while the nitrogen atom at the 1-position is a secondary amine, both the 8-position and the 9-position have an absolute configuration of (S), and the compound as a whole exhibits an overall negative (−) optical rotation. Since such optical activity and absolute configuration are identical to those of an active triprenyl phenol compound having physiological activity such as thrombolysis enhancement, when the substituent at the 1-position in the present compound is appropriately changed, various triprenyl phenol compounds can be easily obtained.

Hereinafter, the method for producing a triprenyl phenol compound of the invention will be described.

In the production method of the invention, a filamentous fungus of the genus *Stachybotrys* is selected as the filamentous fungus used for obtaining a triprenyl phenol compound. A particularly preferred production microorganism is *Stachybotrys microspora* or the like, and the *Stachybotrys microspora* (*S. microspora*) strain IFO30018 is even more preferred, but the invention is not intended to be limited to this fungus.

In the production method of the invention, the filamentous fungus is cultured by a two-stage culturing process including a first culturing process using a restricted medium and a second culturing process using a production medium carried out from an intermediate stage of culture.

In the first culturing process, a restricted medium in which at least one of the type and the amount of amine compound is restricted is used. The phrase "at least one of the type and the amount is restricted" as used herein means that the amount of a selected amine compound to be added to the restricted medium is determined in accordance with the type of the amine compound. When such restricted medium in which at least one of the type and the amount of amine compound is restricted is used, a triprenyl phenol compound can be produced efficiently with good selectivity in the second culturing process which commences at an intermediate stage of culture.

In the second culturing process which commences at an intermediate stage of culture, a production medium containing an amine compound is used. The term "intermediate stage of culture" as used herein may be defined as a stage after a given period from the initiation of culture, this given period being provided in order to securely prolong the first culturing process, preferably on the second day or thereafter, and more preferably on the fourth day or thereafter, from the initiation of culture. If this period is too short, that is, for example, if the culturing using a production medium is initiated immediately after the initiation of the culture, the amount of the intermediate compound required for obtaining the desired triprenyl phenol compound is insufficient, and thus the triprenyl phenol compound cannot be produced efficiently.

In the production method of the invention, the restricted medium used in the first culturing process can be set to contain 0.5% by mass or less of an amine compound, and the production medium used in the second culturing process can be set to contain an organic amine compound (hereinafter, referred to as "first production method of the invention").

Thereby, an intermediate compound containing a functional group corresponding to the organic amine compound contained in the production medium, for example, a compound represented by the following formula (I-B), can be obtained without impairing the compound production ability of the filamentous fungus in the restricted medium. In the formula (I-B), X has the same meaning as defined above, and the reference numeral # represents a predetermined functional group corresponding to the amine compound contained in the production medium

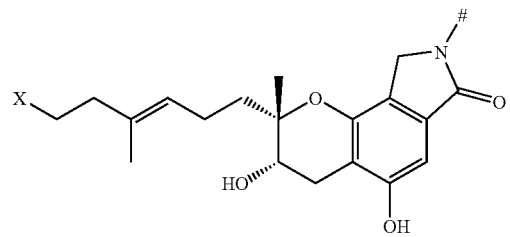

(I-B)

In the first production method of the invention, the amine compound in the restricted medium encompasses all of the organic and inorganic amine compounds that will be described later. This amine compound serves as a nitrogen source and a growth promoting factor for the growth of a filamentous fungus in the restricted medium, or as a production promoting factor for a triprenyl phenol compound precursor. With regard to the form of addition, the amine compound can be used as a naturally-occurring mixture such as yeast extract, bouillon, peptone, tryptone, soybean meal, Pharmamedia, Corn Steep Liquor or fish meat extract, or as a purified compound. Since the naturally-occurring mixtures contain various species of amine compounds, it is necessary to limit the amount of the naturally-occurring mixtures in the restricted medium. In this case, the amount can be set to 0.5% by mass or less, and in view of the growth of fungus, the quantity of production, and selectivity in the production, can preferably be set to 0.01 to 0.5% by mass, and more preferably 0.1% by mass to 0.3% by mass, based on the total volume of the restricted medium. If the amount exceeds 0.5% by mass, compounds other than the intermediate compound are simultaneously generated, resulting in a decrease in the selectivity, and thus the production efficiency may also be decreased, which is not preferable. On the other hand, if the amount is less than 0.01% by mass, the activity of the filamentous fungus may be reduced, which is not preferable. Furthermore, in the case of adding a purified compound as the amine compound, the compound is used in an amount and type within a range in which the growth of the filamentous fungus used in the production and the production of the triprenyl phenol compound precursor occur favorably.

The filamentous fungus cultured in the restricted medium is supplied, at the intermediate stage of culture, to the culture in the second culturing process that uses a production medium containing an organic amine compound.

The production medium used in the second culturing process can be constituted with the same composition as the restricted medium apart from the inclusion of an organic amine compound. For this reason, the culture in the second culturing process may be performed by adding an organic amine compound to the restricted medium used in the first culturing process, or a freshly prepared amine compound-containing medium may be directly added.

The organic amine compound that can be contained in the production medium in the second culturing process may be present in the medium in an amount necessary for obtaining the desired triprenyl phenol compound, and is used in an amount of 5% by mass or less, and in view of the quantity of production, in an amount of preferably 0.01% by mass to 1% by mass, and more preferably 0.1% by mass to 0.5% by mass, based on the total volume of the medium.

Examples of the organic amine compound in the first production method of the invention include a synthetic product or a naturally-occurring amine compound. Examples of the naturally-occurring amine compound component generally include proteins or components conventionally used to add naturally-occurring amino acids to culture media, such as yeast extract, bouillon, peptone, tryptone, soybean meal, Pharmamedia, Corn Steep Liquor and fish meat extract. In view of the quantity of production, yeast extract and peptone are preferred.

In view of the type and quantity of production of the triprenyl phenol compound produced, it is preferable that the organic amine compound added to the production medium contains a primary amine compound. The primary amine compound includes naturally-occurring amino acids and synthetic amino acids, and examples thereof include valine, leucine, isoleucine, phenylalanine, tryptophan, cystine, lysine and ornithine as α-amino acids, and those obtained by substituting the carboxyl group of a naturally-occurring amino acid with hydrogen, a hydroxyl group or a hydroxymethyl group, for example, amino alcohols such as 2-aminoethanol, and the like.

Among them, the type of the amine compound contained in the production medium in the second culturing process can be appropriately selected in accordance with the type of the desired triprenyl phenol compound.

For example, in order to obtain an active triprenyl phenol compound having a thrombolysis promoting action, a production medium containing an amino acid such as D-lysine, D-phenylalanine, D-leucine, D-tryptophan or D-ornithine may be favorably used.

Specifically, desired triprenyl phenol compounds can be selectively produced by using a production medium containing D-serine for SMTP-3D, a medium containing D-phenylalanine for SMTP-4D, a medium containing D-leucine for SMTP-5D, a medium containing D-tryptophan for SMTP-6D, a medium containing D-ornithine for SMTP-7D, a medium containing D-lysine for SMTP-8D, a medium containing L-serine for SMTP-3, a medium containing L-phenylalanine for SMTP-4, a medium containing L-leucine for SMTP-5, a medium containing L-tryptophan for SMTP-6, a medium containing L-ornithine for SMTP-7, a medium containing L-lysine for SMTP-8, a medium containing L-cystine for SMTP-9L, a medium containing L-isoleucine for SMTP-10L, and a medium containing L-valine for SMTP-11L (see FIG. 1).

It is desirable that the content of the amino acid in the production medium for the second culturing process is 0.03% by mass to 0.3% by mass based on the volume of the production medium.

As the inorganic amine compounds according to the present production method, nitric acid which is contained as an inorganic salt, inorganic primary amine compounds and the like may be mentioned. Further description concerning the inorganic primary amine compounds will be given below.

The restricted medium and the production medium contain, in addition to the above-described components, additives components for synthetic media which are conventionally used in the culture of the microorganisms described above, for the purpose of promoting the microbiotic production of compounds, or the like. Examples of the additive components that can be added to the present restricted medium include nutrient sources such as glucose, sucrose, dextrin, animal oils and plant oils, vitamins and inorganic salts capable of generating, for example, chlorine, nitrate, sulfate, phosphate, sodium, potassium, calcium, magnesium, cobalt and other ions.

Among the inorganic salts, particularly the inorganic salts capable of generating metal ions can be preferably added to the restricted medium, from the viewpoint of enhancing the quantity of production of the product or production efficiency. Such metal ions include magnesium ions, cobalt ions, iron ions, calcium ions, potassium ions, sodium ions, and the like.

The amount of addition of these metal ions can be set to 0.001% by mass to 0.5% by mass (more preferably, 0.01% by mass to 0.1% by mass) as magnesium sulfate heptahydrate in the case of magnesium ions; 0.00001% by mass to 0.01% by mass (more preferably, 0.0001% by mass to 0.005% by mass) as cobalt chloride hexahydrate in the case of cobalt ions; 0.0001% by mass to 0.1% by mass (more preferably, 0.0005% by mass to 0.05% by mass) as iron(II) sulfate heptahydrate in the case of iron ions; 0.00001% by mass to 0.1% by mass (more preferably, 0.0001% by mass to 0.05% by mass) as calcium chloride dihydrate in the case of calcium ions; 0.002% by mass to 2% by mass (more preferably, 0.05% by mass to 0.5% by mass) as dibasic potassium phosphate in the case of potassium ions; and 0.002% by mass to 2% by mass (more preferably, 0.05% by mass to 0.5% by mass) as dibasic sodium phosphate or sodium nitrate in the case of sodium ions.

These inorganic salts and metal ions may be used singly, or may be used in combination of two or more species.

The first culturing process using the restricted medium is continued to the intermediate stage of culture by which a sufficient amount of the intermediate compound is obtained to obtain the desired triprenyl phenol compound efficiently. From the viewpoint of efficient production of the triprenyl phenol compound, the second culturing process using the production medium is carried out preferably on the second day or thereafter, and more preferably on the fourth day or thereafter from the initiation of the culture of filamentous fungus the culture.

The second culturing process is completed by terminating the culture when the amount of the produced triprenyl phenol compound is maximal. The period of the second culturing process may vary with the state of the microorganism and the size of the culture system, but the period is generally 1 day to 5 days, and preferably 1 to 3 days from the viewpoint of the quantity of production.

In the production method of the invention, the restricted medium used in the first culturing process can be set to contain 0.5% by mass or less of an organic amine compound, and the production medium used in the second culturing process can be said to contain an inorganic primary amine compound (hereinafter, referred to as "second production method of the invention" herein).

Thereby, a compound represented by the following formula (I), which contains a secondary amine corresponding to the inorganic primary amine compound contained in the production medium, and having a negative (−) optical rotation, can be obtained, without impairing the compound producing ability of the filamentous fungus in the restricted medium. In the formula, X is —CHY—(CH$_3$)$_2$Z; and Y and Z are each —H or —OH, or together form a single bond.

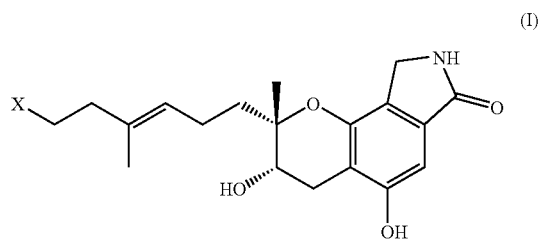

(I)

In the second production method of the invention, the restricted medium contains 0.5% by mass or less of an organic amine compound. The organic amine compound as used herein may be exemplified by the same compounds described above for the first production method, and may be preferably exemplified by naturally-occurring amine compound components. Thus, an intermediate compound can be obtained without impairing the production ability of the filamentous fungus. The content of the organic amine compound in the restricted medium can be set to 0.5% by mass or less, and from the viewpoints of the growth of fungus, the quantity of production and selectivity in the production, preferably 0.01 to 0.5% by mass, and more preferably 0.1% by mass to 0.3% by mass, based on the total volume of the restricted medium. If more than 0.5% by mass of an organic amine compound is contained, compounds other than the intermediate compound corresponding to the compound of formula (I) are simultaneously generated, resulting in a decrease in the selectivity, and thus the production efficiency may also be decreased, which is not preferable.

The restricted medium of the present production method may contain an inorganic amine compound. This inorganic amine compound may be a nitrate contained as an inorganic salt or other inorganic amines, and from the viewpoint of the structure of the resulting triprenyl phenol compound, an inorganic primary amine compound is preferably contained. The content of the inorganic amine compound that can be contained in the restricted medium may vary with the type and amount of the desired triprenyl phenol compound, but from the viewpoints of the growth of fungus, the quantity of production and selectivity in the production, the content is preferably 1% by mass or less, and from the viewpoint of productivity, is more preferably 0.5% by mass or less, and even more preferably 0.3% by mass or less, based on the volume of the restricted medium.

In the second production method of the invention, the production medium contains an inorganic primary amine compound. Thereby, the compound of formula (I) can be obtained efficiently.

Examples of the inorganic primary amine compound contained in the restricted medium and the production medium include ammonium salts such as ammonium chloride, ammonium acetate, ammonium sulfate, and ammonium phosphate. Among them, ammonium chloride is preferred from the viewpoint of the quantity of production of the product.

The inorganic amine compound that can be contained in the production medium in the second culturing process may be present in the medium in an amount necessary for obtaining the desired triprenyl phenol compound, and is used in an amount of 5% by mass or less, and from the viewpoint of the quantity of production, preferably in an amount of 0.01% by mass to 1% by mass, and more preferably 0.1% by mass to 0.5% by mass, based on the total volume of the medium.

The restricted medium and the production medium in the second production method of the invention preferably contain inorganic salts, as in the case of the first production method of the invention, from the viewpoints of the growth of the filamentous fungus and the quantity of production of the compound produced. With regard to the inorganic salts and metal ions that can be contained, the subject matter described above can be applied similarly.

The first and second culturing processes in the first and second production methods of the invention are typically carried out by stationary culture or shaking culture using the media described above. In the case of applying shaking culture, the culture may be conducted at a speed conventionally applied in the culture of fungi, and for example, in the case of using a rotary shaker of model TB-25S (vibrational amplitude 70 mm) manufactured by Takasaki Scientific Instruments Corp., and a medium amount of 100 ml in a flask having a capacity of 500 ml, the speed can be set to 30 rpm to 240 rpm, and preferably 160 rpm to 200 rpm.

The culture temperature in the first and second culturing processes can be appropriately set in accordance with the growth conditions of fungi at various temperatures, but the temperature is generally 4 to 50° C., preferably 15 to 37° C., more preferably 20 to 30° C., and even more preferably room temperature (25° C.). Beyond this range, a triprenyl phenol compound cannot be efficiently produced. The pH of the respective media used in the processes can be generally set to 3 to 9, and preferably 5 to 6.

In addition, prior to the first and second culturing processes, a preliminary culturing process may be provided so as to stabilize the production ability of the microorganism. The medium used in the preliminary culturing process may be a conventional growth medium used in maintaining microorganisms.

The obtained triprenyl phenol compound can be obtained by recovery and purification from the culture. The methods of recovery and purification may be any method as long as they are techniques capable of recovering and purifying the triprenyl phenol compound released into the medium, and liquid chromatography, solvent extraction, crystallization and the like may be mentioned. The recovery and purification of the product is preferably performed by a multistage process of two or more stages, from the viewpoint of recovery efficiency.

For these recovery and purification methods, it is preferable to select the solvent and the like, by making use of the fact that the triprenyl phenol compound is oil-soluble.

When the triprenyl phenol compound is to be recovered and purified from the culture, it is preferable to remove the fungus body from the culture in advance. At this time, a solvent such as methanol is added to the culture to extract the triprenyl phenol compound in the fungus body, and the subsequent removal of fungus body may be performed by filtration or the like.

Next, the first triprenyl phenol compound of the invention, that is, a triprenyl phenol compound precursor, will be described.

The triprenyl phenol compound precursor represented by the following formula (I) (wherein X is —CHY—(CH$_3$)$_2$Z; and Y and Z are each —H or —OH, or together form a single bond) has the same optical activity and absolute configuration as those of the active triprenyl phenol compound having physiological activity such as thrombolysis enhancement, as described above. Thus, when the substituent at the 1-position of the compound is appropriately changed with other substituents, various triprenyl phenol compounds can be easily obtained. This is because the 1-position is occupied by a secondary amine, and thus the secondary amine at the 1-position can be modified with a physiologically active substituent. Thereby, an active triprenyl phenol compound having physiological activity such as thrombolysis enhancement can be induced therefrom. At this time, the physiologically active substituent used in the modification can be appropriately selected from the existing substituents, in accordance with the desired activity.

Furthermore, the triprenyl phenol compound has an anticancer effect, a therapeutic effect for renal disorder, and a thrombolysis enhancing action as will be described later, and has pharmacokinetics or absorption characteristics conforming to those purposes. Thus, the triprenyl phenol compound precursor of the invention can also be used in the synthesis of derivatives of such triprenyl phenol compound.

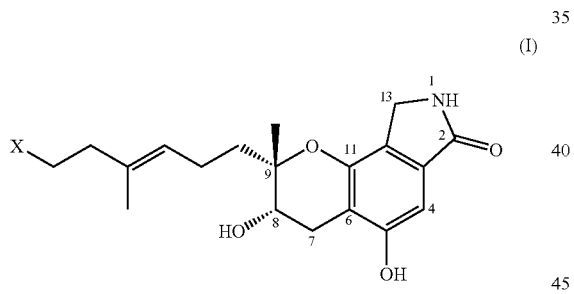

(I)

In general, it is known that physiologically active substances may have largely different properties due to the optical activity or the like, even though the substances have the same planar structure. With regard to the triprenyl phenol compound, a compound having an absolute configuration of 8(R) and 9(R), and a positive (+) optical rotation, exhibits effects that are different from those of a compound having an absolute configuration of 8(S) and 9(S), and a negative (–) optical rotation. The triprenyl phenol compound of the invention is useful for efficiently obtaining an active triprenyl phenol compound which exhibits an absolute configuration of 8(S) and 9(S) and a negative (–) optical rotation, and has useful physiological activity in a living body.

Here, the absolute configuration of the 8-position and 9-position and the optical rotation can be confirmed using well known means that are conventionally used in the related art to confirm the stereostructure of a compound, for example, C-NMR, H-NMR, mass analysis, IR, X-ray crystal structure analysis, specific optical rotation and the like.

From the viewpoint of physiological activity, a triprenyl phenol compound represented by the following formula (I-A) wherein Y and Z are joined together to form a single bond, and having a negative (–) optical rotation, is particularly preferred.

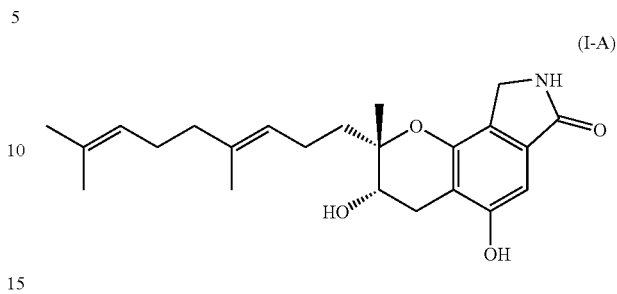

(I-A)

The first triprenyl phenol compound of the invention can be obtained according to a production method using chemical synthesis or microorganisms, but it is particularly preferable to use the second production method of the invention because the subject compound can be obtained efficiently.

<Second Triprenyl Phenol Compound>

The second triprenyl phenol compound of the invention is a compound represented by the following formula (II).

This second triprenyl phenol compound is a monomer as well as a low molecular weight compound in which, in addition to the triprenyl phenol skeleton, an aromatic group having a predetermined substituent that will be described later, is directly bound to the nitrogen atom at the 1-position, and can exhibit a high plasminogen activation enhancing action even at low concentration.

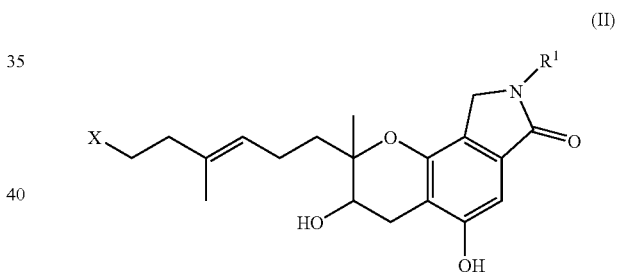

(II)

wherein R$^1$ represents an aromatic group having as a substituent or as a part of a substituent at least one group selected from the group consisting of a carboxyl group, a hydroxyl group, a sulfonic acid group and a secondary amino group, or an aromatic group which contains a secondary amino group and may contain nitrogen. That is, the subject compound has an aromatic group directly linked to the nitrogen atom of the triprenyl phenol skeleton. In the case where a plurality of substituents is present on the aromatic groups, they may be identical with or different from each other. Such substituent is, from the viewpoint of absorbability, an aromatic group having a molecular weight of 200 or less for the entire substituents, more preferably 160 or less, and particularly preferably 140 or less. The position of the substituent on the aromatic group may be any of the para-position, meta-position and ortho-position relative to the nitrogen atom of the triprenyl phenol skeleton.

The aromatic group in the subject compound may be an aromatic group as a substituent or as a part of a substituent having at least one group selected from the group consisting of a carboxyl group, a hydroxyl group, a sulfonic acid group and a secondary amino group, or an aromatic group which contains a secondary amino group and may contain nitrogen, and may further have another substituent as an additional substituent. As such additional substituent, a lower alkyl group, for example, an alkyl group having 1 to 5 carbon atoms, may be mentioned.

The aromatic group is preferably one represented by the following formula (II-1), from the viewpoint of the thrombolytic action. In the following formula (II-1), $R^2$ and $R^3$ respectively represent a hydrogen atom, a carboxyl group, a hydroxyl group or a sulfonic acid group, or are joined together to represent a cyclic group containing a secondary amino group, but do not both represent hydrogen atoms at the same time.

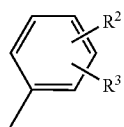
(II-1)

Such aromatic group is more preferably one selected from the following, from the viewpoint of the thrombolytic action.

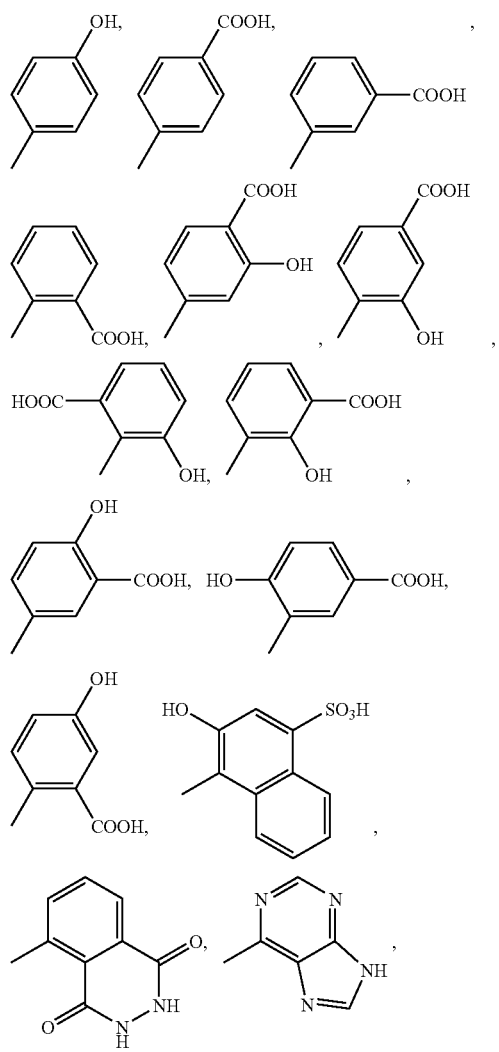

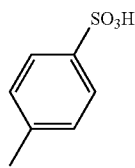

Such aromatic group can be derived from an additive amine compound selected from the group consisting of aminophenol, aminobenzoic acid, adenine, adenosine, aminodihydrophthalazinedione, aminonaphtholsulfonic acid, sulfanilic acid and derivatives thereof, as will be described later.

Furthermore, in the formula, X is —CHY—(CH$_3$)$_2$Z; and Y and Z are respectively —H or —OH, or together form a single bond. From the viewpoint of physiological activity, it is preferable that Y and Z are joined together to form a single bond.

As such second triprenyl phenol compound, the following may be mentioned.

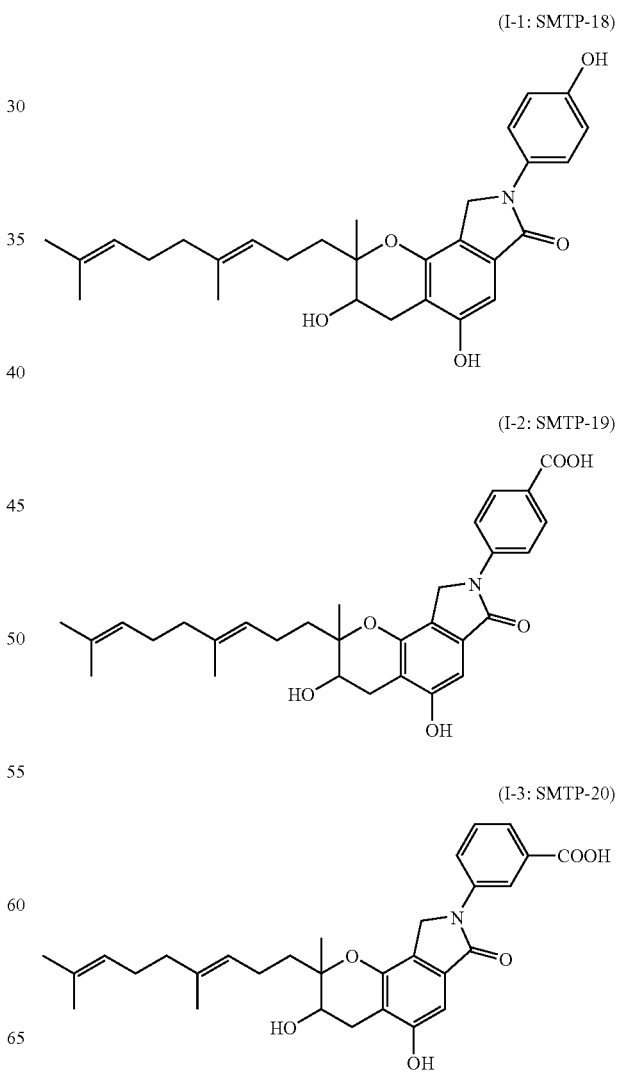

-continued
(I-4: SMTP-21)
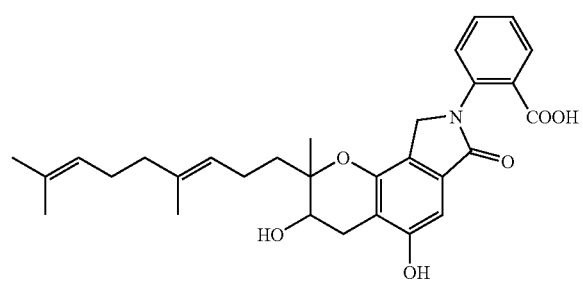
(I-5: SMTP-22)
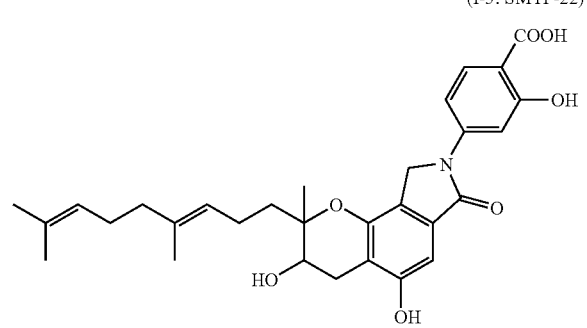
(I-6: SMTP-23)
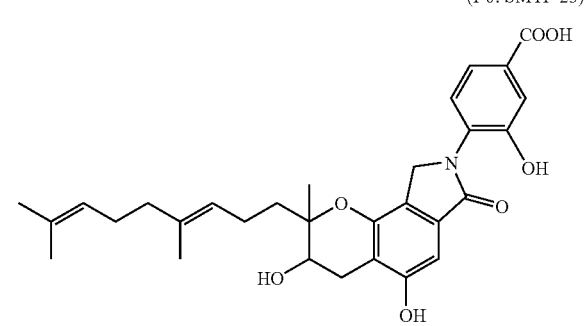
(I-7: SMTP-24)
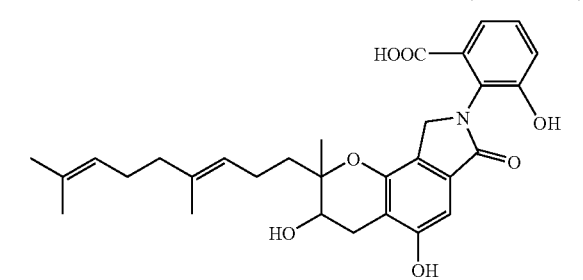
(I-8: SMTP-25)
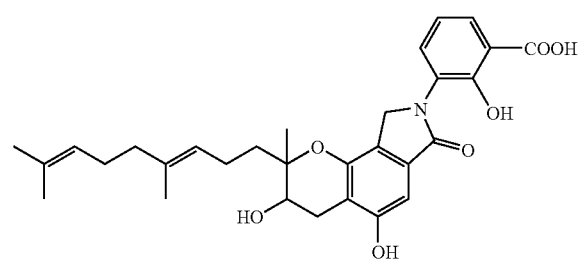
-continued
(I-9: SMTP-26)
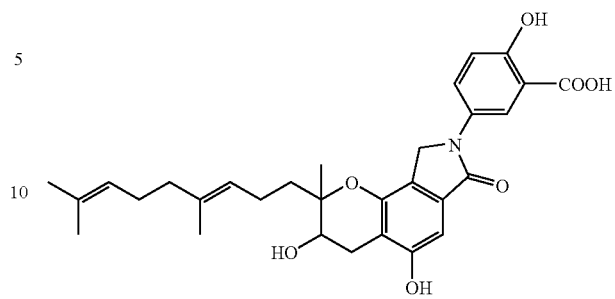
(I-10: SMTP-27)
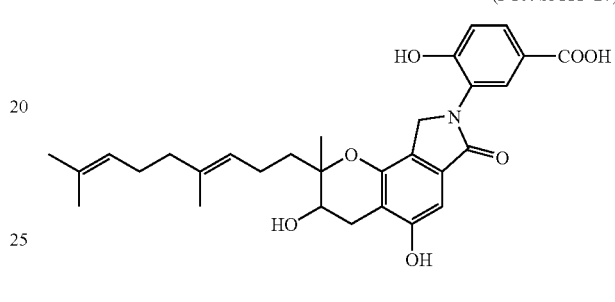
(I-11: SMTP-28)
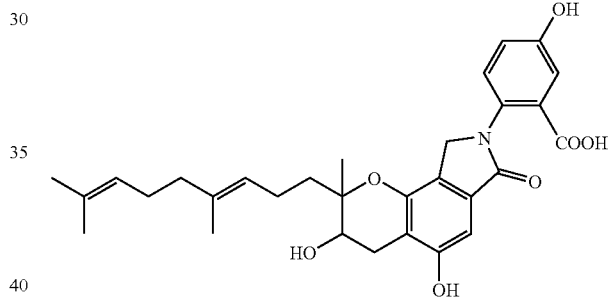
(I-12)
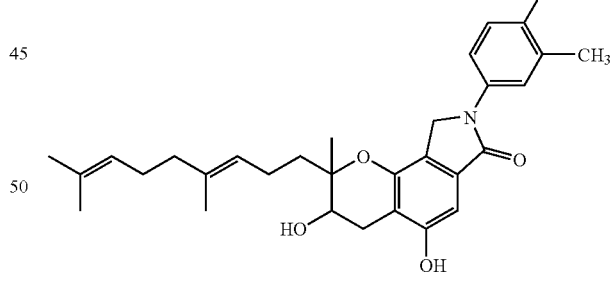
(I-13)
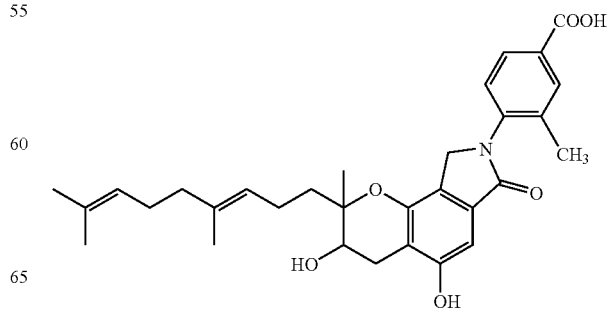

-continued (I-14)
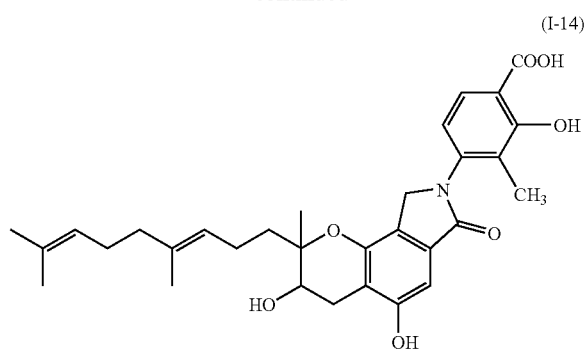

(I-15)
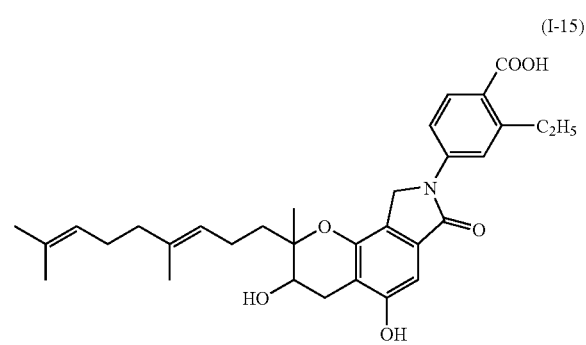

(I-16: SMTP-32)
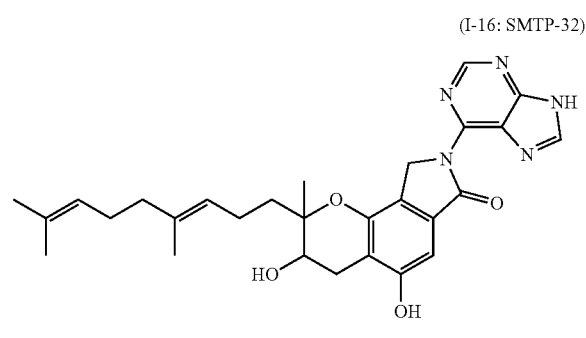

(I-17: SMTP-36)
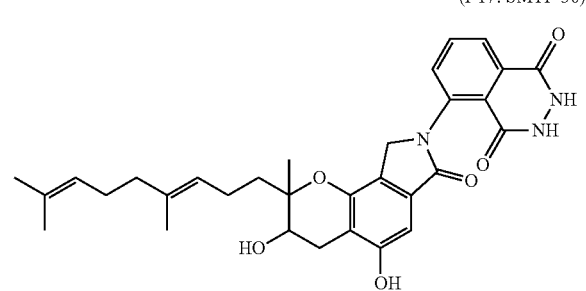

(I-18: SMTP-37)
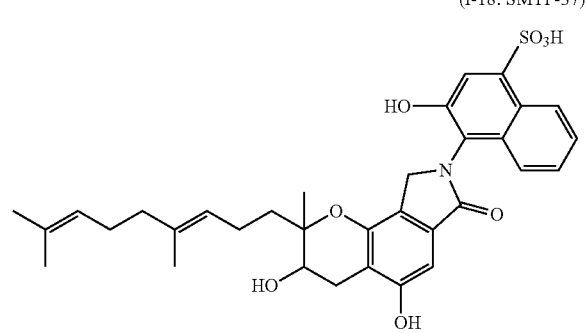

-continued (I-19: SMTP-42)
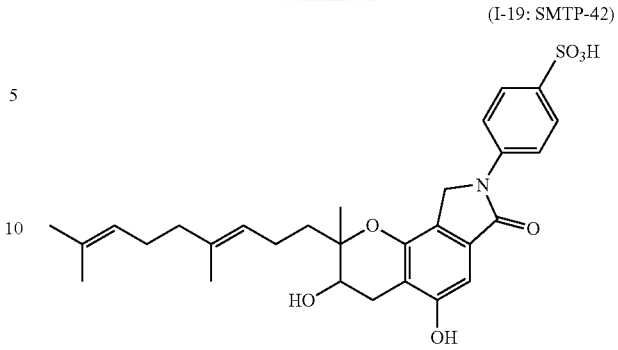

The second triprenyl phenol compound of the invention can be produced by chemical synthesis, but can also be efficiently produced using a filamentous fungus.

Specifically, the production method for producing the second triprenyl phenol compound of the invention includes culturing a filamentous fungus in a medium containing the additive amine compound that will be described later, and separating the triprenyl phenol compound from the culture obtained after the culturing.

In the present production method, the filamentous fungus takes up the additive amine compound present in the medium, which compound is aminophenol, aminobenzoic acid, adenine, adenosine, aminodihydrophthalazinedione, aminonaphtholsulfonic acid, sulfanilic acid or a derivative thereof, as an aromatic group to be directly linked to the triprenyl phenol skeleton. Thereby, the second triprenyl phenol compound can be efficiently obtained.

As the filamentous fungus used to obtain the triprenyl phenol compound of the invention, a filamentous fungus of the genus *Stachybotrys* is selected. A particularly preferred productive fungus is *Stachybotrys microspora* or the like, and is more preferably *Stachybotrys microspora* strain IFO30018. However, the invention is not limited to this fungus.

In the present production method, the additive amine compound according to the present production method may be present in the process of culturing the filamentous fungus, and may be allowed to be present from the early phase of culture. However, from the viewpoint of production efficiency, it is preferable that the additive amine compound is added at the intermediate stage of culture.

In the case of adding the additive amine compound at the intermediate stage of culture, the process of culturing the filamentous fungus preferably includes a first culturing process using a restricted medium having a content of an amine compound of 0.5% by mass or less, and a second culturing process using a production medium containing an additive amine compound, which process commences at the intermediate stage of culture.

Since a restricted medium in which the content of the amine compound is limited to 0.5% by mass is used as the medium used in the first culturing process, after the intermediate stage of culture at which the second culturing process commences, larger amounts of an intermediate compound can be obtained, compared to conventional methods. Furthermore, after producing large amounts of an intermediate compound as such, when the second culturing process using a production medium containing an additive amine compound for obtaining a second triprenyl phenol compound is carried out, a desired second triprenyl phenol compound can be obtained efficiently with good selectivity. Additionally, the term "amine compound" as used herein includes the additive amine compounds, unless stated otherwise.

The production method for producing the second triprenyl phenol compound is the same as described for the first production method in the above-described method for producing the triprenyl phenol compound of the invention, except for the type of the additive amine compound, and the subject matter described in the above can be applied without any modification.

The additive amine compound may have a substituent other than a carboxyl group, a hydroxyl group, a sulfonic acid group and a secondary amino group, and may have a lower alkyl group, for example, an alkyl group having 1 to 5 carbon atoms. Further, the additive amine compound may also have a plurality of amino groups, but from the viewpoint of production efficiency, it is preferable that the amine compound has one amino group.

Such amine compound that can be added is preferably a monoamine compound having both a carboxyl group and a hydroxyl group, from the viewpoint of the thrombolysis enhancing action.

As the additive amine compound, there may be mentioned aminophenol, aminobenzoic acid, adenine, adenosine, aminodihydrophthalazinedione, aminonaphtholsulfonic acid, sulfanilic acid and derivatives thereof. Examples of such additive amine compound include aminophenol, methylaminophenol, aminobenzoic acid, aminosalicylic acid, aminohydroxybenzoic acid, hydroxyanthranilic acid, adenine, adenosine, aminodihydrophthalazinedione, aminonaphtholsulfonic acid and sulfanilic acid, and for example, p-aminobenzoic acid, 3-aminosalicylic acid, o-aminobenzoic acid, 4-amino-3-hydroxybenzoic acid, 3-hydroxyanthranilic acid, 5-hydroxyanthranilic acid, 4-aminosalicylic acid, 5-aminosalicylic acid, 3-amino-4-hydroxybenzoic acid, 4-amino-3-methylsalicylic acid, adenine, adenosine, 5-amino-2,3-dihydro-1,4-phthalazinedione, 1-amino-2-naphthol-4-sulfonic acid, p-sulfanilic acid and derivatives thereof may be mentioned. These additive amine compounds can be used singly or in combination of two or more species.

Among these, from the viewpoint of the thrombolysis enhancing action, p-aminobenzoic acid, o-aminobenzoic acid, 3-aminosalicylic acid, 4-amino-3-hydroxybenzoic acid, 3-hydroxyanthranilic acid, 5-hydroxyanthranilic acid, 3-amino-4-hydroxybenzoic acid, 4-aminosalicylic acid, 5-amino-2,3-dihydro-1,4-phthalazinedione and 1-amino-2-naphthol-4-sulfonic acid are preferred.

The additive amine compound that can be contained in the production medium in the second culturing process may be present in the medium in an amount necessary for obtaining the desired triprenyl phenol compound, and is used in an amount of 5% by mass or less, and from the viewpoint of the quantity of production, preferably in an amount of 0.01% by mass to 1% by mass, and more preferably 0.1% by mass to 0.5% by mass, based on the total volume of the medium.

<Third Triprenyl Phenol Compound>

The third triprenyl phenol compound of the invention is a triprenyl phenol compound represented by the following formula (III).

This third triprenyl phenol compound has a substituent derived from an α-aromatic amino acid, which is directly bound to the nitrogen atom at the 1-position of the triprenyl phenol skeleton. Because of this, the second triprenyl phenol compound has only one or two methyl groups disposed between this nitrogen atom at the 1-position and the aromatic ring. As a result, the second triprenyl phenol compound is a monomer as well as a low molecular weight compound, and can exhibit a high plasminogen activation enhancing action even at low concentration.

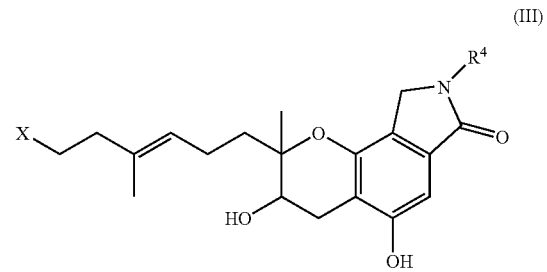

(III)

wherein $R^4$ represents an aromatic amino acid residue represented by the following formula (III-1). In the following Formula (III-1), $R^5$ represents a hydroxyl group which may be present or absent, and n represents an integer of 0 or 1.

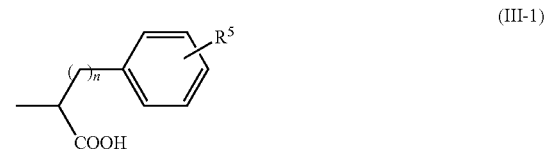

(III-1)

The aromatic amino acid residue in the subject compound is preferably a residue having a molecular weight of 200 or less, more preferably 160 or less, and particularly preferably 140 or less, for the substituent as a whole, from the viewpoint of absorbability. This aromatic amino acid residue may further have another substituent other than the carboxyl group at the α-position, as an additional substituent. Such additional substituent may be a hydroxyl group, a carboxyl group, or for example, an alkyl group having 1 to 5 carbon atoms. In addition, the position of the substituent linked to the aromatic ring in the aromatic amino acid residue may be any of the para-position, meta-position and ortho-position.

Such aromatic amino acid residue is preferably phenylglycine, tyrosine or a derivative thereof, from the viewpoint of the thrombolytic action. In addition, in the case of a tyrosine residue, the position of the hydroxyl group, carboxyl group, lower alkyl group or the like linked to the aromatic ring may be any of the para-position, meta-position and ortho-position. Among them, the following are more preferred as such aromatic amino acid residue.

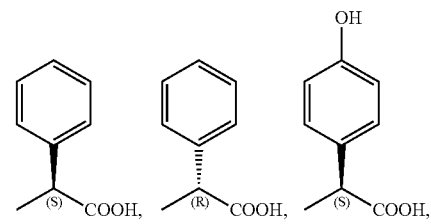

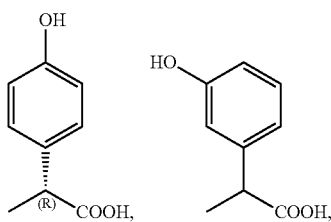

Such aromatic amino acid residue can be derived from an additive amine compound selected from the group consisting of phenylglycine, tyrosine and derivatives thereof, as will be described later.

In the formulas, X is —CHY—(CH$_3$)$_2$Z; and Y and Z are each —H or —OH, or together form a single bond. From the viewpoint of physiological activity, it is preferable that Y and Z are joined together to form a single bond.

As such third triprenyl phenol compound, the following may be mentioned.

(I-20: SMTP-43)

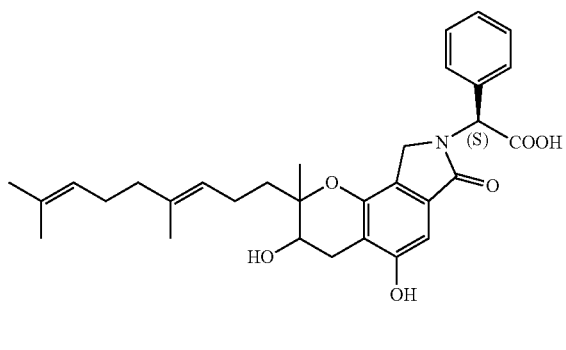

(I-21: SMTP-43D)

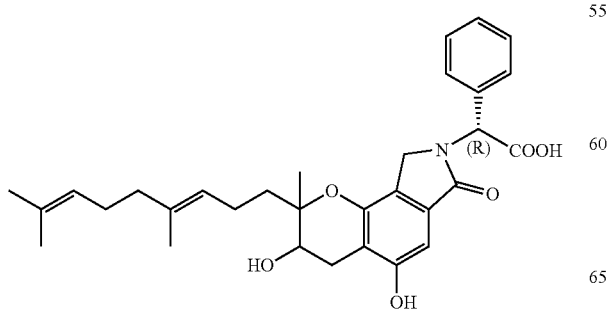

(I-22: SMTP-44)

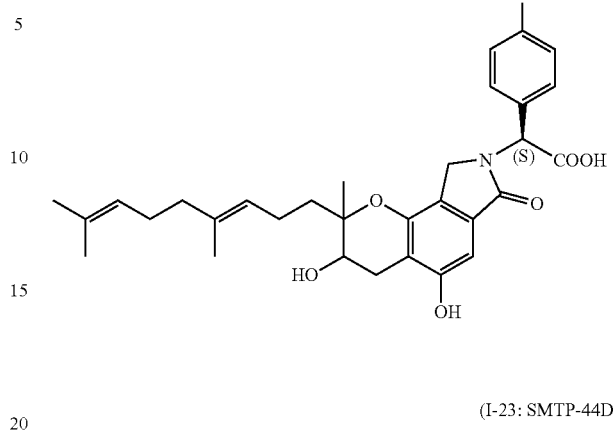

(I-23: SMTP-44D)

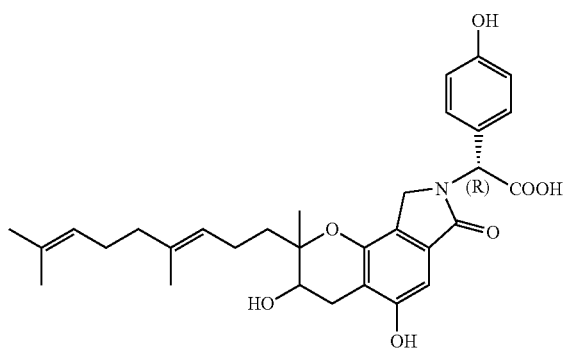

(I-24: SMTP-45-I)

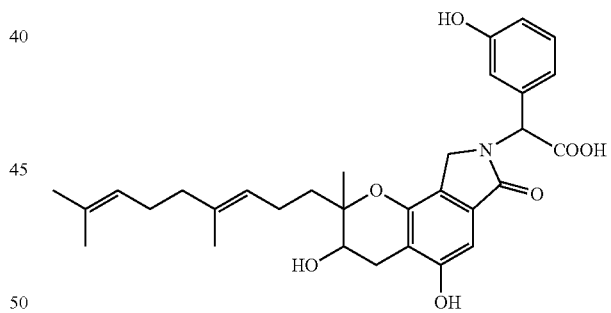

(I-25: SMTP-45-II)

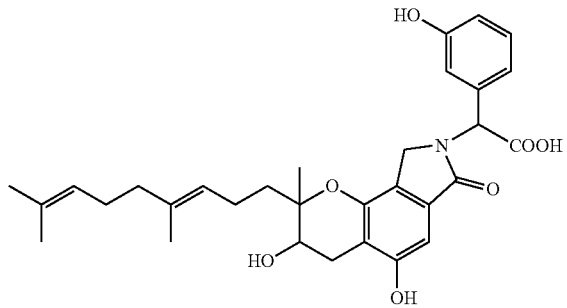

(I-26: SMTP-14)

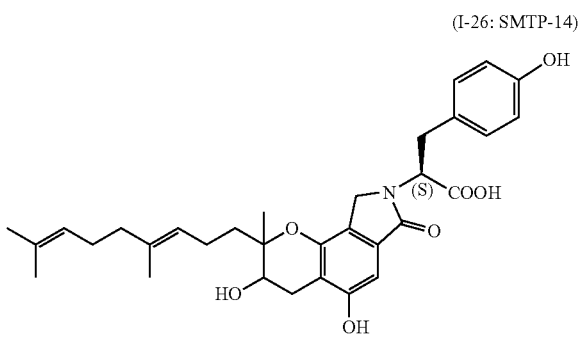

(I-27)

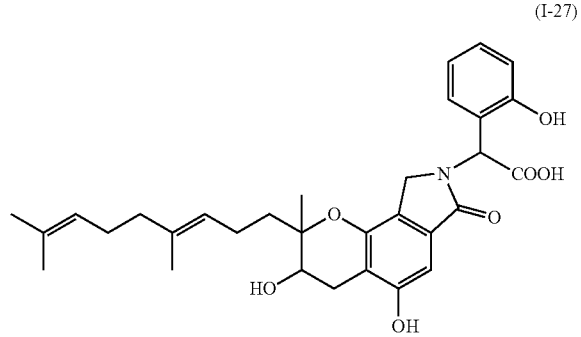

(I-28)

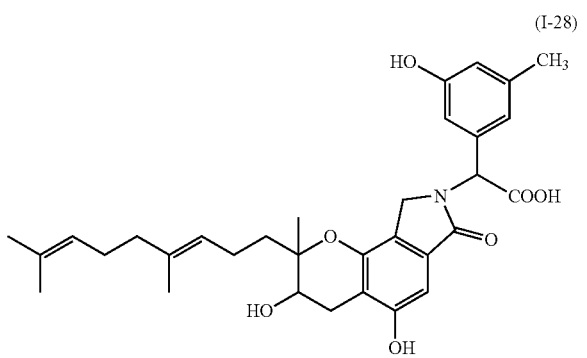

(I-29)

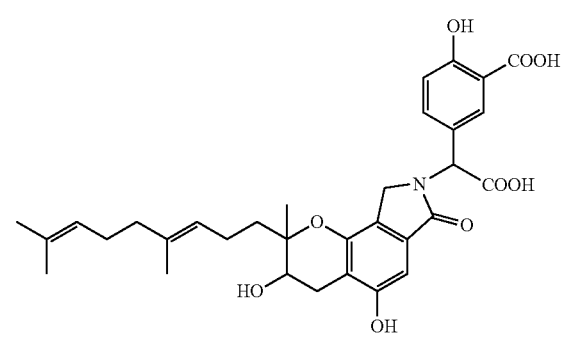

(I-30)

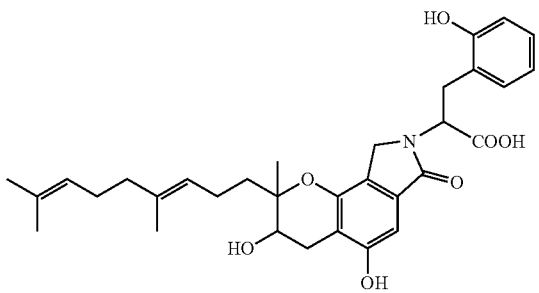

The third triprenyl phenol compound of the invention can be produced by chemical synthesis, but can also be efficiently produced using a filamentous fungus.

Specifically, the production method for producing the third triprenyl phenol compound of the invention includes culturing a filamentous fungus in a medium containing an additive amine compound that will be described later, and separating the triprenyl phenol compound from the culture obtained after the culturing.

In the present production method, the filamentous fungus takes up the additive amine compound in the medium, which compound is an aromatic amino acid or a derivative thereof, as an α-aromatic amino acid residue to be directly linked to the nitrogen atom of the triprenyl phenol skeleton. Thereby, the third triprenyl phenol compound can be efficiently obtained.

As the filamentous fungus used to obtain the third triprenyl phenol compound of the invention, a filamentous fungus of the genus *Stachybotrys* is selected, as in the case of the production methods described above. A particularly preferred productive fungus is *Stachybotrys microspora* or the like, and more preferably *Stachybotrys microspora* strain IFO30018. However, the invention is not to be limited to this fungus.

In the method for producing the third triprenyl phenol compound, the additive amine compound which is an aromatic amino acid or a derivative thereof, may be present during the process of culturing the filamentous fungus, and may be allowed to be present from the early phase of culture. However, from the viewpoint of production efficiency, it is preferable that the amine compound is added at the intermediate stage of culture.

In the case of adding the additive amine compound at the intermediate stage of culture, it is preferable that the process of culturing the filamentous fungus includes a first culturing process using a restricted medium having a content of the amine compound of 0.5% by mass or less, and a second culturing process using a production medium containing the additive amine compound, which process commences at the intermediate stage of culture.

Since a restricted medium in which the content of the amine compound is restricted to 0.5% by mass is used as the medium used in the first culturing process, after the intermediate stage of culture at which the second culturing process commences, larger amounts of an intermediate compound can be obtained, compared to conventional methods. Furthermore, when the second culturing process using a production medium containing an additive amine compound, intended for obtaining the third triprenyl phenol compound, is carried out after generating a large amount of an intermediate compound as such, the desired third triprenyl phenol compound can be obtained efficiently with good selectivity.

In the invention, the term "amine compound" includes additive amine compounds, unless stated otherwise.

The production method for producing the third triprenyl phenol compound is the same as described for the first production method in the above-described method for producing a triprenyl phenol compound of the invention, except for the type of the additive amine compound, and the subject matter described in the above can be applied without any modification.

The additive amine compound may have a substituent other than an amino group and a carboxyl group, and may also have a hydroxyl group, or for example, a lower alkyl group having 1 to 5 carbon atoms. Further, the additive amine compound may have a plurality of amino groups, but from the viewpoint of production efficiency, it is preferable that the amine compound has one amino group.

As the additive amine compound, phenylglycine, hydroxyphenylglycine, tyrosine and derivatives thereof may be mentioned. Examples of such additive amine compound include L-phenylglycine, D-phenylglycine, L-hydroxyphenylglycine, D-hydroxyphenylglycine, L-tyrosine, D-tyrosine, L-hydroxymethylphenylglycine, D-hydroxymethylphenylglycine, L-hydroxyethylphenylglycine, D-hydroxyethylphenylglycine, L-carboxyphenylglycine, D-carboxyphenylglycine, L-carboxymethylphenylglycine, D-carboxymethylphenylglycine, L-carboxyethylphenylglycine, D-carboxyethylphenylglycine, L-methyltyrosine, D-methyltyrosine, L-ethyltyrosine, D-ethyltyrosine, L-carboxyphenylalanine, D-carboxyphenylalanine, L-carboxymethylphenylalanine, D-carboxymethylphenylalanine, L-carboxyethylphenylalanine, D-carboxyethylphenylalanine, and the like. Specific examples thereof include L-phenylglycine, D-phenylglycine, L-3-hydroxyphenylglycine, D-3-hydroxyphenylglycine, L-4-hydroxyphenylglycine, D-4-hydroxyphenylglycine, L-p-tyrosine, D-p-tyrosine, L-2-hydroxyphenylglycine, D-2-hydroxyphenylglycine, L (or D)-2 (or 3 or 4)-hydroxy-3 (2 or 4 or 5 or 6)-methyl (or ethyl)-phenylglycine, L (or D)-2 (or 3 or 4)-carboxyphenylglycine, L (or D)-2 (or 3 or 4)-carboxy-3 (2 or 4 or 5 or 6)-methyl (or ethyl)-phenylglycine, L (or D)-o-tyrosine, L (or D)-m-tyrosine, L (or D)-2 (or 3 or 4 or 5 or 6)-methyl (or ethyl)-p (or o or m)-tyrosine, L (or D)-2 (or 3 or 4)-carboxyphenylalanine, L (or D)-2 (or 3 or 4)-carboxy-3 (2 or 4 or 5 or 6)-methyl (or ethyl)phenylalanine, and derivatives thereof. These additive amine compounds may be used singly or in combination of a plurality of species.

Among them, from the viewpoint of the thrombolysis enhancing action, L-phenylglycine, D-phenylglycine, L-3-hydroxyphenylglycine, D-3-hydroxyphenylglycine and L-p-tyrosine are preferred.

The additive amine compound that can be contained in the production medium in the second culturing process may be present in the medium in an amount necessary for obtaining the desired triprenyl phenol compound, and is used in an amount of 5% by mass or less, and from the viewpoint of the quantity of production, preferably in an amount of 0.01% by mass to 1% by mass, and more preferably 0.1% by mass to 0.5% by mass, based on the total volume of the medium.

<Thrombolysis Enhancer>

The thrombolysis enhancer of the invention is characterized in containing at least one of the second and the third triprenyl phenol compounds as an active ingredient.

The second and third triprenyl phenol compounds described above have an effective thrombolysis enhancing action even at low molecular weight.

In the present thrombolytic agent, the triprenyl phenol compounds can be contained in the present thrombolytic agent in a form that is conventionally applicable as a medicine, such as a free form, a pharmaceutically acceptable salt or ester.

Furthermore, for the present thrombolytic agent, the formulation can be appropriately changed in accordance with different dosage forms. For oral dosage forms, there may be mentioned tablets, capsules, powders, fine grains, granules, liquids, syrups and the like, while for parenteral dosage forms, there may be mentioned injections, infusions, suppositories, inhalants, patches and the like.

In order to maintain these forms, additives such as well known solvents and excipients that can be used in these applications, can be incorporated.

The thrombolytic agent of the invention can be administered in appropriate doses according to the age, body weight and symptoms. For example, in the case of intravenous administration, it is preferable to administer 1 to 25 mg/kg in terms of the amount of active ingredient, per day for an adult, and in the case of oral administration, it is preferable to administer 2 to 200 mg/kg, in terms of the amount of active ingredient, per day for an adult. The time for administration may be arbitrarily determined in accordance with the age and symptoms.

EXAMPLES

Hereinafter, the invention will be described by way of Examples, but the invention is not intended to be limited thereto. Further, the term "%" in the Examples is based on mass/volume, unless stated otherwise.

Example 1

Spores of *Stachybotrys microspora* strain IFO30018 were inoculated into a conical flask having a capacity of 500 ml, in which 100 ml of a medium for seed culture was contained, and seed culture was performed for 4 days at 25° C. and 180 rpm using a rotary shaker. The medium for seed culture used was prepared by dissolving glucose (4%), soybean meal (0.5%), dried bouillon (0.3%) and powdered yeast extract (0.3%) in water, adjusting the solution to pH 5.8 using HCl, adding a defoaming agent CB442 (0.01%) (Nippon Oil & Fats Co., Ltd., Japan), dividing the mixture in an amount of 100 ml each in an incubator, and then autoclaving the resultant (121° C., 15 min).

5 ml of this culture solution was inoculated into a conical flask having a capacity of 500 ml, in which 100 ml of a main culture medium was contained, and main culture was performed for 4 days at 25° C. and 180 rpm using a rotary shaker. The medium for the main culture (restricted medium) used was prepared by dissolving sucrose (5%), powdered yeast extract (0.1%), $NaNO_3$ (0.3%), $K_2HPO_4$ (0.1%), $MgSO_4.7H_2O$ (0.05%), KCl (0.05%), $CoCl_2.6H_2O$ (0.00025%), $FeSO_4.7H_2O$ (0.0015%) and $CaCl_2.2H_2O$ (0.00065%) in water, adjusting the solution to pH 5.8 using HCl, adding a defoaming agent CB442 (0.01%) (Nippon Oil & Fats Co., Ltd., Japan), dividing the mixture in an amount of 100 ml each in an incubator, and then autoclaving the resultant (121° C., 15 min).

The day that inoculation was performed was counted as day 0 of the culture, and on day 4 of the culture (after 96 hours), 100 mg of ammonium chloride was added to the medium (production medium), and the culture was continued. On day 5 of the culture, 200 ml of methanol was added to terminate the culture. Thereafter, extraction was performed by shaking at 180 rpm and 25° C. over about 3 hours, using a rotary shaker.

Example 2

From 300 ml of the culture extract of Example 1, the fungal cells were removed using a Buechner funnel, to obtain a culture supernatant. Concentration was performed under reduced pressure attained by a vacuum pump, using a rotary evaporator. At the time point where the residual amount reached about 50 ml, concentration was stopped. The concentrate was extracted three times with an equal amount of ethyl acetate, dehydrated over anhydrous sodium sulfate, filtered, concentrated and dried to solids. The dried solids were dissolved in about 3 ml of MeOH, and then the solution was filtered.

Then, this was centrifuged at 3000 rpm for 10 minutes. Before performing fractionation by HPLC, the supernatant was subjected to a pre-treatment with Lichrolut (registered trademark) RP-18 (100 mg) (MERCK KGaA, Darmstadt, Germany). Reverse phase HPLC was performed under the conditions of column: Inertsil PREP-ODS (diameter 30×250 mm) (GL Sciences, Inc., Tokyo, Japan), temperature: 40° C., flow rate: 25 ml/min, detection wavelength: 260 nm, and developing solvent: 75% methanol containing 50 mM ammonium acetate, and a peak was fractionated at a retention time of 11.5 minutes (see FIG. 2). Methanol was distilled off using a rotary evaporator, and the residue was extracted three times with an equal amount of ethyl acetate, dehydrated over anhydrous sodium sulfate, filtered, and then concentrated. This was dissolved in methanol, filtered, concentrated and dried to obtain 33.23 mg of a purified product. Yield about 30% (mass/mass).

Example 3

The physicochemical properties of the white solid compound (designated as SMTP-0) obtained in Example 2 were examined.

In addition, as a control of the compound of the present Example, Stachybotrin B (having a positive (+) optical rotation) shown below was used. For the structure of Stachybotrin B, J. Org. Chem., (1992), vol. 57, pp. 6700-6703 was referred to. (However, since the absolute stereostructure has not been determined, the structure shown below is a relative configuration.)

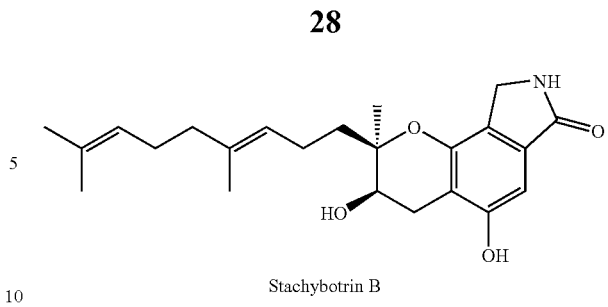

Stachybotrin B

NMR was measured using an ALPHA600 (JEOL, Ltd.) under the conditions of $^1$H 600 MHz, $^{13}$C 150 MHz and 50° C. The sample used was a solution of about 10 mg/ml of DMSO-$d_6$.

MALDI-TOF-MS was measured using a Voyager-DE STR (Applied Biosystems, Inc.) in the positive ion mode, using α-cyano-4-hydroxycinnamic acid as the matrix.

For UV spectroscopy, a 320 Spectrophotometer (Hitachi, Ltd.) was used. The sample was dissolved in MeOH (5 µg/ml).

For FT-IR, a JIR WINSPEC50 (JEOL, Ltd.) was used. 750 µg of a sample dissolved in MeOH was applied on rock salt and measured.

For the optical rotation, a DIP-360 (JASCO Corp.) was used (27° C., Na). The sample was dissolved in MeOH (10 mg/ml).

Figure 2:
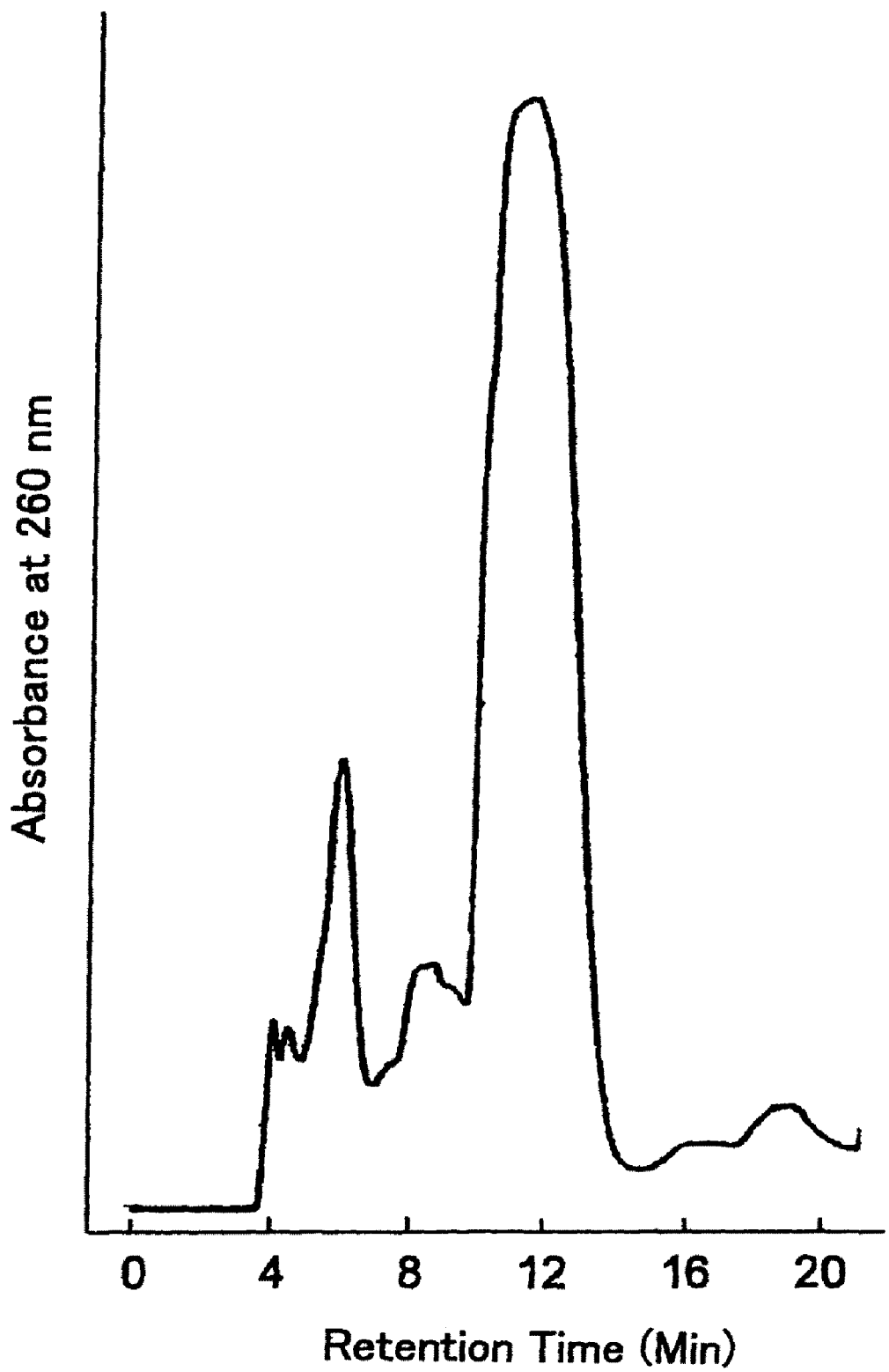
FIG. 2 is a chromatographic chart according to Example 1 of the invention.

The results are presented in FIG. 2 and Table 1.

The physicochemical properties of SMTP-0 obtained in Example 2 are as follows.

External appearance: White solid

Molecular formula: $C_{23}H_{31}NO_4$

MALDI-TOF-MS (M+H)$^+$: 386.2599

Theoretical value: 386. 2331($C_{23}H_{32}NO_4$)

UV λmax (ε) MeOH:

215 (ε 55,769), 251 (ε 10,615), 300 (ε 4,000)

IR spectrum ν (cm$^{-1}$):

3259.15, 2917.81, 1666.22, 1612.22, 1469.51, 1359.59, 1166.74, 1081.88, 850.46, 773.32, 723.18, 674.97, 566.98,

Specific optical rotation $[α]_D^{27}$=−2.23° (c 1.0, MeOH)

TABLE 1

|  | SMTP-0 | | | Stachybotrin B | | |
|---|---|---|---|---|---|---|
|  | δ C | δ H | | δ C | δ H | |
| 2 | 170.24 | | | 174.20 | | |
| 3 | 131.78 | | | 132.50 | | |
| 4 | 99.44 | 6.62 1H, s | | 100.80 | 6.74 s | |
| 5 | 155.93 | | | 158.00 | | |
| 6 | 111.29 | | | 113.50 | | |
| 7 | 26.59 | 2.82 1H, dd | J = 5.5, 17.4 | 27.80 | 2.98 dd | J = 18.0, 6.0 |
|  |  | 2.45 1H, dd | J = 7.7, 17.6 |  | 2.64 dd | J = 18.0, 6.0 |
| 8 | 66.01 | 3.73 1H, t | J = 6.4 | 68.40 | 3.87 dd | J = 6.0, 6.0 |
| 9 | 78.52 | | | 80.20 | | |
| 11 | 148.45 | | | 150.20 | | |
| 12 | 121.61 | | | 124.10 | | |
| 13 | 41.95 | 4.09 1H, d | J = 17.2 | 44.20 | 4.20 d | J = 18.0 |
|  |  | 4.05 1H, d | J = 16.9 |  | 4.23 d | J = 18.0 |
| 14 | 37.14 | 1.59 2H, m | | 38.50 | 1.67 2H, m | |
| 15 | 20.93 | 2.10 2H, m | | 22.60 | 2.18 2H, m | |
| 16 | 124.16 | 5.11 1H, t | J = 6.6 | 125.50 | 5.14 1H, m | |
| 17 | 134.18 | | | 136.20 | | |
| 18 | 39.04 | 1.91 2H, m | | 40.80 | 1.95 2H, m | |

TABLE 1-continued

| | | | | | | | | |
|---|---|---|---|---|---|---|---|---|
| 19 | 26.06 | 1.99 | 2H, m | | 27.80 | 2.02 | 2H, m | |
| 20 | 123.98 | 5.04 | 1H, t | J = 7.1 | 125.30 | 5.05 | 1H, m | |
| 21 | 130.52 | | | | 132.20 | | | |
| 22 | 25.27 | 1.61 | 3H, s | | 25.80 | 1.63 | s | |
| 23 | 17.36 | 1.53 | 3H, s | | 17.70 | 1.55 | s | |
| 24 | 15.48 | 1.54 | 3H, s | | 15.67 | 1.57 | s | |
| 25 | 17.95 | 1.15 | 3H, s | | 18.22 | 1.27 | s | |

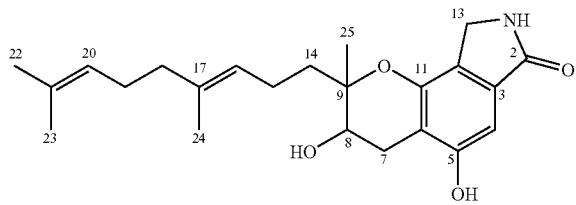

From these results, it was suggested that SMTP-0 obtained in Example 2 has the same planar structure as that of Stachybotrin B (see the aforementioned Non-Patent Document 1). However, while SMTP-0 has a negative (−) optical rotation, Stachybotrin B had a positive (+) optical rotation. As such, SMTP-0 of the present Example as shown below has a stereostructure that is clearly different from that of Stachybotrin B.

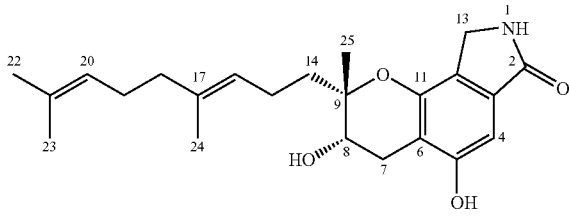

Example 4

In order to clarify the details of differences in the stereostructure between SMTP-0 and Stachybotrin B as found in Example 3, an analysis using a modified Mosher's method was performed.

SMTP-0 (50 mg, 78 μmol) was dissolved in acetonitrile (2 mL), and N,N-diisopropylethylamine (50 μl) and trimethylsilyldiazomethane (2.0 M, hexane solution) (150 μl) were added thereto. The mixture was stirred for 24 hours at room temperature. The reaction liquid was concentrated to obtain methyl ether of SMTP-0 (SMTP-0-OMe) (44 mg). SMTP-0-OMe (20 mg, 50 μmol) was dissolved in N,N-dimethylformamide (1 mL), and R-(−)-α-methoxy-α-(trifluoromethyl) phenylacetyl chloride (25 mg), triethylamine (30 μl) and 4-dimethylaminopyridine (2 mg) were added thereto. The mixture was stirred for 24 hours at room temperature. Water (10 mL) was added to the reaction liquid, and the mixture was extracted with ethyl acetate (50 mL). The organic layer was washed with 1 N HCl, a saturated aqueous solution of sodium hydrogen carbonate and saturated brine, then dried using anhydrous magnesium sulfate, and concentrated under reduced pressure. The residue was purified by thin layer chromatography (hexane-ethyl acetate), to obtain SMTP-0-OMe ester of S-α-methoxy-α-(trifluoromethyl)phenylacetylacetic acid (S-MTPA-SMTP-0-OMe) (18 mg).

SMTP-OMe ester of R-α-methoxy-α-(trifluoromethyl) phenylacetylacetic acid (R-MTPA-SMTP-0-OMe) (17 mg) was obtained from SMTP-0-OMe (20 mg, 50 μmol), by performing the same reaction as described above using S-(+)-α-methoxy-α-(trifluoromethyl)phenylacetyl chloride instead of R-(−)-α-methoxy-α-(trifluoromethyl)phenylacetyl chloride.

Various nuclear magnetic resonance spectra were measured for R-MTPA-SMTP-0-OMe and S-MTPA-SMTP-0-OMe obtained by the above-described methods, and proton assignment was performed for the respective compounds. The results are presented in Table 2.

The difference between the chemical shift of S-MTPA-SMTP-0-OMe, $\delta S$, and the chemical shift of R-MTPA-SMTP-0-OMe, $\delta R$ ($\Delta\delta=\delta S-\delta R$), was calculated. As a result, a of the proton at the axial position of the 7-position had a negative value ($\Delta\delta=-0.12$), and $\Delta\delta$ of the proton of the methyl group at the 25-position had a positive value ($\Delta\delta=+0.03$). Thus, the absolute configuration of SMTP-0- of the invention was determined to have an absolute configuration as shown in the Example 3 (configurations of the 8-position and the 9-position are both S).

TABLE 2

Assignment of NMR spectra of SMTP-0-OMe, R-MTPA-SMTP-0-OMe and S-MTPA-SMTP-0-OMe

| Position | SMTP-0-OMe | | R-MTPA-SMTP-0-OMe | | S-MTPA-SMTP-0-OMe | |
|---|---|---|---|---|---|---|
| | H | J (Hz) | H | J (Hz) | H | J (Hz) |
| 4 | 6.91 1H, s | | 6.90 1H, s | | 6.94 1H, s | |
| 7 | 2.98 1H, dd | 5.1, 17.6 | 3.16 1H, dd | 5.3, 18.0 | 3.16 1H, dd | 5.1, 18.0 |
| | 2.77 1H, dd | 5.5, 18.0 | 2.76 1H, dd | 6.6, 18.0 | 2.88 1H, dd | 5.9, 18.0 |
| 8 | 3.94 1H, dd | 5.1, 8.6 | 5.29 1H, dd | 5.5, 6.2 | 5.28 1H, t | 5.5 |
| 13 | 4.32 1H, d | 17.2 | 4.27 2H, s | | 4.28 2H, s | |
| | 4.28 1H, d | 16.9 | | | | |

TABLE 2-continued

Assignment of NMR spectra of SMTP-0-OMe,
R-MTPA-SMTP-0-OMe and S-MTPA-SMTP-0-OMe

| | SMTP-0-OMe | | R-MTPA-SMTP-0-OMe | | S-MTPA-SMTP-0-OMe | |
|---|---|---|---|---|---|---|
| Position | H | J (Hz) | H | J (Hz) | H | J (Hz) |
| 14 | 1.65 2H, m | | 1.64 2H, m | | 1.63 2H, m | |
| 15 | 2.14 2H, m | | 2.12 2H, m | | 2.11 2H, m | |
| 16 | 5.10 1H, t | 7.0 | 5.07 1H, m | | 5.07 1H, t | 7.0 |
| 18 | 1.96 2H, m | | 1.96 2H, t | 7.7 | 1.96 2H, t | 7.7 |
| 19 | 2.04 2H, m | | 2.05 2H, m | | 2.04 2H, m | |
| 20 | 5.07 1H, t | 7.0 | 5.06 1H, m | | 5.02 1H, t | 7.0 |
| 22 | 1.67 3H, s | | 1.67 3H, s | | 1.67 3H, s | |
| 23 | 1.57 3H, s | | 1.57 3H, s | | 1.56 3H, s | |
| 24 | 1.58 3H, s | | 1.59 3H, s | | 1.58 3H, s | |
| 25 | 1.37 3H, s | | 1.28 3H, s | | 1.23 3H, s | |
| 5-OMe | 3.87 3H, s | | 3.86 3H, s | | 3.87 3H, s | |
| MTPA moiety | | | 3.45 3H, s | | 3.49 3H, s | |
| | | | 7.36 3H, m | | 7.30 1H, t | 7.7 |
| | | | 7.48 2H, d | 7.7 | 7.36 1H, t | 7.3 |
| | | | | | 7.43 2H, d | 7.7 |

Example 5

The fibrinolysis enhancing activity of SMTP-0 (50 μM, 100 μM and 200 μM) obtained in Example 2 was evaluated as follows, as the activity for promoting the plasminogen activation by urokinase catalysis.

A 30 mM solution of SMTP (DMSO solution) was diluted with TBS/T (50 mM Tris-HCl, 100 mM NaCl and 0.01% Tween80, pH 7.4) to prepare a 1.5 mM solution (in 5% DMSO·TBS/T). This solution was diluted with 5% DMSO in TBS/T to prepare SMTP solutions at the concentrations mentioned above.

(1) Measurement of Activity of Plasminogen Fragment Production

An SMTP solution (60 μl) was mixed with 240 μl of a reaction liquid at a 1.25-fold concentration (not containing VLK-pNA (Val-Leu-Lys-p-nitroanilide)), and the mixture was allowed to react for 60 minutes at 37° C. Then, 75 μl of 50% trichloroacetic acid (TCA) was added to terminate the reaction, and the mixture was left to stand in ice for 60 minutes. TCA-insoluble materials were precipitated by centrifugation, and the precipitate was washed two times with acetone. The obtained precipitate was dried, and then dissolved with 11 μl of added SDS sample buffer (0.125 M Tris-Cl, pH 6.8, 4% SDS, 20% glycerol and 0.02% bromophenol blue). 10 μl of the solution was used to perform SDS polyacrylamide gel electrophoresis (10% gel). The results are presented in FIG. 3.

(2) Measurement of Plasminogen Activation

10 μl of an SMTP solution (10 μl) was mixed with 40 μl of a reaction liquid at a 1.25-fold concentration (0.0625 μM of plasminogen, 62.5 U/ml of urokinase, and 0.125 mM of VLK-pNA) in a 96-well microplate, and measurement was made by immediately monitoring the absorption of the hydrolysis of VLK-pNA at 405 nm over time with a microplate reader. The measurement was performed at 37° C. for 60 minutes at an interval of 2 minutes. The results are presented in FIG. 4.

Figure 3:
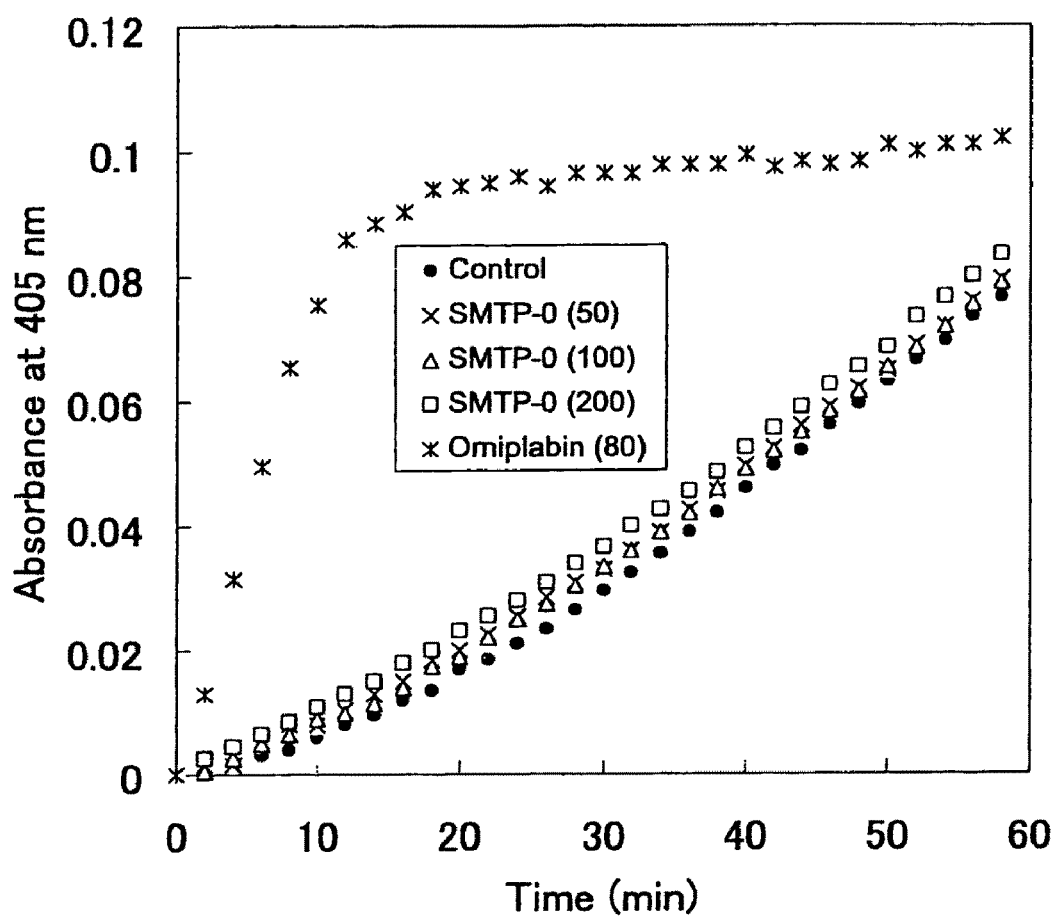
FIG. 3 is a graph showing the effect of SMTP-0 and orniplabin (SMTP-7) on plasminogen activation according to Example 5 of the invention (the unit of concentration in the legend is μM).
Figure 4:
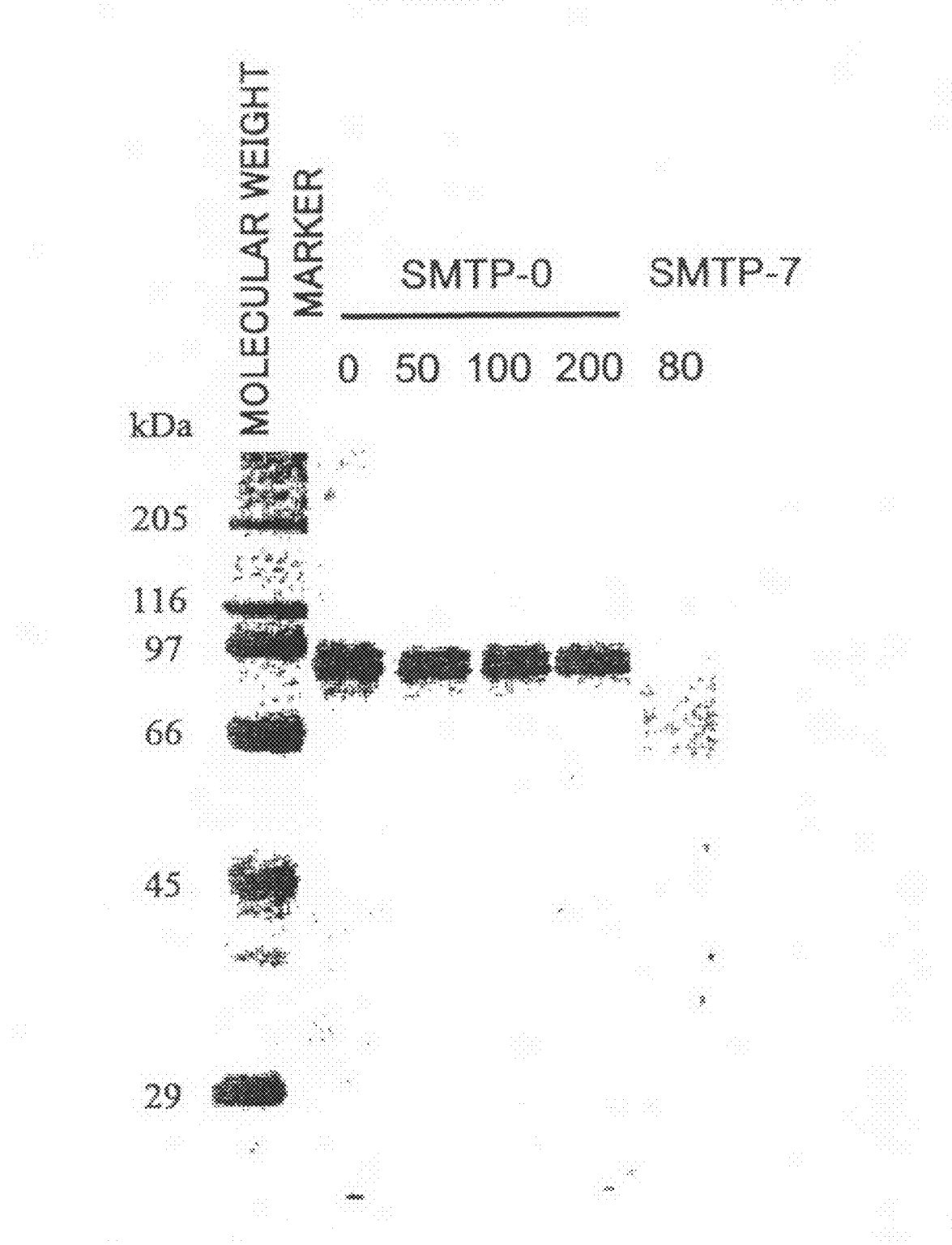
FIG. 4 is a graph showing the effect of SMTP-0 and orniplabin (SMTP-7) on the generation of plasminogen fragments according to Example 5 of the invention (the unit of concentration is μM).

As shown in FIG. 3 and FIG. 4, the results did not indicate any action of enhancing the plasminogen activation at any concentration (see FIG. 3). Furthermore, the compound did not exhibit any action on the generation of plasminogen fragments having the angiogenesis inhibitory activity (see FIG. 4).

When the secondary amine of such SMTP-0 is modified with an amino acid such as D-tryptophan, an active triprenyl phenol compound exhibiting a strong plasminogen activation enhancing action can be obtained.

In the present Example, an intermediate triprenyl phenol compound capable of easily inducing an active triprenyl phenol compound could be provided.

Thereby, an active triprenyl phenol compound which is stable and cannot be produced by a fermentation method, can be obtained.

Example 6

The time for addition of an amine compound was examined as follows.

The medium for main culture (restricted medium) used was prepared by dissolving sucrose (5%), $NaNO_3$ (0.3%), $K_2HPO_4$ (0.1%), $MgSO_4 \cdot 7H_2O$ (0.05%) and KCl (0.05%) in water, adjusting the solution to pH 5.8 using HCl, adding a defoaming agent CB442 (0.01%) (Nippon Oil & Fats Co., Ltd., Japan), dividing the mixture in an amount of 100 ml each in an incubator, and autoclaving (121° C., 15 min). The culture was performed in the same manner as in Example 1.

24 hours, 48 hours, 72 hours, 96 hours and 120 hours after the initiation of culture, respectively, L-cystine (0.3%) was added as an amine compound, and then the system was incubated for 24 hours, after which the quantity of production was measured. For the measurement of the quantity of production, a double amount of methanol was added to the culture solution, the mixture was shaken for 1 hour, an SMTP compound was extracted, the extract was centrifuged at 10,000 rpm to separate the supernatant, and this supernatant was used. 0.01 ml of this supernatant was subjected to high performance liquid chromatography using a Silica ODS column, and while developing with 80% methanol containing 50 mM ammonium acetate at a flow rate of 1 ml/min, the absorbance at 260 nm was monitored. Quantification was performed by comparing the peak area of the sample corresponding to the retention time of the standard sample, with the peak area of the standard sample.

The results are presented in Table 3.

TABLE 3

| Time of addition of L-cystine (Time after the initiation of productive culture) | Accumulated amount of SMTP-9 mg/ml |
|---|---|
| 24 | 0.14 |
| 48 | 0.04 |
| 72 | 0.67 |
| 96 | 0.34 |
| 120 | 0.30 |

As shown in Table 3, the quantity of production of SMTP increased by performing the culture using a production medium containing an amino acid, not immediately after the initiation of culture using a restricted culture which contains no amine compound, but after certain period of time. In particular, when an amino acid was added not during the early phase of culture after the initiation of the culture using a restricted medium, but after 72 hours, that is, at the intermediate stage of culture, the quantity of production of SMTP-9 increased by a large extent.

As a Comparative Example, SMTP-9 was obtained by adding L-cystine to a medium in which the amount and type of the amine compound were not restricted, during the early phase of culture (see JP-A Nos. 2002-65288 and 2004-224737). However, as compared to the production method used in the present Example, the quantity of production was about 0.1 mg/ml at the maximum, which was 15% or less of the amount of the present method. Furthermore, according to this conventional method, in particular, when an amino acid or amino alcohol was added after 5 days from the initiation of culture, the production of the product was greatly decreased, whereas in the present Example, a high amount of production could be maintained even by the addition after 5 days.

Therefore, the production method of the present Example can produce the SMTP compound efficiently.

Example 7

Next, inorganic salts that can be added to the restricted medium and the production medium were examined as follows.

As for the medium for main culture (restricted medium), glucose (2%), NaNO$_3$ (0.3%), K$_2$HPO$_4$ (0.1%), MgSO$_4$.7H$_2$O (0.05%), KCl (0.05%) and FeSO$_4$.7H$_2$O (0.001%) were dissolved in water, the solution was adjusted to pH 5.8 using HCl, a defoaming agent CB442 (0.01%) (Nippon Oil & Fats Co., Ltd., Japan) was added, the mixture divided in an amount of 100 ml each in an incubator, and autoclaving (121° C., 15 min) was performed to obtain a medium (D medium). This medium was used as the basic medium, and the components and concentration were changed as described in Table 4. Culture was performed in the same manner as in Example 1 using these media.

L-cystine (0.1%) as an amine compound was added to the culture 72 hours after the initiation of culture, and then the culture was incubated for 48 hours. The quantity of production was measured by the method described in Example 6.

The results are presented in Table 4.

TABLE 4

| Changed or added medium component | Concentration (%) | Component excluded from D medium | Accumulated amount of SMTP-9 (mg/ml) |
|---|---|---|---|
| Sodium nitrate | 0.1 | | 0.08 |
| | 0.3 | | 0.10 |
| | 0.5 | | 0.14 |
| Potassium nitrate | 0.1 | Sodium nitrate | 0.06 |
| | 0.3 | | 0.18 |
| | 0.5 | | 0.26 |
| Ferrous sulfate heptahydrate | 0.005 | | 0.43 |
| | 0.01 | | 0.26 |
| | 0.05 | | 0.38 |
| Potassium phosphate, monobasic | 0.025 | Potassium phosphate, dibasic | 0.06 |
| | 0.25 | | 0.31 |
| | 0.5 | | 0.05 |
| Potassium phosphate, dibasic | 0.025 | | 0.02 |
| | 0.25 | | 0.02 |
| | 0.5 | | 0.02 |
| Calcium chloride dehydrate | 0.01 | | 0.10 |
| | 0.05 | | 0.31 |
| | 0.1 | | 0.27 |
| Cobalt chloride hexahydrate | 0.001 | | 0.40 |
| | 0.005 | | 0.20 |
| | 0.01 | | 0.04 |
| Magnesium sulfate | 0.1 | | 0.40 |
| | 0.2 | | 0.16 |
| | 0.3 | | 0.18 |
| Potassium chloride | 0.1 | | 0.30 |
| | 0.25 | | 0.03 |
| | 0.5 | | 0.03 |

Example 8

Furthermore, examination of the concentrations of metal salt, carbon source, sodium nitrate and an amine to be added (L-cystine in the following Example) was performed as follows.

As for the medium for main culture (restricted medium), sucrose (5%), peptone (0.1%), NaNO$_3$ (0.3%), K$_2$HPO$_4$ (0.1%), MgSO$_4$.7H$_2$O (0.05%) and KCl (0.05%) were dissolved in water, the solution was adjusted to pH 5.8 using HCl, a defoaming agent CB442 (0.01%) (Nippon Oil & Fats Co., Ltd., Japan) was added, the mixture divided in an amount of 100 ml each in an incubator, and autoclaving (121° C., 15 min) was performed to obtain a medium (F medium). This medium was used as the basic medium, and the components and concentration were changed as described in Table 5. Culture was performed in the same manner as in Example 1 using these media.

L-cystine (in the amount described in Table 5) as an amine compound was added to the culture 72 hours after the initiation of culture, and then the culture was incubated for 24 hours, 48 hours and 72 hours, respectively. The quantity of production was measured by the method described in Example 6.

The results are presented in Table 5.

TABLE 5

| Calcium chloride dehydrate (%) | Ferrous sulfate heptahydrate (%) | Cobalt chloride hexahydrate (%) | Changed or added medium component | Concentration (%) | Component excluded from F medium | Amount of addition of L-cystine (%) | Accumulated amount of SMTP-9 (mg/ml) | | |
|---|---|---|---|---|---|---|---|---|---|
| | | | | | | | After 24 hours | After 48 hours | After 72 hours |
| 0.00065 | 0.005 | 0.0005 | | | | 0.1 | 0.43 | 0.53 | 0.46 |
| 0.00065 | 0.005 | 0.0005 | | | | 0.3 | 0.21 | 0.25 | 0.28 |
| 0.00065 | 0.005 | 0.0005 | | | | 0.5 | 0.63 | 0.92 | 0.85 |
| 0.00065 | 0.005 | 0.0005 | | | | 1 | 0.55 | 0.85 | 0.85 |
| 0.00065 | 0.0015 | 0.00025 | | | | 0.1 | 0.31 | 0.32 | 0.30 |
| 0.00065 | 0.0015 | 0.00025 | Sodium nitrate | 0.7 | | 0.1 | 0.48 | 0.88 | 0.93 |
| 0.00065 | 0.0015 | 0.00025 | | | | 0.3 | 0.67 | 0.98 | 1.01 |
| 0.00065 | 0.005 | 0.0005 | Sucrose | 10 | | 0.3 | 0.70 | 1.01 | 1.01 |
| 0.00065 | 0.005 | 0.0005 | Sucrose | 10 | | 0.5 | 0.70 | 1.43 | 1.75 |
| 0.00065 | 0.005 | 0.0005 | Sucrose Sodium nitrate | 10 0.7 | | 0.5 | 0.69 | 1.04 | 1.05 |
| 0.00065 | 0.005 | 0.0005 | Glucose | 5 | Sucrose | 0.1 | 0.32 | 0.35 | 0.37 |
| 0.00065 | 0.005 | 0.0005 | Glucose | 5 | Sucrose | 0.3 | 0.48 | 0.71 | 0.67 |
| 0.00065 | 0.0015 | 0.00025 | Glucose | 5 | Sucrose | 0.1 | 0.36 | 0.34 | 0.34 |
| 0.00065 | 0.0015 | 0.00025 | Glucose | 5 | Sucrose | 0.3 | 0.57 | 0.93 | 0.97 |

As can be seen from these results, when a medium containing sucrose as the carbon source, yeast extract and sodium nitrate as the nitrogen sources, and dibasic potassium phosphate, magnesium sulfate, potassium chloride, ferrous sulfate, calcium chloride and cobalt chloride as the inorganic salts, was used, the quantity of production of SMTP-9 increased over 10-fold (from 0.08 mg/ml to 1 mg/ml or more) the quantity of production obtained by the method described in JP-A No. 2004-224737 (culture is initiated in 100 ml of a medium containing 2% of glucose, 0.5% of peptone, 0.3% of yeast extract, 0.3% of $K_2HPO_4$, 0.01% of $MgSO_4.7H_2O$ and 100 mg of L-cystine). Furthermore, L-cystine (0.5%) as the amine compound was added after 24 hours, 48 hours, 72 hours, 96 hours and 120 hours, respectively, of culturing in the restricted medium (F medium), subsequently the systems were incubated for 48 hours, and the quantities of production were measured. In this case, the quantities of production of SMTP-9 were 0.55, 0.70 0.92, 1.21 and 1.15 mg/ml, respectively.

In order to examine the production of compounds other than SMTP-9, a culture was performed using the restricted medium and production medium used in Example 1 and using 1 mg/ml of ornithine (the time of addition of ornithine was on day 4 of the culture), and a culture was performed, as a Comparative Example, using a medium containing the basic medium described in JP-A No. 2002-65288 (obtained by dissolving glucose (2%), 0.5% of peptone, 0.3% of yeast extract, $K_2HPO_4$ (0.3%) and $MgSO_4.7H_2O$ (0.01%) in water, and adjusting the solution to pH 5.5 using HCl or NaOH). The quantities of production were compared. As a result, the quantity of production of SMTP-7 increased to about fivefolds (from 0.3 mg/ml to 1.5 mg/ml).

From these results, it was found that in order to obtain SMTP compounds efficiently, it is preferable that the restricted medium and production medium contain predetermined inorganic salts, in the case of producing SMTP compounds by performing the culturing process using production medium containing an amine compound, which commences at an intermediate stage following the initiation of the culture using a restricted medium.

Example 9

Synthesis of compound I-1

Spores of *Stachybotrys microspora* strain IFO30018 (Institute for Fermentation, Osaka) were inoculated into a conical flask having a capacity of 500 ml, in which 100 ml of a medium for seed culture was contained, and seed culture was performed for 4 days at 25° C. and 180 rpm using a rotary shaker. The medium for seed culture used was prepared by dissolving glucose (4%), soybean meal (0.5%), dried bouillon (0.3%) and powdered yeast extract (0.3%) in water, adjusting the solution to pH 5.8 using HCl, adding a defoaming agent CB442 (0.01%) (1 ml/L of a 0.1 g/ml acetone solution was added) (Nippon Oil & Fats Co., Ltd.), dividing the mixture in an amount of 100 ml each in an incubator, and then autoclaving the resultant (121° C., 15 min).

5 nil of this culture solution was inoculated into a conical flask having a capacity of 500 ml, in which 100 ml of a main culture medium was contained, and main culture was performed for 5 days at 25° C. and 180 rpm using a rotary shaker. The medium for the main culture (restricted medium) used was prepared by dissolving sucrose (5%), powdered yeast extract (0.1%), $NaNO_3$ (0.3%), $K_2HPO_4$ (0.1%), $MgSO_4.7H_2O$ (0.05%), KCl (0.05%), $CoCl_2.6H_2O$ (0.00025%), $FeSO_4.7H_2O$ (0.0015%) and $CaCl_2.2H_2O$ (0.00065%) in water, adjusting the solution to pH 5.8 using HCl, adding a defoaming agent CB442 (0.01%) (1 ml/L of a 0.1 g/ml acetone solution was added) (Nippon Oil & Fats Co., Ltd.), dividing the mixture in an amount of 100 ml each in an incubator, and then autoclaving the resultant (121° C., 15 min).

The day that inoculation was performed was counted as day 0 of the culture, and on day 4 of the culture (after 96 hours), 100 mg of p-aminophenol was added to the medium to provide a production medium, and the culture was continued. After about 24 hours, 200 ml of methanol was added to terminate the culture. Thereafter, extraction was performed by shaking at 180 rpm and 25° C. over about 3 hours, using a rotary shaker.

From 300 ml of the culture extract obtained, the fungal cells were removed using a Buechner funnel, to obtain a culture supernatant. Concentration was performed under reduced pressure attained by a vacuum pump, using a rotary evaporator. At the time point where the residual amount reached about 100 ml or less, concentration was stopped, and the concentrate was adjusted to pH 2 using phosphoric acid, and left to stand overnight in a cold chamber. A precipitate generated therein was separated by centrifugation, and this precipitate was dissolved in acetone. This acetone suspension was centrifuged, and the supernatant was separated, concentrated and dried to solids, to obtain 324.1 mg of a dried solid product. MeOH was added to this dried solid product to obtain a 100 mg/ml solution, and this solution was centrifuged at 3000 rpm for 10 minutes. Before performing fractionation by HPLC, this supernatant was subjected to a pre-treatment with Lichrolut (registered trademark) RP-18 (100 mg) (MERCK KGaA, Darmstadt, Germany). Reverse phase HPLC was performed under the conditions of column: Inertsil PREP-ODS (diameter 30×250 mm) (GL Sciences, Inc., Tokyo, Japan), temperature: 40° C., flow rate: 25 ml/min, detection wavelength: 260 nm, and developing solvent: 80% methanol containing 50 mM ammonium acetate, and a peak was fractionated at a retention time of 16 to 17 minutes. Methanol was distilled off using a rotary evaporator, and the residue was extracted three times with an equal amount of ethyl acetate, dehydrated over anhydrous sodium sulfate, filtered, and then concentrated. This was dissolved in methanol, filtered, concentrated and dried to obtain 99.33 mg of a purified product of compound I-1.

The properties of the compound I-1 were determined as follows.

MALDI-TOF-MS was measured using a Voyager-DE STR (Applied Biosystems, Inc.) in the positive ion mode, using α-cyano-4-hydroxycinnamic acid as the matrix.

UV was measured using a 320 Spectrophotometer (Hitachi, Ltd.) in methanol.

FT-IR was measured using a JIR-WINSPEC50 (JEOL, Ltd.). A sample dissolved in acetone was applied on rock salt, and measured.

The physicochemical properties of the compound I-1 are presented in the following.

Molecular formula: $C_{29}H_{35}NO_5$
MALDI-TOF-MS (m/z)
Found (M+H)$^+$: 478.4473.
Calculated: 478.2593 for $C_{29}H_{36}NO_5$.
UV λmax nm (ε): 214(sh)(84,000), 260(sh)(21,500), 291 (30,000)
IR νmax (NaCl) cm$^{-1}$: 3855, 3747, 3309, 2971, 2919, 2863, 1664, 1618, 1513, 1461, 1373, 1247, 1168, 1074, 943, 835, 765, 684

Example 10

Synthesis of Compound I-2

Preliminary culture was performed in the same manner as in Example 9.

Main culture was performed in the same manner as in Example 9, except that the organic amine compound added on day 4 of the main culture was changed to p-aminobenzoic acid.

From 300 ml of the culture extract obtained, the fungal cells were removed using a Buechner funnel, to obtain a culture supernatant. Concentration was performed under reduced pressure attained by a vacuum pump, using a rotary evaporator. At the time point where the residual amount reached about 100 ml or less, concentration was stopped, and the concentrate was adjusted to pH 2 using phosphoric acid, and left to stand overnight in a cold chamber. A precipitate generated therein was separated by centrifugation, and this precipitate was dissolved in acetone. This acetone suspension was centrifuged, and the supernatant was separated, concentrated and dried to solids, to obtain 603.3 mg of a dried solid product. MeOH was added to this dried solid product to obtain a 100 mg/ml solution, and this solution was centrifuged at 3000 rpm for 10 minutes. Before performing fractionation by HPLC, this supernatant was subjected to a pre-treatment with Lichrolut RP-18 (100 mg). Reverse phase HPLC was performed under the conditions of column: Inertsil PREP-ODS (diameter 30×250 mm), temperature: 40° C., flow rate: 25 ml/min, detection wavelength: 260 nm, and developing solvent: 70% methanol containing 50 mM ammonium acetate, and a peak was fractionated at a retention time of 21 to 22 minutes. Methanol was distilled off using a rotary evaporator, and the residue was extracted three times with an equal amount of ethyl acetate, dehydrated over anhydrous sodium sulfate, filtered, and then concentrated. This was dissolved in methanol, filtered, concentrated and dried to obtain 52.44 mg of a purified product of compound I-2.

The properties of the compound I-2 were determined as follows.

MALDI-TOF-MS, UV and FT-IR were measured in the same manner as in Example 9. NMR was measured using an ALPHA600 (JEOL, Ltd.) under the conditions of $^1$H 600 MHz, $^{13}$C 150 MHz and 60° C. The sample used was a solution of about 10 mg/ml of DMSO-$d_6$.

The physicochemical properties of the compound I-2 are presented in the following.

Molecular formula: $C_{30}H_{35}NO_6$
MALDI-TOF-MS (m/z)
Found (M+H)$^+$: 506.2778.
Calculated: 506.2543 for $C_{30}H_{36}NO_6$.
UV λmax nm (ε):296 (29,300)
IR νmax (NaCl) cm$^{-1}$: 3853, 3739, 3392, 2969, 2915, 2858, 1691, 1610, 1513, 1463, 1429, 1365, 1303, 1267, 1187, 1076, 939, 848, 779, 676, 551
NMR

TABLE 6

I-2: SMTP-19

| No. | $\delta_C$ | $\delta_H$ |
|---|---|---|
| 2 | 167.12 | |
| 3 | 131.09 | |
| 4 | 99.68 | 6.76 (1H, s) |
| 5 | 156.39 | |
| 6 | 112.90 | |
| 7 | 26.58 | 2.88 (1H, dd, J = 5.5, 17.6) |
| | | 2.53 (1H, dd, J = 7.3, 17.6) |

TABLE 6-continued

I-2: SMTP-19

| No. | $\delta_C$ | $\delta_H$ |
| --- | --- | --- |
| 8 | 65.83 | 3.79 (1H, dd, J = 5.5, 7.3) |
| 9 | 78.88 | |
| 11 | 148.29 | |
| 12 | 118.70 | |
| 13 | 47.53 | 4.73 (1H, d, J = 15.8) |
|  |  | 4.78 (1H, d, J = 15.8) |
| 14 | 37.02 | 1.66 (2H, dd, J = 7.5, 8.7) |
| 15 | 20.91 | 2.16 (2H, m) |
| 16 | 124.09 | 5.16 (1H, t, J = 7.0) |
| 17 | 134.13 | |
| 18 | 38.94 | 1.93 (2H, m) |
| 19 | 26.00 | 2.01 (2H, m) |
| 20 | 123.87 | 5.05 (1H, m) |
| 21 | 130.36 | |
| 22 | 25.07 | 1.60 (3H, s) |
| 23 | 17.19 | 1.52 (3H, s) |
| 24 | 15.45 | 1.57 (3H, s) |
| 25 | 18.00 | 1.22 (3H, s) |
| 26 | 142.82 | |
| 27, 31 | 117.79 | 7.98 (2H, dd, J = 1.8, 7.0) |
| 28, 30 | 129.90 | 7.95 (2H, dd, J = 1.8, 7.0) |
| 29 | 127.33 | |
| 32 | 167.38 | |

The chemical shift is relative to DMSO-$d_6$ ($\delta_C$ 39.5 ppm; $\delta_H$ 2.49 ppm). The coupling constant (J) is given in Hz.

Example 11

Synthesis of Compound I-3

Preliminary culture was performed in the same manner as in Example 10.

5 ml of this culture solution was inoculated into a conical flask having a capacity of 500 ml, in which 100 ml of a main culture medium was placed, and main culture was performed for 6 days at 25° C. and 180 rpm using a rotary shaker.

The medium for the main culture (restricted medium) used was prepared by dissolving sucrose (5%), powdered yeast extract (0.1%), $KNO_3$ (0.7%), $K_2HPO_4$ (1.5%), $MgSO_4·7H_2O$ (0.05%), KCl (0.05%), $CoCl_2·6H_2O$ (0.00025%), $FeSO_4·7H_2O$ (0.0015%) and $CaCl_2·2H_2O$ (0.00065%) in water, adjusting the solution to pH 5.8 using HCl, adding a defoaming agent CB442 (0.01%) (1 ml/L of a 0.1 g/ml acetone solution was added) (Nippon Oil & Fats Co., Ltd.), dividing the mixture in an amount of 100 ml each in an incubator, and then autoclaving the resultant (121° C., 15 min).

The day that inoculation was performed was counted as day 0 of the culture, and on day 4 of the culture (after 96 hours), 100 mg of m-aminobenzoic acid was added to the medium to provide a production medium, and the culture was continued. After about 40 hours, 200 ml of methanol was added to terminate the culture. Thereafter, extraction was performed by shaking at 180 rpm and 25° C. over about 2 hours, using a rotary shaker.

Crude purification was performed in the same manner as in Example 10, to obtain 223.1 mg of a dried solid product. MeOH was added to this dried solid product to obtain a 100 mg/ml solution, and the solution was subjected to a pretreatment in the same manner as in Example 10. Reverse phase HPLC was performed in the same manner as in Example 10, except for the developing conditions. For the developing solvent, methanol containing 50 mM ammonium acetate was used, and the methanol concentration was increased linearly from 70% to 90% over 30 minutes. A peak was fractionated at a retention time of 17.5 to 18.5 minutes. The obtained fraction was purified in the same manner as in Example 10, to obtain 40.36 mg of a purified product of compound I-3.

The properties of the compound I-3 were determined as follows.

MALDI-TOF-MS, UV and FT-IR were measured in the same manner as in Example 10. NMR was measured using an ALPHA600 (JEOL, Ltd.) under the conditions of $^1H$ 600 MHz, $^{13}C$ 150 MHz and 25° C. The sample used was a solution of about 10 mg/ml of acetone-$d_6$.

The physicochemical properties of the compound I-3 are presented in the following.

Molecular formula: $C_{30}H_{35}NO_6$
MALDI-TOF-MS (m/z)
Found (M+H)$^+$: 506.2573.
Calculated: 506.2543 for $C_{30}H_{36}NO_6$.
UV λmax nm (ε): 217 (46,786), 281 (17,583)
IR νmax (NaCl) cm$^{-1}$: 3352, 2970, 2920, 2858, 2634, 2540, 1693, 1616, 1593, 1462, 1367, 1290, 1244, 1155, 1072
NMR

TABLE 7

I-3: SMTP-20

| No. | $\delta_C$ | $\delta_H$ |
| --- | --- | --- |
| 2 | 168.26 | |
| 3 | 133.14 | |
| 4 | 100.86 | 6.84 (1H, s) |
| 5 | 157.45 | |
| 6 | 113.76 | |
| 7 | 27.75 | 3.05 (1H, dd, J = 5.4, 17.4) |
|  |  | 2.69 (1H, dd, J = 7.2, 17.4) |
| 8 | 67.67 | 3.98 (1H, dd, J = 5.4, 7.2) |
| 9 | 80.14 | |
| 11 | 149.87 | |
| 12 | 120.52 | |
| 13 | 48.61 | 4.81 (2H, s) |
| 14 | 38.44 | 1.76 (2H, m) |
| 15 | 22.23 | 2.25 (2H, m) |
| 16 | 125.31 | 5.19 (1H, t, J = 6.6) |
| 17 | 135.65 | |

TABLE 7-continued

I-3: SMTP-20

| No. | $\delta_C$ | $\delta_H$ |
|---|---|---|
| 18 | 40.44 | 1.96 (2H, m) |
| 19 | 27.39 | ~2.03 (2H, m) |
| 20 | 125.11 | 5.07 (1H, t, J = 6.6) |
| 21 | 131.66 | |
| 22 | 25.79 | 1.61 (3H, s) |
| 23 | 17.68 | 1.54 (3H, s) |
| 24 | 16.01 | 1.61 (3H, s) |
| 25 | 18.62 | 1.32 (3H, s) |
| 26 | 141.55 | |
| 27 | 120.58 | 8.60 (1H, s) |
| 28 | 132.34 | |
| 29 | 125.43 | 7.79 (1H, d, J = 7.2) |
| 30 | 129.85 | 7.52 (1H, t, J = 7.8) |
| 31 | 123.76 | 8.26 (1H, d, J = 7.8) |
| 32 | 167.62 | |

The chemical shift is relative to acetone-$d_6$ ($\delta_C$ 29.8 ppm [methyl carbon atom]; $\delta_H$ 2.04 ppm). The coupling constant (J) is given in Hz.

Example 12

Synthesis of Compound I-4

Preliminary culture was performed in the same manner as in Example 10.

Main culture was performed in the same manner as in Example 11, except that the organic amine compound added on day 4 of the main culture was changed to o-aminobenzoic acid.

Crude purification was performed in the same manner as in Example 10, to obtain 120 mg of a dried solid product. MeOH was added to this dried solid product to obtain a 100 mg/ml solution, and the solution was subjected to a pretreatment in the same manner as in Example 10. Reverse phase HPLC was performed in the same manner as in Example 10, except for the developing conditions. For the developing solvent, methanol containing 50 mM ammonium acetate was used, and the methanol concentration was increased linearly from 70% to 90% over 40 minutes. A peak was fractionated at a retention time of 22.8 to 23.8 minutes. The obtained fraction was purified in the same manner as in Example 10, to obtain 14.58 mg of a purified product of compound I-4.

The properties of the compound I-4 were determined as follows.

MALDI-TOF-MS, UV and FT-IR were measured in the same manner as in Example 9. NMR was measured in the same manner as in Example 11 at 40° C.

The physicochemical properties of the compound I-4 are presented in the following.

Molecular formula: $C_{30}H_{35}NO_6$
MALDI-TOF-MS (m/z)
Found (M+H): 506.2573.
Calculated: 506.2543 for $C_{30}H_{36}NO_6$.
UV λmax nm (ε):215 (sh) (48,908), 260 (13,440), 301 (sh) (5,255)
IR νmax (NaCl) cm$^{-1}$: 3398, 2970, 2920, 2860, 2630, 2488, 1707, 1612, 1466, 1369, 1240, 1159, 1078, 1036
NMR

TABLE 8

I-4: SMTP-21

| No. | $\delta_C$ | $\delta_H$ |
|---|---|---|
| 2 | 169.04 | |
| 3 | 132.94 | |
| 4 | 101.19 | 6.83 (1H, m) |
| 5 | 157.22 | |
| 6 | 113.15 | |
| 7 | 27.75 | 3.05 (1H, dd, J = 5.4, 17.4) |
| | | 2.69 (1H, dd, J = 7.8, 17.4) |
| 8 | 67.89 | 3.96 (1H, m) |
| 9 | 80.04 | |
| 11 | 149.78 | |
| 12 | 121.78 | |
| 13 | 51.01 | 4.70 (2H, s) |
| 14 | 38.66 | 1.76 (2H, m) |
| 15 | 22.28 | 2.24 (2H, m) |
| 16 | 125.36 | 5.19 (1H, t, J = 6.6) |
| 17 | 135.72 | |
| 18 | 40.48 | 1.97 (2H, m) |
| 19 | 27.48 | ~2.06 (2H, m) |
| 20 | 125.19 | 5.08 (1H, t, J = 6.6) |
| 21 | 131.69 | |
| 22 | 25.80 | 1.63 (3H, s) |
| 23 | 17.72 | 1.56 (3H, s) |
| 24 | 16.05 | 1.60 (3H, s) |
| 25 | 18.51 | 1.30 (3H, s) |
| 26 | 139.54 | |
| 27 | 130.85 | |
| 28 | 131.66 | 7.95 (1H, d, J = 7.2) |
| 29 | 127.80 | 7.44 (1H, t, J = 7.2) |
| 30 | 133.27 | 7.65 (1H, t, J = 7.8) |
| 31 | 128.88 | 7.53 (1H, d, J = 7.8) |
| 32 | 167.62 | |

The chemical shift is relative to acetone-$d_6$ ($\delta_C$ 29.8 ppm [methyl carbon atom]; $\delta_H$ 2.04 ppm). The coupling constant (J) is given in Hz.

Example 13

Synthesis of Compound I-5

Preliminary culture was performed in the same manner as in Example 10.

Main culture was performed in the same manner as in Example 11, except that the organic amine compound added on day 4 of the main culture was changed to 4-aminosalicylic acid.

Crude purification was performed in the same manner as in Example 10, to obtain 408 mg of a dried solid product. MeOH was added to this dried solid product to obtain a 150 mg/ml solution, and the solution was subjected to a pretreatment in the same manner as in Example 10. Reverse phase HPLC was performed in the same manner as in Example 10, except for the developing conditions. The detection wavelength was 290 nm. For the developing solvent, 70% methanol containing 50 mM ammonium acetate was used, and a peak was fractionated at a retention time of 12.7 to 15 minutes. The obtained fraction was purified in the same manner as in Example 10, to obtain 18.50 mg of a purified product of compound I-5.

The properties of the compound I-5 were determined as follows.

FAB-MS was measured using a JEOL SX-102A in the positive ion mode using glycerol as the matrix. UV, FT-IR and NMR were measured in the same manner as in Example 11.

The physicochemical properties of the compound I-5 are presented in the following.

Molecular formula: $C_{30}H_{35}NO_7$
MALDI-TOF-MS (m/z)
Found $(M+H)^+$: 522.
Calculated: 522.2492 for $C_{30}H_{36}NO_7$.
UV λmax nm (ε):212 (sh) (47,641), 288 (18,973), 306 (18,243)
IR νmax (NaCl) $cm^{-1}$: 3398, 2968, 2922, 2860, 2553, 1689, 1622, 1462, 1362, 1253, 1218, 1157, 1074
NMR

TABLE 9

I-5: SMTP-22

| No. | $\delta_C$ | $\delta_H$ |
|---|---|---|
| 2 | 168.67 | |
| 3 | 132.78 | |
| 4 | 100.77 | 6.85 (1H, s) |
| 5 | 157.49 | |
| 6 | 114.18 | |
| 7 | 27.70 | 3.04 (1H, dd, J = 5.5, 17.6) |
| | | 2.69 (1H, dd, J = 7.7, 17.6) |
| 8 | 67.56 | 3.97 (1H, dd, J = 5.5, 7.7) |
| 9 | 80.18 | |
| 11 | 149.85 | |
| 12 | 120.61 | |
| 13 | 48.62 | 4.78 (2H, s) |
| 14 | 38.42 | 1.77 (2H, m) |
| 15 | 22.21 | 2.26 (2H, m) |
| 16 | 125.31 | 5.20 (1H, m) |
| 17 | 135.65 | |
| 18 | 40.45 | 1.97 (2H, m) |
| 19 | 27.39 | ~2.06 (2H, m) |
| 20 | 125.10 | 5.08 (1H, m) |
| 21 | 131.67 | |
| 22 | 25.78 | 1.62 (3H, s) |
| 23 | 17.68 | 1.55 (3H, s) |
| 24 | 16.00 | 1.62 (3H, s) |
| 25 | 18.57 | 1.32 (3H, s) |
| 26 | 147.49 | |
| 27 | 106.43 | 7.69 (1H, d, J = 2.2) |
| 28 | 163.73 | |
| 29 | 108.46 | |

TABLE 9-continued

I-5: SMTP-22

| No. | $\delta_C$ | $\delta_H$ |
|---|---|---|
| 30 | 132.00 | 7.89 (1H, d, J = 8.8) |
| 31 | 110.15 | 7.54 (1H, dd, J = 2.2, 8.8) |
| 32 | 172.24 | |

The chemical shift is relative to acetone-$d_6$ ($\delta_C$ 29.8 ppm [methyl carbon atom]; $\delta_H$ 2.04 ppm). The coupling constant (J) is given in Hz.

Example 14

Synthesis of Compound I-6

Preliminary culture was performed in the same manner as in Example 10.

Main culture was performed in the same manner as in Example 11, except that the organic amine compound added on day 4 of the main culture was changed to 4-amino-3-hydroxybenzoic acid.

Crude purification was performed in the same manner as in Example 10, to obtain 170 mg of a dried solid product. MeOH was added to this dried solid product to obtain a 100 mg/ml solution, and the solution was subjected to a pretreatment in the same manner as in Example 10. Reverse phase HPLC was performed in the same manner as in Example 10, except for the developing conditions. For the developing solvent, methanol containing 50 mM ammonium acetate was used, and the methanol concentration was increased linearly from 70% to 100% over 40 minutes. A peak was fractionated at a retention time of 14.3 to 15.3 minutes. The obtained fraction was purified in the same manner as in Example 10, to obtain 9.54 mg of a purified product of compound I-6.

The properties of the compound I-6 were determined as follows.

MALDI-TOF-MS, UV, FT-IR and NMR were measured in the same manner as in Example 11.

The physicochemical properties of the compound I-6 are presented in the following.

Molecular formula: $C_{30}H_{35}NO_7$
MALDI-TOF-MS (m/z)
Found $(M+H)^+$: 522.2533.
Calculated: 522.2492 for $C_{30}H_{36}NO_7$.
UV λmax nm (ε): 206 (66,823), 263 (16,471), 297 (13,865)
IR νmax (NaCl) $cm^{-1}$: 3388, 2968, 2922, 2858, 2578, 1697, 1614, 1466, 1371, 1215, 1076
NMR

TABLE 10

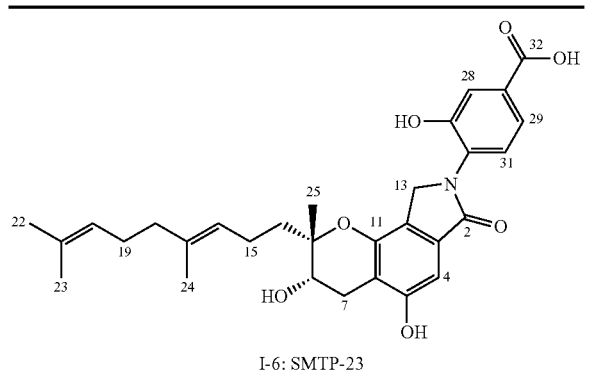

I-6: SMTP-23

| No. | δ$_C$ | δ$_H$ |
|---|---|---|
| 2 | 170.02 | |
| 3 | 132.48 | |
| 4 | 100.86 | 6.87 (1H, s) |
| 5 | 157.57 | |
| 6 | 114.25 | |
| 7 | 27.71 | 3.06 (1H, dd, J = 5.5, 17.6) |
| | | 2.71 (1H, dd, J = 7.7, 17.6) |
| 8 | 67.55 | 3.98 (1H, dd, J = 5.5, 7.7) |
| 9 | 80.23 | |
| 11 | 149.82 | |
| 12 | 122.48 | |
| 13 | 50.64 | 4.93 (2H, d, J = 4.0) |
| 14 | 38.40 | 1.76 (2H, m) |
| 15 | 22.18 | 2.24 (2H, m) |
| 16 | 125.21 | 5.18 (1H, m) |
| 17 | 135.67 | |
| 18 | 40.41 | 1.96 (2H, m) |
| 19 | 27.38 | ~2.05 (2H, m) |
| 20 | 125.07 | 5.07 (1H, m) |
| 21 | 131.53 | |
| 22 | 25.77 | 1.62 (3H, s) |
| 23 | 17.67 | 1.55 (3H, s) |
| 24 | 15.98 | 1.60 (3H, s) |
| 25 | 18.57 | 1.31 (3H, s) |
| 26 | 131.66 | |
| 27 | 151.74 | |
| 28 | 121.30 | 7.65 (1H, d, J = 1.8) |
| 29 | 130.51 | |
| 30 | 122.53 | 7.63 (1H, dd, J = 1.8, 8.4) |
| 31 | 125.13 | 7.59 (1H, d, J = 8.4) |
| 32 | 167.05 | |

The chemical shift is relative to acetone-d$_6$ (δ$_C$ 29.8 ppm [methyl carbon atom]; δ$_H$ 2.04 ppm). The coupling constant (J) is given in Hz.

Example 15

Synthesis of Compound I-7

Preliminary culture was performed in the same manner as in Example 10.

Main culture was performed in the same manner as in Example 11, except that the organic amine compound added on day 4 of the main culture was changed to 3-hydroxyanthranilic acid.

Crude purification was performed in the same manner as in Example 10, to obtain 200 mg of a dried solid product. MeOH was added to this dried solid product to obtain a 100 mg/ml solution, and the solution was subjected to a pretreatment in the same manner as in Example 10. Reverse phase HPLC was performed in the same manner as in Example 10, except for the developing conditions. For the developing solvent, methanol containing 50 mM ammonium acetate was used, and the methanol concentration was increased linearly from 70% to 80% over 10 minutes, and then maintained at 80% for 10 minutes. A peak was fractionated at a retention time of 12.4 to 13.5 minutes. The obtained fraction was purified in the same manner as in Example 10, to obtain 31.1 mg of a purified product of compound I-7.

The properties of the compound I-7 were determined as follows.

MALDI-TOF-MS, UV, FT-IR and NMR were measured in the same manner as in Example 11.

The physicochemical properties of the compound I-7 are presented in the following.

Molecular formula: $C_{30}H_{35}NO_7$

MALDI-TOF-MS (m/z)

Found (M+H)$^+$: 522.2327.

Calculated: 522.2492 for $C_{30}H_{36}NO_7$.

UV λmax nm (ε): 213 (57,753), 255 (11,155), 290 (7,714)

IR νmax (NaCl) cm$^{-1}$: 3356, 2968, 2920, 2858, 1697, 1616, 1470, 1294, 1159, 1076, 762

NMR

TABLE 11

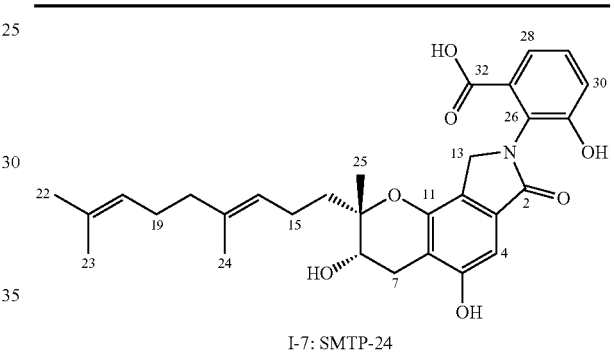

I-7: SMTP-24

| No. | δ$_C$ | δ$_H$ |
|---|---|---|
| 2 | 170.06 | |
| 3 | 132.63 | |
| 4 | 101.04 | 6.83 (1H, d, J = 4.8) |
| 5 | 156.97 | |
| 6 | 112.87 | |
| 7 | 27.62 | 3.05 (1H, dd, J = 5.4, 17.4) |
| | | 2.69 (1H, dd, J = 7.8, 17.4) |
| 8 | 67.78 | 3.95 (1H, dd, J = 5.4, 7.8) |
| 9 | 79.81 | |
| 11 | 149.63 | |
| 12 | 122.29 | |
| 13 | 49.76 | 4.60 (2H, br) |
| 14 | 38.57 | 1.75 (2H, m) |
| 15 | 22.15 | 2.22 (2H, m) |
| 16 | 125.21 | 5.18 (1H, t, J = 6.6) |
| 17 | 135.62 | |
| 18 | 40.38 | 1.95 (2H, t, J = 7.8) |
| 19 | 27.35 | ~2.07 (2H, m) |
| 20 | 125.07 | 5.07 (1H, t, J = 6.6) |
| 21 | 131.63 | |
| 22 | 25.76 | 1.62 (3H, s) |
| 23 | 17.65 | 1.55 (3H, s) |
| 24 | 15.97 | 1.59 (3H, s) |
| 25 | 18.37 | 1.29 (3H, s) |
| 26 | 126.16 | |
| 27 | 132.97 | |
| 28 | 120.91 | 7.49 (1H, d, J = 7.2) |
| 29 | 129.32 | 7.33 (1H, t, J = 7.8) |
| 30 | 122.60 | 7.23 (1H, d, J = 7.8) |
| 31 | 155.83 | |
| 32 | 167.31 | |

The chemical shift is relative to acetone-d$_6$ (δ$_C$ 29.8 ppm [methyl carbon atom]; δ$_H$ 2.04 ppm). The coupling constant (J) is given in Hz.

Example 16

Synthesis of Compound I-8

Preliminary culture was performed in the same manner as in Example 10.

Main culture was performed in the same manner as in Example 11, except that the organic amine compound added on day 4 of the main culture was changed to 3-aminosalicylic acid.

Crude purification was performed in the same manner as in Example 10, to obtain 280 mg of a dried solid product. MeOH was added to this dried solid product to obtain a 100 mg/ml solution, and the solution was subjected to a pretreatment in the same manner as in Example 10. Reverse phase HPLC was performed in the same manner as in Example 10, except for the developing conditions. For the developing solvent, 75% methanol containing 50 mM ammonium acetate was used, and a peak was fractionated at a retention time of 16.0 to 18.6 minutes. The obtained fraction was purified in the same manner as in Example 10, to obtain 23.29 mg of a purified product of compound I-8.

The properties of the compound I-8 were determined as follows.

MALDI-TOF-MS, UV, FT-IR and NMR were measured in the same manner as in Example 11.

The physicochemical properties of the compound I-8 are presented in the following.

Molecular formula: $C_{30}H_{35}NO_7$
MALDI-TOF-MS (m/z)
Found (M+H)$^+$: 522.2537.
Calculated: 2492 for $C_{30}H_{36}NO_7$.
UV λmax nm (ε): 4 (57,962), 256 (10,633), 304 (11,676)
IR νmax (NaCl) cm$^{-1}$: 221, 2850, 2918, 2976, 1678, 1616, 1464, 1240, 1157, 1074
NMR

TABLE 12

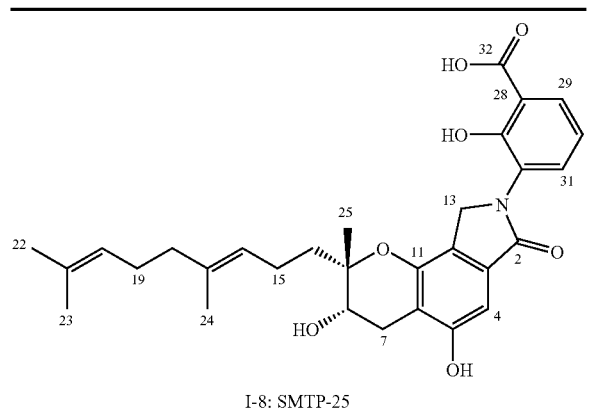

I-8: SMTP-25

| No. | $\delta_C$ | $\delta_H$ |
|---|---|---|
| 2 | 168.80 | |
| 3 | 132.48 | |
| 4 | 100.96 | 6.86 (1H, s) |
| 5 | 157.22 | |
| 6 | 113.12 | |
| 7 | 27.66 | 3.03 (1H, dd, J = 5.5, 17.6) |
|   |   | 2.67 (1H, dd, J = 7.7, 17.6) |
| 8 | 67.67 | 3.97 (1H, dd, J = 5.5, 7.7) |
| 9 | 79.90 | |
| 11 | 149.69 | |
| 12 | 121.74 | |

TABLE 12-continued

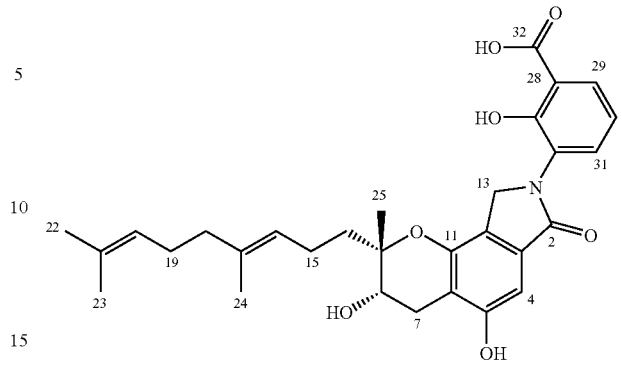

I-8: SMTP-25

| No. | $\delta_C$ | $\delta_H$ |
|---|---|---|
| 13 | 49.67 | 4.69 (2H, s) |
| 14 | 38.45 | 1.74 (2H, m) |
| 15 | 22.15 | 2.21 (2H, m) |
| 16 | 125.25 | 5.17 (1H, t, J = 7.0) |
| 17 | 135.55 | |
| 18 | 40.36 | 1.94 (2H, m) |
| 19 | 27.34 | 2.06 (2H, m) |
| 20 | 125.06 | 5.05 (1H, m) |
| 21 | 131.63 | |
| 22 | 25.76 | 1.61 (3H, s) |
| 23 | 17.64 | 1.53 (3H, s) |
| 24 | 15.94 | 1.58 (3H, s) |
| 25 | 18.39 | 1.26 (3H, s) |
| 26 | 127.82 | |
| 27 | 158.51 | |
| 28 | 115.53 | |
| 29 | 130.02 | 7.88 (1H, dd, J = 1.5, 7.7) |
| 30 | 119.13 | 6.98 (1H, t, J = 7.7) |
| 31 | 135.41 | 7.65 (1H, dd, J = 1.5, 7.7) |
| 32 | 173.03 | |

The chemical shift is relative to acetone-d$_6$ ($\delta_C$ 29.8 ppm [methyl carbon atom]; $\delta_H$ 2.04 ppm). The coupling constant (J) is given in Hz.

Example 17

Synthesis of Compound I-9

Preliminary culture was performed in the same manner as in Example 10.

Main culture was performed in the same manner as in Example 11, except that the organic amine compound added on day 4 of the main culture was changed to 5-aminosalicylic acid.

Crude purification was performed in the same manner as in Example 10, to obtain 502 mg of a dried solid product. MeOH was added to this dried solid product to obtain a 200 mg/ml solution, and the solution was subjected to a pretreatment in the same manner as in Example 10. Reverse phase HPLC was performed in the same manner as in Example 10, except for the developing conditions. For the developing solvent, 70% methanol containing 50 mM ammonium acetate was used, and a peak was fractionated at a retention time of 22.0 to 25.5 minutes. The obtained fraction was purified in the same manner as in Example 10, to obtain 66.34 mg of a purified product of compound I-9.

The properties of the compound I-9 were determined as follows.

MALDI-TOF-MS, UV, FT-IR and NMR were measured in the same manner as in Example 11.

The physicochemical properties of the compound I-9 are presented in the following.

Molecular formula: $C_{30}H_{35}NO_7$
MALDI-TOF-MS (m/z)
Found $(M+H)^+$: 522.2505.
Calculated: 522.2492 for $C_{30}H_{36}NO_7$.
UV λmax nm (ε): 214 (50,665), 259 (sh) (9,591), 295 (14,490)
IR νmax (NaCl) $cm^{-1}$: 3394, 2970, 2920, 2858, 1676, 1618, 1489, 1464, 1370, 1203, 1161, 1076
NMR

TABLE 13

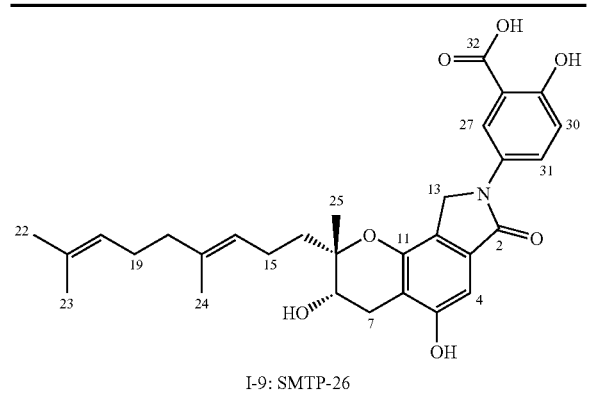

I-9: SMTP-26

| No. | $\delta_C$ | $\delta_H$ |
| --- | --- | --- |
| 2 | 167.84 | |
| 3 | 133.34 | |
| 4 | 100.78 | 6.84 (1H, s) |
| 5 | 157.31 | |
| 6 | 113.23 | |
| 7 | 27.68 | 3.04 (1H, dd, J = 5.5, 17.2) |
| | | 2.68 (1H, dd, J = 7.7, 17.2) |
| 8 | 67.61 | 3.96 (1H, dd, J = 5.5, 7.7) |
| 9 | 80.02 | |
| 11 | 149.76 | |
| 12 | 120.38 | |
| 13 | 48.98 | 4.73 (2H, s) |
| 14 | 38.46 | 1.76 (2H, m) |
| 15 | 22.21 | 2.24 (2H, m) |
| 16 | 125.31 | 5.19 (1H, m) |
| 17 | 135.62 | |
| 18 | 40.43 | 1.96 (2H, m) |
| 19 | 27.38 | ~2.06 (2H, m) |
| 20 | 125.11 | 5.07 (1H, m) |
| 21 | 131.64 | |
| 22 | 25.78 | 1.61 (3H, m) |
| 23 | 17.68 | 1.54 (3H, s) |
| 24 | 16.00 | 1.60 (3H, s) |
| 25 | 18.59 | 1.31 (3H, s) |
| 26 | 132.64 | |
| 27 | 117.86 | 6.94 (1H, d, J = 9.2) |
| 28 | 114.88 | |
| 29 | 159.31 | |
| 30 | 122.02 | 8.36 (1H, d, J = 2.6) |
| 31 | 127.82 | 8.07 (1H, dd, J = 2.6, 9.2) |
| 32 | 173.07 | |

The chemical shift is relative to acetone-$d_6$ ($\delta_C$ 29.8 ppm [methyl carbon atom]; $\delta_H$ 2.04 ppm). The coupling constant (J) is given in Hz.

Example 18

Synthesis of Compound I-10

Preliminary culture was performed in the same manner as in Example 10.

Main culture was performed in the same manner as in Example 11, except that the organic amine compound added on day 4 of the main culture was changed to 3-amino-4-hydroxybenzoic acid.

Crude purification was performed in the same manner as in Example 10, to obtain 420 mg of a dried solid product. MeOH was added to this dried solid product to obtain a 150 mg/ml solution, and the solution was subjected to a pretreatment in the same manner as in Example 10. Reverse phase HPLC was performed in the same manner as in Example 10, except for the developing conditions. For the developing solvent, methanol containing 50 mM ammonium acetate was used, and the methanol concentration was maintained at 65% for 25 minutes, subsequently increased linearly from 65% to 100% over 5 minutes, and then maintained at 100% for 10 minutes. A peak was fractionated at a retention time of 28.7 to 32.5 minutes. The obtained fraction was purified in the same manner as in Example 10, to obtain 78.94 mg of a purified product of compound I-10.

The properties of the compound I-10 were determined as follows.

MALDI-TOF-MS, UV, FT-IR and NMR were measured in the same manner as in Example 11.

The physicochemical properties of the compound I-10 are presented in the following.
Molecular formula: $C_{30}H_{35}NO_7$
MALDI-TOF-MS (m/z)
Found $(M+H)^+$: 522.2550.
Calculated: 522.2492 for $C_{30}H_{36}NO_7$.
UV λmax nm (ε): 215 (52,124), 252 (22,205), 308 (sh) (6,255)
IR νmax (NaCl) $cm^{-1}$: 3803, 3429, 3068, 2970, 2924, 2860, 2549, 2517, 1691, 1601, 1464, 1302, 1076, 1036
NMR

TABLE 14

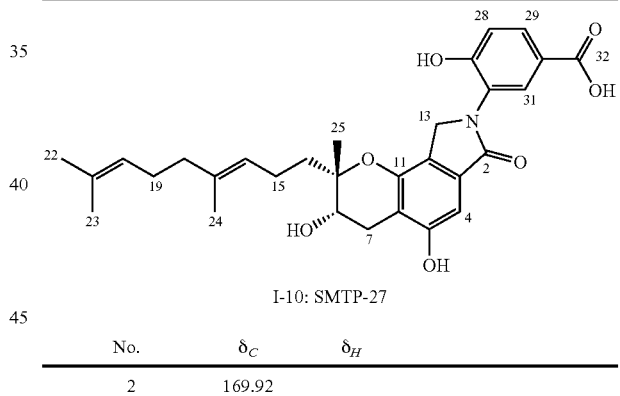

I-10: SMTP-27

| No. | $\delta_C$ | $\delta_H$ |
| --- | --- | --- |
| 2 | 169.92 | |
| 3 | 131.78 | |
| 4 | 100.82 | 6.87 (1H, s) |
| 5 | 157.43 | |
| 6 | 113.91 | |
| 7 | 27.69 | 3.05 (1H, dd, J = 5.4, 17.4) |
| | | 2.70 (1H, dd, J = 7.8, 17.4) |
| 8 | 67.54 | 3.98 (1H, dd, J = 5.4, 7.8) |
| 9 | 80.15 | |
| 11 | 149.83 | |
| 12 | 122.39 | |
| 13 | 50.58 | 4.88 (2H, d, J = 1.8) |
| 14 | 38.45 | 1.76 (2H, m) |
| 15 | 22.18 | 2.24 (2H, m) |
| 16 | 125.26 | 5.18 (1H, m) |
| 17 | 135.63 | |
| 18 | 40.40 | 1.95 (2H, m) |
| 19 | 27.36 | ~2.06 (2H, m) |
| 20 | 125.09 | 5.06 (1H, m) |
| 21 | 131.63 | |
| 22 | 25.78 | 1.61 (3H, s) |
| 23 | 17.68 | 1.54 (3H, s) |
| 24 | 15.98 | 1.60 (3H, s) |
| 25 | 18.54 | 1.31 (3H, s) |

TABLE 14-continued

I-10: SMTP-27

| No. | $\delta_C$ | $\delta_H$ |
|---|---|---|
| 26 | 127.96 | |
| 27 | 156.64 | |
| 28 | 119.43 | 7.08 (1H, d, J = 8.4) |
| 29 | 130.36 | 7.87 (1H, dd, J = 2.4, 8.4) |
| 30 | 123.67 | |
| 31 | 128.11 | 8.09 (1H, d, J = 2.4) |
| 32 | 167.05 | |

The chemical shift is relative to acetone-$d_6$ ($\delta_C$ 29.8 ppm [methyl carbon atom]; $\delta_H$ 2.04 ppm). The coupling constant (J) is given in Hz.

Example 19

Synthesis of Compound I-11

Preliminary culture was performed in the same manner as in Example 10.

Main culture was performed in the same manner as in Example 11, except that the organic amine compound added on day 4 of the main culture was changed to 5-hydroxyanthranilic acid.

Crude purification was performed in the same manner as in Example 10, to obtain 305 mg of a dried solid product. MeOH was added to this dried solid product to obtain a 100 mg/ml solution, and the solution was subjected to a pretreatment in the same manner as in Example 10. Reverse phase HPLC was performed in the same manner as in Example 10, except for the detection method and the developing conditions. Detection was conducted using a diode array detector, and the region of 260 to 350 nm was monitored. For the developing solvent, 80% methanol containing 0.1% (vol/vol) formic acid was used, and a peak was fractionated at a retention time of 16.7 to 17.7 minutes. The obtained fraction was concentrated in a rotary evaporator to eliminate methanol, and then was freeze-dried. n-Hexane was added to the dried solid product, and the mixture was stirred and then centrifuged to recover the insoluble. This operation was repeated three times to dissolve the insoluble in methanol, and the resulting solution was filtered, concentrated and dried to solids, to thus obtain 43.37 mg of a purified product of compound I-11.

The properties of the compound I-11 were determined as follows.

MALDI-TOF-MS, UV, FT-IR and NMR were measured in the same manner as in Example 11.

The physicochemical properties of the compound I-11 are presented in the following.

Molecular formula: $C_{30}H_{35}NO_7$

MALDI-TOF-MS (m/z)

Found (M+H)$^+$: 522.2516.

Calculated: 522.2492 for $C_{30}H_{36}NO_7$.

UV λmax nm (ε): 214 (66,614), 260 (16,471), 297 (sh) (9,695)

IR vmax (NaCl) cm$^{-1}$: 3373, 3329, 2970, 2920, 2860, 1705, 1660, 1610, 1504, 1464, 1338, 1296, 1219, 1076, 1032

NMR

TABLE 15

I-11: SMTP-28

| No. | $\delta_C$ | $\delta_H$ |
|---|---|---|
| 2 | 169.32 | |
| 3 | 133.00 | |
| 4 | 100.97 | 6.82 (1H, d, J = 2.9) |
| 5 | 157.08 | |
| 6 | 112.83 | |
| 7 | 27.65 | 3.04 (1H, dd, J = 5.5, 17.6) |
|   |        | 2.68 (1H, dd, J = 7.7, 17.6) |
| 8 | 67.75 | 3.94 (1H, dd, J = 5.5, 7.7) |
| 9 | 79.89 | |
| 11 | 149.64 | |
| 12 | 121.70 | |
| 13 | 51.48 | 4.61 (2H, s) |
| 14 | 38.56 | 1.74 (2H, m) |
| 15 | 22.17 | 2.22 (2H, m) |
| 16 | 125.25 | 5.18 (1H, m) |
| 17 | 135.63 | |
| 18 | 40.42 | 1.95 (2H, m) |
| 19 | 27.39 | ~2.06 (2H, m) |
| 20 | 125.10 | 5.07 (1H, m) |
| 21 | 131.65 | |
| 22 | 25.79 | 1.62 (3H, m) |
| 23 | 17.68 | 1.55 (3H, s) |
| 24 | 15.97 | 1.59 (3H, s) |
| 25 | 18.42 | 1.28 (3H, s) |
| 26 | 131.22 | |
| 27 | 131.58 | |
| 28 | 118.08 | 7.44 (1H, d, J = 2.9) |
| 29 | 157.16 | |
| 30 | 120.07 | 7.09 (1H, dd, J = 2.9, 8.4) |
| 31 | 130.95 | 7.34 (1H, d, J = 8.4) |
| 32 | 167.09 | |

The chemical shift is relative to acetone-$d_6$ ($\delta_C$ 29.8 ppm [methyl carbon atom]; $\delta_H$ 2.04 ppm). The coupling constant (J) is given in Hz.

Example 20

Synthesis of Compound I-16

Preliminary culture was performed in the same manner as in Example 9.

Main culture was performed in the same manner as in Example 11, except that the organic amine compound added on day 4 of the main culture was changed to adenine.

Crude purification was performed in the same manner as in Example 9, to obtain 123 mg of a dried solid product. MeOH was added to this dried solid product to obtain a 100 mg/ml solution, and the solution was subjected to a pretreatment in the same manner as in Example 9. Reverse phase HPLC was performed in the same manner as in Example 9, except for the developing conditions. For the developing solvent, methanol containing 50 mM ammonium acetate was used, and the methanol concentration was increased linearly from 70% to 100% over 30 minutes. A peak was fractionated at a retention time of 17.5 to 18 minutes. The obtained fraction was purified in the same manner as in Example 9, to obtain 1.66 mg of a purified product of compound I-16.

The properties of the compound I-16 were determined as follows.

MALDI-TOF-MS and UV were measured in the same manner as in Example 9.

The physicochemical properties of the compound I-16 are presented in the following.

Molecular formula: $C_{28}H_{33}N_5O_4$
MALDI-TOF-MS (m/z)
Found (M+H)$^+$: 504.2665.
Calculated: 504.2611 for $C_{28}H_{34}N_5O_4$.
UV λmax nm (ε): 212 (43,984), 258 (9,260), 301 (3,422)

Example 21

Synthesis of Compound I-17

Preliminary culture was performed in the same manner as in Example 9.

Main culture was performed in the same manner as in Example 11, except that the organic amine compound added on day 4 of the main culture was changed to 5-amino-2,3-dihydro-1,4-phthalazinedione.

Crude purification was performed in the same manner as in Example 9, to obtain 130 mg of a dried solid product. MeOH was added to this dried solid product to obtain a 100 mg/ml solution, and the solution was subjected to a pretreatment in the same manner as in Example 9. Reverse phase HPLC was performed in the same manner as in Example 9, except for the developing conditions. For the developing solvent, 75% methanol containing 50 mM ammonium acetate was used, and a peak was fractionated at a retention time of 16.5 to 17.5 minutes. The fractionated fraction was purified in the same manner as in Example 9, to obtain 10.20 mg of a purified product of compound I-17.

The properties of the compound I-17 were determined as follows.

MALDI-TOF-MS, UV and FT-IR were measured in the same manner as in Example 9.

The physicochemical properties of the compound I-17 are presented in the following.

Molecular formula: $C_{31}H_{35}N_3O_6$
MALDI-TOF-MS (m/z)
Found (M+H)$^+$: 546.2742.
Calculated: 546.2604 for $C_{31}H_{36}N_3O_6$.
UV λmax nm (ε): 208 (85,822), 260 (14,722), 306 (11,668)
IR νmax (NaCl) cm$^{-1}$: 3408, 3259, 2968, 2918, 2858, 1659, 1605, 1473, 1333, 1159, 1076, 1041

Example 22

Synthesis of Compound I-18

Preliminary culture was performed in the same manner as in Example 9.

Main culture was performed in the same manner as in Example 11, except that the organic amine compound added on day 4 of the main culture was changed to 1-amino-2-naphthol-4-sulfonic acid.

Crude purification was performed in the same manner as in Example 9, to obtain 199 mg of a dried solid product. MeOH was added to this dried solid product to obtain a 100 mg/ml solution, and the solution was subjected to a pretreatment in the same manner as in Example 9. Reverse phase HPLC was performed in the same manner as in Example 9, except for the developing conditions. For the developing solvent, methanol containing 50 mM ammonium acetate was used, and the methanol concentration was increased linearly from 70% to 100% over 30 minutes. A peak was fractionated at a retention time of 14.5 to 15.5 minutes. The obtained fraction was purified in the same manner as in Example 9, to obtain 18.40 mg of a purified product of compound I-18.

The properties of the compound I-18 were determined as follows.

MALDI-TOF-MS, UV and FT-IR were measured in the same manner as in Example 9.

The physicochemical properties of the compound I-18 are presented in the following.

Molecular formula: $C_{33}H_{37}NO_8S$
MALDI-TOF-MS (m/z)
Found (M+H)$^+$: 608.2346.
Calculated: 608.2318 for $C_{33}H_{38}NO_8S$.
UV λmax nm (ε): 217 (63,880), 234 (sh) (49,185), 260 (12,144), 285 (11,173), 296 (11,051), 326 (5,586), 338 (60, 72)
IR νmax (NaCl) cm$^{-1}$: 3452, 3242, 2968, 2916, 2858, 2146, 1670, 1616, 1464, 1425, 1358, 1171, 1051

Example 23

Synthesis of Compound I-19

Preliminary culture was performed in the same manner as in Example 9.

Main culture was performed in the same manner as in Example 11, except that the organic amine compound added on day 4 of the main culture was changed to p-sulfanilic acid.

Crude purification was performed in the same manner as in Example 9, to obtain 316 mg of a dried solid product. MeOH was added to this dried solid product to obtain a 100 mg/ml solution, and the solution was subjected to a pretreatment in the same manner as in Example 9. Reverse phase HPLC was performed in the same manner as in Example 9, except for the developing conditions. For the developing solvent, methanol containing 50 mM ammonium acetate was used, and the methanol concentration was increased linearly from 65% to 100% over 35 minutes. A peak was fractionated at a retention time of 18 to 18.5 minutes. The obtained fraction was purified in the same manner as in Example 19, to obtain 12.33 mg of a purified product of compound I-19.

The properties of the compound I-19 were determined as follows.

MALDI-TOF-MS, UV, FT-IR and NMR were measured in the same manner as in Example 12.

The physicochemical properties of the compound I-19 are presented in the following.

Molecular formula: $C_{29}H_{35}NO_7S$
MALDI-TOF-MS (m/z)
Found (M+H)$^+$: 542.2233.
Calculated: 542.2212 for $C_{29}H_{36}NO_7S$.
UV λmax nm (ε): 224 (sh) (25,112), 286 (19,484)
IR νmax (NaCl) cm$^{-1}$: 3188, 3057, 2972, 2918, 2856, 1697, 1606, 1460, 1367, 1174, 1132, 1080, 1036
NMR

TABLE 16

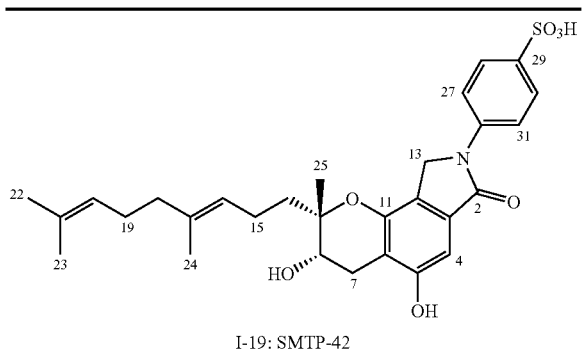

I-19: SMTP-42

| No. | $\delta_C$ | $\delta_H$ |
|---|---|---|
| 2 | 166.88 | |
| 3 | 131.47 | |
| 4 | 99.62 | 6.73 (1H, s) |
| 5 | 156.34 | |
| 6 | 112.57 | |
| 7 | 26.66 | 2.86 (1H, dd, J = 5.5, 17.6) |
|   |       | 2.51 (1H, dd, J = 7.7, 17.6) |
| 8 | 65.83 | 3.77 (1H, dd, J = 5.5, 7.3) |
| 9 | 78.88 | |
| 11 | 148.35 | |
| 12 | 118.71 | |
| 13 | 47.71 | 4.71 (1H, dd, J = 16.1, 24.9) |
| 14 | 37.08 | 1.63 (2H, dd, J = 7.0, 9.2) |
| 15 | 20.98 | 2.15 (2H, m) |
| 16 | 124.16 | 5.14 (1H, m) |
| 17 | 134.26 | |
| 18 | ~39.5 | 1.92 (2H, m) |
| 19 | 26.07 | 2.00 (2H, m) |
| 20 | 123.96 | 5.04 (1H, m) |
| 21 | 130.52 | |
| 22 | 25.27 | 1.60 (3H, s) |
| 23 | 17.36 | 1.52 (3H, s) |
| 24 | 15.57 | 1.56 (3H, s) |
| 25 | 18.12 | 1.20 (3H, s) |
| 26 | 143.77 | |
| 27, 31 | 126.06 | 7.61 (2H, m) |
| 28, 30 | 117.85 | 7.83 (2H, m) |
| 29 | 139.55 | |

The chemical shift is relative to dimethyl-$d_6$-sulfoxide ($\delta_C$ 39.5 ppm [methyl carbon atom]; $\delta_H$ 2.49 ppm). The coupling constant (J) is given in Hz.

Example 24

Synthesis of Compound I-20

Preliminary culture was performed in the same manner as in Example 9.

Main culture was performed in the same manner as in Example 11, except that the organic amine compound added on day 4 of the main culture was changed to L-phenylglycine.

Crude purification was performed in the same manner as in Example 9, to obtain 270 mg of a dried solid product. MeOH was added to this dried solid product to obtain a 100 mg/ml solution, and the solution was subjected to a pretreatment in the same manner as in Example 9. Reverse phase HPLC was performed in the same manner as in Example 9, except for the developing conditions. For the developing solvent, methanol containing 50 mM ammonium acetate was used, and the methanol concentration was increased linearly from 75% to 90% over 40 minutes. A peak was fractionated at a retention time of 15 to 18.5 minutes. The obtained fraction was purified in the same manner as in Example 9, to obtain 37.85 mg of a purified product of compound I-20.

The properties of the compound I-20 were determined as follows.

MALDI-TOF-MS, UV, FT-IR and NMR were measured in the same manner as in Example 11.

The physicochemical properties of the compound I-20 are presented in the following.

Molecular formula: $C_{31}H_{37}NO_6$
MALDI-TOF-MS (m/z)
Found (M+H)$^+$: 520.2662.
Calculated: 520.2699 for $C_{31}H_{38}NO_6$.
UV λmax nm (ε): 214 (46,214), 259 (11,112), 300 (3,012)
IR νmax (NaCl) cm$^{-1}$: 3423, 2968, 2920, 2864, 1726, 1660, 1620, 1464, 1350, 1205, 1169, 1074
NMR

TABLE 17

I-20: SMTP-43

| No. | $\delta_C$ | $\delta_H$ |
|---|---|---|
| 2 | 169.12 | |
| 3 | 132.22 | |
| 4 | 100.77 | 6.81 (1H, s) |
| 5 | 157.10 | |
| 6 | 112.88 | |
| 7 | 27.59 | 2.99 (1H, dd, J = 5.5, 17.6) |
|   |       | 2.63 (1H, dd, J = 7.7, 17.6) |
| 8 | 67.47 | 3.91 (1H, dd, J = 5.5, 7.7) |
| 9 | 79.94 | |
| 11 | 149.82 | |
| 12 | 121.82 | |
| 13 | 45.62 | 4.53 (1H, d, J = 16.5) |
|   |       | 3.73 (1H, d, J = 16.5) |
| 14 | 38.35 | 1.69 (2H, m) |
| 15 | 22.19 | 2.16 (2H, m) |
| 16 | 125.23 | 5.15 (1H, m) |
| 17 | 135.61 | |
| 18 | 40.40 | 1.95 (2H, t, J = 7.8) |
| 19 | 27.38 | ~2.06 (2H, m) |
| 20 | 125.12 | 5.08 (1H, m) |
| 21 | 131.65 | |
| 22 | 25.80 | 1.63 (3H, s) |
| 23 | 17.70 | 1.56 (3H, s) |
| 24 | 15.95 | 1.57 (3H, s) |
| 25 | 18.58 | 1.20 (3H, s) |
| 26 | 58.81 | 6.16 (1H, s) |
| 27 | 136.19 | |
| 28, 32 | 129.70 | 7.45 (2H, m) |
| 29, 31 | 129.83 | 7.45 (2H, m) |
| 30 | 129.32 | 7.40 (1H, m) |
| 33 | 171.81 | |

The chemical shift is relative to acetone-$d_6$ ($\delta_C$ 29.8 ppm [methyl carbon atom]; $\delta_H$ 2.04 ppm). The coupling constant (J) is given in Hz.

Example 25

Synthesis of Compound I-21

Preliminary culture was performed in the same manner as in Example 9

Main culture was performed in the same manner as in Example 11, except that the organic amine compound added on day 4 of the main culture was changed to D-phenylglycine.

Crude purification was performed in the same manner as in Example 9, to obtain 150 mg of a dried solid product. MeOH was added to this dried solid product to obtain a 75 mg/ml solution, and the solution was subjected to a pretreatment in the same manner as in Example 9. Reverse phase HPLC was performed in the same manner as in Example 9, except for the developing conditions. For the developing solvent, methanol containing 50 mM ammonium acetate was used, and the methanol concentration was increased linearly from 70% to 100% over 30 minutes. A peak was fractionated at a retention time of 19 to 20.5 minutes. The obtained fraction was purified in the same manner as in Example 9, to obtain 17.59 mg of a purified product of compound I-21.

The properties of the compound I-21 were determined as follows.

MALDI-TOF-MS, UV, FT-IR and NMR were measured in the same manner as in Example 11.

The physicochemical properties of the compound I-21 are presented in the following.

Molecular formula: $C_3H_{37}NO_6$

MALDI-TOF-MS (m/z)

Found $(M+H)^+$: 520.2747.

Calculated: 520.2699 for $C_{31}H_{38}NO_6$.

UV λmax nm (ε): 215 (44,864), 259 (11,008), 300 (3,012)

IR νmax (NaCl) $cm^{-1}$: 3354, 2968, 2922, 2862, 1714, 1664, 1620, 1466, 1356, 1207, 1169, 1074

NMR

TABLE 18

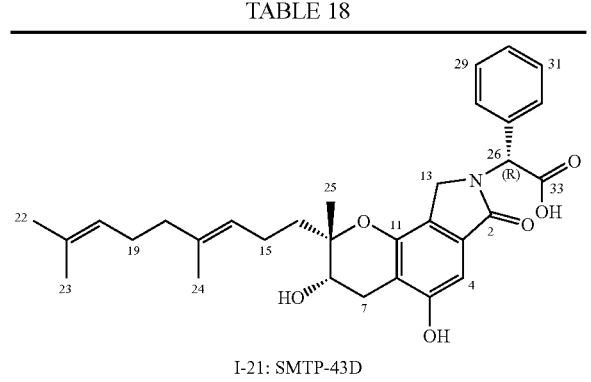

I-21: SMTP-43D

| No. | $\delta_C$ | $\delta_H$ |
|---|---|---|
| 2 | 169.12 | |
| 3 | 132.20 | |
| 4 | 100.78 | 6.81 (1H, s) |
| 5 | 157.13 | |
| 6 | 112.83 | |
| 7 | 27.58 | 2.97 (1H, dd, J = 5.4, 17.4) |
| | | 2.65 (1H, dd, J = 7.2, 17.6) |
| 8 | 67.55 | 3.87 (1H, dd, J = 5.4, 7.2) |
| 9 | 79.94 | |
| 11 | 149.79 | |
| 12 | 121.81 | |
| 13 | 45.61 | 4.52 (1H, d, J = 16.8) |
| | | 3.73 (1H, d, J = 16.8) |
| 14 | 38.27 | 1.65 (2H, m) |
| 15 | 22.16 | 2.09 (2H, m) |
| 16 | 125.20 | 5.08 (1H, m) |
| 17 | 135.46 | |
| 18 | 40.32 | 1.88 (2H, t, J = 7.8) |
| 19 | 27.29 | 2.00 (2H, m) |
| 20 | 123.98 | 5.04 (1H, m) |
| 21 | 131.62 | |
| 22 | 25.77 | 1.61 (3H, s) |
| 23 | 17.68 | 1.54 (3H, s) |
| 24 | 15.83 | 1.47 (3H, s) |
| 25 | 18.64 | 1.25 (3H, s) |
| 26 | 58.82 | 6.16 (1H, s) |

TABLE 18-continued

I-21: SMTP-43D

| No. | $\delta_C$ | $\delta_H$ |
|---|---|---|
| 27 | 136.12 | |
| 28, 32 | 129.68 | 7.44 (2H, m) |
| 29, 31 | 129.78 | 7.44 (2H, m) |
| 30 | 129.27 | 7.40 (1H, m) |
| 33 | 171.89 | |

The chemical shift is relative to acetone-$d_6$ ($\delta_C$ 29.8 ppm [methyl carbon atom]; $\delta_H$ 2.04 ppm). The coupling constant (J) is given in Hz.

Example 26

Synthesis of Compound I-22

Preliminary culture was performed in the same manner as in Example 9.

Main culture was performed in the same manner as in Example 11, except that the organic amine compound added on day 4 of the main culture was changed to L-4-hydroxyphenylglycine.

Crude purification was performed in the same manner as in Example 9, to obtain 365 mg of a dried solid product. MeOH was added to this dried solid product to obtain a 150 mg/ml solution, and the solution was subjected to a pretreatment in the same manner as in Example 9. Reverse phase HPLC was performed in the same manner as in Example 19, except for the developing conditions. For the developing solvent, methanol and 0.1% (vol/vol) of formic acid were used, and the methanol concentration was increased linearly from 75% to 90% over 30 minutes. A peak was fractionated at a retention time of 13 to 14 minutes. The obtained fraction was purified in the same manner as in Example 19, to obtain 69.68 mg of a purified product of compound I-22.

The properties of the compound I-22 were determined as follows.

MALDI-TOF-MS, UV, FT-IR and NMR were measured in the same manner as in Example 11.

The physicochemical properties of the compound I-22 are presented in the following.

Molecular formula: $C_{31}H_{37}NO_7$

MALDI-TOF-MS (m/z)

Found $(M+H)^+$: 536.2656.

Calculated: 536.2648 for $C_{31}H_{38}NO_7$.

UV λmax nm (ε): 216 (42,714), 262 (11,026), 300 (2,783)

IR νmax (NaCl) $cm^{-1}$: 3348, 2974, 2922, 2856, 1718, 1660, 1612, 1514, 1464, 1365, 1211, 1173, 1072

NMR

TABLE 19

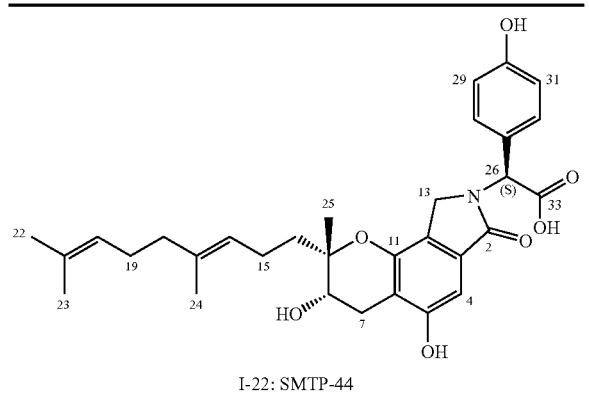

I-22: SMTP-44

| No. | $\delta_C$ | $\delta_H$ |
|---|---|---|
| 2 | 169.02 | |
| 3 | 132.42 | |
| 4 | 100.70 | 6.80 (1H, s) |
| 5 | 157.03 | |
| 6 | 112.76 | |
| 7 | 27.59 | 2.99 (1H, dd, J = 5.5, 17.6) |
| | | 2.63 (1H, dd, J = 7.7, 17.6) |
| 8 | 67.45 | 3.91 (1H, dd, J = 5.5, 7.7) |
| 9 | 79.90 | |
| 11 | 149.80 | |
| 12 | 121.65 | |
| 13 | 45.62 | 4.50 (1H, d, J = 16.5) |
| | | 3.74 (1H, d, J = 16.5) |
| 14 | 38.35 | 1.69 (2H, m) |
| 15 | 22.18 | 2.16 (2H, m) |
| 16 | 125.23 | 5.15 (1H, m) |
| 17 | 135.60 | |
| 18 | 40.40 | 1.96 (2H, m) |
| 19 | 27.37 | ~2.06 (2H, m) |
| 20 | 125.12 | 5.08 (1H, m) |
| 21 | 131.65 | |
| 22 | 25.80 | 1.63 (3H, m) |
| 23 | 17.70 | 1.56 (3H, s) |
| 24 | 15.95 | 1.57 (3H, m) |
| 25 | 18.56 | 1.20 (3H, s) |
| 26 | 58.27 | 6.05 (1H, s) |
| 27 | 126.74 | |
| 28, 32 | 131.03 | 7.27 (2H, m) |
| 29, 31 | 116.48 | 6.91 (2H, m) |
| 30 | 158.43 | |
| 33 | 172.13 | |

The chemical shift is relative to acetone-$d_6$ ($\delta_C$ 29.8 ppm [methyl carbon atom]; $\delta_H$ 2.04 ppm). The coupling constant (J) is given in Hz.

Example 27

Synthesis of Compound I-23

Preliminary culture was performed in the same manner as in Example 9.

Main culture was performed in the same manner as in Example 11, except that the organic amine compound added on day 4 of the main culture was changed to D-4-hydroxyphenylglycine.

Crude purification was performed in the same manner as in Example 9, to obtain 510 mg of a dried solid product. MeOH was added to this dried solid product to obtain a 200 mg/ml solution, and the solution was subjected to a pretreatment in the same manner as in Example 9. Reverse phase HPLC was performed in the same manner as in Example 19, except for the developing conditions. For the developing solvent, methanol and 0.1% (vol/vol) of formic acid were used, and the methanol concentration was increased linearly from 75% to 90% over 30 minutes. A peak was fractionated at a retention time of 13.5 to 15 minutes. The obtained fraction was purified in the same manner as in Example 19, to obtain 150.39 mg of a purified product of compound I-23.

The properties of the compound I-23 were determined as follows.

MALDI-TOF-MS, UV, FT-IR and NMR were measured in the same manner as in Example 11.

The physicochemical properties of the compound I-23 are presented in the following.

Molecular formula: $C_{31}H_{37}NO_7$

MALDI-TOF-MS (m/z)

Found (M+H)$^+$: 536.2671.

Calculated: 536.2648 for $C_{31}H_{38}NO_7$.

UV λmax nm (ε): 215 (52,563), 261 (13,274), 300 (5,353)

IR νmax (NaCl) cm$^{-1}$: 3325, 2970, 2922, 2858, 1711, 1662, 1612, 1512, 1464, 1365, 1217, 1173, 1074

NMR

TABLE 20

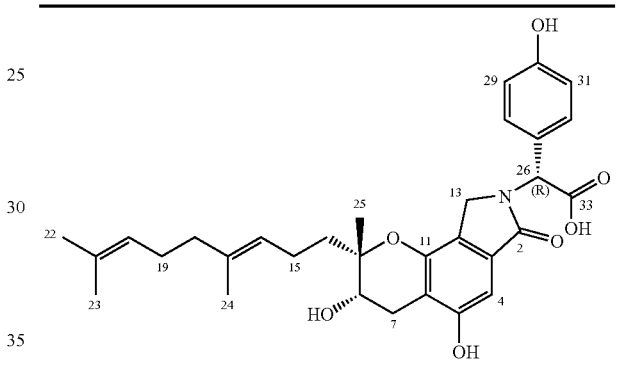

I-23: SMTP-44D

| No. | $\delta_C$ | $\delta_H$ |
|---|---|---|
| 2 | 169.00 | |
| 3 | 132.43 | |
| 4 | 100.69 | 6.80 (1H, s) |
| 5 | 157.05 | |
| 6 | 112.68 | |
| 7 | 27.56 | 2.97 (1H, dd, J = 5.5, 17.6) |
| | | 2.65 (1H, dd, J = 7.3, 17.6) |
| 8 | 67.52 | 3.87 (1H, dd, J = 5.5, 7.3) |
| 9 | 79.91 | |
| 11 | 149.79 | |
| 12 | 121.85 | |
| 13 | 45.61 | 4.48 (1H, d, J = 16.5) |
| | | 3.75 (1H, d, J = 16.5) |
| 14 | 38.28 | 1.65 (2H, m) |
| 15 | 22.17 | 2.11 (2H, m) |
| 16 | 125.20 | 5.09 (1H, m) |
| 17 | 135.48 | |
| 18 | 40.34 | 1.89 (2H, m) |
| 19 | 27.29 | 2.00 (2H, m) |
| 20 | 125.08 | 5.04 (1H, m) |
| 21 | 131.63 | |
| 22 | 25.78 | 1.61 (3H, m) |
| 23 | 17.68 | 1.49 (3H, s) |
| 24 | 15.84 | 1.54 (3H, s) |
| 25 | 18.65 | 1.26 (3H, s) |
| 26 | 58.28 | 6.04 (1H, s) |
| 27 | 126.73 | |
| 28, 32 | 131.00 | 7.27 (2H, m) |
| 29, 31 | 116.45 | 6.90 (2H, m) |
| 30 | 158.42 | |
| 33 | 172.18 | |

The chemical shift is relative to acetone-$d_6$ ($\delta_C$ 29.8 ppm [methyl carbon atom]; $\delta_H$ 2.04 ppm). The coupling constant (J) is given in Hz.

Example 28

Synthesis of Compound I-24 and Synthesis of Compound I-25

Preliminary culture was performed in the same manner as in Example 9.

Main culture was performed in the same manner as in Example 11, except that the organic amine compound added on day 4 of the main culture was changed to 50 mg of DL-3-hydroxyphenylglycine.

Crude purification was performed in the same manner as in Example 9, to obtain 230 mg of a dried solid product. MeOH was added to this dried solid product to obtain a 70 mg/ml solution, and the solution was subjected to a pretreatment in the same manner as in Example 9. Reverse phase HPLC was performed in the same manner as in Example 19, except for the developing conditions. For the developing solvent, methanol and 0.1% (vol/vol) of formic acid were used, and the methanol concentration was increased linearly from 75% to 90% over 30 minutes. A peak was fractionated at a retention time of 16 to 17 minutes (compound I-24), and another peak was fractionated at a retention time of 17.5 to 19 minutes (compound I-25). Each of the obtained fractions was purified in the same manner as in Example 19, to obtain 16.43 mg of a purified product of compound I-24 and 22.98 mg of a purified product of compound I-25.

The properties of the compound I-24 were determined as follows.

MALDI-TOF-MS, UV and FT-IR were measured in the same manner as in Example 9.

The physicochemical properties of the compound I-24 are presented in the following.

Molecular formula: $C_{31}H_{37}NO_7$

MALDI-TOF-MS (m/z)

Found $(M+H)^+$: 536.2716.

Calculated: 536.2648 for $C_{31}H_{38}NO_7$.

UV λmax nm (ε): 215 (47,531), 261 (11,348), 299 (3,212)

IR νmax (NaCl) $cm^{-1}$: 3294, 2970, 2926, 2858, 1703, 1662, 1605, 1464, 1367, 1219, 1161, 1076

The properties of the compound I-25 were determined as follows.

MALDI-TOF-MS, UV, FT-IR and NMR were measured in the same manner as in Example 11.

The physicochemical properties of the compound I-25 are presented in the following.

Molecular formula: $C_{31}H_{37}NO_7$

MALDI-TOF-MS (m/z)

Found $(M+H)^+$: 536.2723.

Calculated: 536.2648 for $C_{31}H_{38}NO_7$.

UV λmax nm (ε): 215 (57,915), 261 (13,703), 300 (3,747)

IR νmax (NaCl) $cm^{-1}$: 3309, 2974, 2924, 2864, 1707, 1662, 1603, 1465, 1365, 1224, 1163, 1076

NMR

TABLE 21

I-25: SMTP-45-II

| No. | $\delta_C$ | $\delta_H$ |
|---|---|---|
| 2 | 169.13 | |
| 3 | 132.23 | |
| 4 | 100.74 | 6.81 (1H, s) |
| 5 | 157.09 | |
| 6 | 112.81 | |
| 7 | 27.57 | 2.98 (1H, dd, J = 5.5, 17.6) |
|   |       | 2.65 (1H, dd, J = 7.3, 17.6) |
| 8 | 67.51 | 3.88 (1H, dd, J = 5.5, 7.3) |
| 9 | 79.95 | |
| 11 | 149.82 | |
| 12 | 121.87 | |
| 13 | 45.67 | 4.53 (1H, d, J = 16.5) |
|    |       | 3.78 (1H, d, J = 16.5) |
| 14 | 38.30 | 1.66 (2H, m) |
| 15 | 22.17 | 2.10 (2H, m) |
| 16 | 125.16 | 5.09 (1H, t, J = 7.0) |
| 17 | 135.53 | |
| 18 | 40.33 | 1.89 (2H, m) |
| 19 | 27.29 | 2.00 (2H, m) |
| 20 | 125.10 | 5.04 (1H, m) |
| 21 | 131.62 | |
| 22 | 25.78 | 1.66 (3H, s) |
| 23 | 17.68 | 1.54 (3H, s) |
| 24 | 15.85 | 1.48 (3H, s) |
| 25 | 18.69 | 1.26 (3H, s) |
| 26 | 58.71 | 6.08 (1H, s) |
| 27 | 137.43 | |
| 28 | 116.38 | 6.91 (1H, m) |
| 29 | 158.64 | |
| 30 | 116.25 | 6.86 (1H, dd, J = 2.2, 7.7) |
| 31 | 130.88 | 7.26 (1H, t, J = 7.7) |
| 32 | 120.59 | 6.89 (1H, d, J = 7.7) |
| 33 | 171.91 | |

The chemical shift is relative to acetone-$d_6$ ($\delta_C$ 29.8 ppm [methyl carbon atom]; $\delta_H$ 2.04 ppm). The coupling constant (J) is given in Hz.

Example 29

Synthesis of Compound I-26

Preliminary culture was performed in the same manner as in Example 9.

Main culture was performed in the same manner as in Example 11, except that the organic amine compound added on day 4 of the main culture was changed to L-tyrosine.

Crude purification was performed in the same manner as in Example 9, to obtain 310 mg of a dried solid product. MeOH was added to this dried solid product to obtain a 100 mg/ml solution, and the solution was subjected to a pretreatment in the same manner as in Example 9. Reverse phase HPLC was performed in the same manner as in Example 19, except for the developing conditions. For the developing solvent, methanol and 0.1% of formic acid were used, and the methanol concentration was increased linearly from 70% to 80% over 30 minutes. A peak was fractionated at a retention time of 21 to 23 minutes. The obtained fraction was purified in the same manner as in Example 19, to obtain 53.94 mg of a purified product of compound I-26.

The properties of the compound I-26 were determined as follows.

MALDI-TOF-MS, UV and FT-IR were measured in the same manner as in Example 9.

NMR was measured using an ALPHA600 (JEOL, Ltd.) under the conditions of $^1$H 600 MHz, $^{13}$C 150 MHz and 40° C. The sample used was a DMSO-$d_6$ solution of about 30 mg/ml.

The physicochemical properties of the compound I-26 are presented in the following.

Molecular formula: $C_{32}H_{39}NO_7$
MALDI-TOF-MS (m/z)
Found (M+H)$^+$: 550.4594.
Calculated: 550.2805 for $C_{32}H_{40}NO_7$.
UV λmax nm (ε): 215 (39,050), 261 (8,690), 297 (sh) (2,530)
IR νmax (NaCl) cm$^{-1}$: 3379, 2922, 2854, 1707, 1664, 1514, 1464, 1363, 1221, 1167, 1074
NMR

TABLE 22

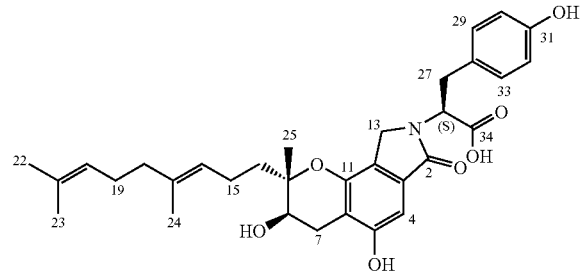

I-26: SMTP-14

| No. | $\delta_C$ | $\delta_H$ |
|---|---|---|
| 2 | 168.07 | |
| 3 | 130.79 | |
| 4 | 99.53 | 6.59 (1H, m) |
| 5 | 156.08 | |
| 6 | 111.58 | |
| 7 | 26.54 | 2.80 (1H, dd, J = 5.1, 17.7) |
| | | ~2.46 (1H, m) |
| 8 | 65.79 | 3.73 (1H, t, J = 5.7) |
| 9 | 78.73 | |

TABLE 22-continued

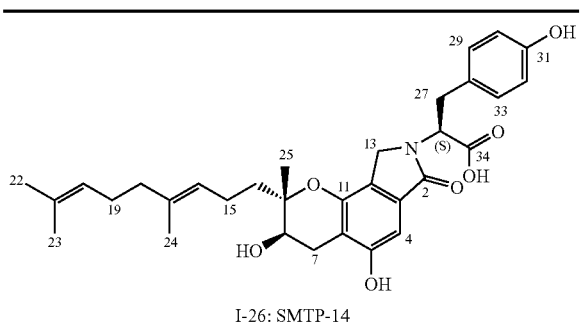

I-26: SMTP-14

| No. | $\delta_C$ | $\delta_H$ |
|---|---|---|
| 11 | 148.30 | |
| 12 | 119.53 | |
| 13 | 44.47 | 4.19 (1H, d, J = 16.8) |
| | | 4.13 (1H, d, J = 16.8) |
| 14 | 36.92 | 1.56 (2H, m) |
| 15 | 21.00 | 2.09 (2H, m) |
| 16 | 124.06 | 5.11 (1H, m) |
| 17 | 134.27 | |
| 18 | 39.04 | 1.92 (2H, m) |
| 19 | 26.10 | 2.00 (2H, m) |
| 20 | 124.00 | 5.05 (1H, m) |
| 21 | 130.52 | |
| 22 | 25.28 | 1.61 (3H, s) |
| 23 | 17.37 | 1.52 (3H, s) |
| 24 | 15.48 | 1.52 (3H, s) |
| 25 | 18.35 | 1.17 (3H, s) |
| 26 | 54.83 | 4.97 (1H, dd, J = 5.1, 11.1) |
| 27 | 33.75 | 3.22 (1H, dd, J = 4.8, 15.0) |
| | | 3.07 (1H, dd, J = 11.4, 14.4) |
| 28 | 127.42 | |
| 29, 33 | 129.18 | 6.99 (2H, d, J = 8.4) |
| 30, 32 | 115.04 | 6.60 (2H, d, J = 9.0) |
| 31 | 155.69 | |
| 34 | 172.03 | |

The chemical shift is relative to dimethyl-$d_6$-sulfoxide ($\delta_C$ 39.5 ppm [methyl carbon atom]; $\delta_H$ 2.49 ppm). The coupling constant (J) is given in Hz.

Example 30

For the various triprenyl phenol compounds obtained as described above, the performance was evaluated with regard to the thrombolytic activity as the activity of promoting the plasminogen (plg) activation by urokinase catalysis.

In addition, orniplabin (SMTP-7) was used in the Comparative Example. The respective compounds are as follows.

TABLE 23

| Compound No. | Amine added | Remarks |
|---|---|---|
| I-1 | p-Aminophenol | SMTP-18 |
| I-2 | p-aminobenzoic acid | SMTP-19 |
| I-3 | m-aminobenzoic acid | SMTP-20 |
| I-4 | o-Aminobenzoic acid | SMTP-21 |
| I-5 | 4-Aminosalicylic acid | SMTP-22 |
| I-6 | 4-Amino-3-hydroxybenzoic | SMTP-23 |
| I-7 | 3-Hydroxyanthranilic acid | SMTP-24 |
| I-8 | 3-Aminosalicylic acid | SMTP-25 |
| I-9 | 5-Aminosalicylic acid | SMTP-26 |
| I-10 | 3-Amino-4-hydroxybenzoic acid | SMTP-27 |
| I-11 | 5-Hydroxyanthranilic acid | SMTP-28 |
| I-16 | Adenine | SMTP-32 |
| I-17 | 5-Amino-2,3-dihydro-1,4-phthalazinedione | SMTP-36 |
| I-18 | 1-Amino-2-naphthol-4-sulfonic acid | SMTP-37 |
| I-19 | p-Sulfanilic acid | SMTP-42 |
| I-20 | L-phenylglycine | SMTP-43 |
| I-21 | D-phenylglycine | SMTP-43D |
| I-22 | L-4-hydroxy-phenylglycine | SMTP-44 |

TABLE 23-continued

| | | |
|---|---|---|
| I-23 | D-4-hydroxy-phenylglycine | SMTP-44D |
| I-24 | DL-3-hydroxy-phenylglycine | SMTP-45-I |
| I-25 | DL-3-hydroxy-phenylglycine | SMTP-45-II |
| I-26 | L-tyrosine | SMTP-14 |
| Orniplabin | Ornithine | Comparative Example |
| X-1 | Serine | Comparative Example |
| X-2 | Phenylalanine methyl ester | Comparative Example |

(p-Aminophenol)

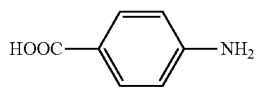

(p-Aminobenzoic acid)

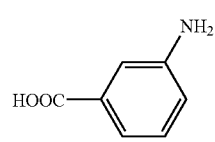

(m-Aminobenzoic acid)

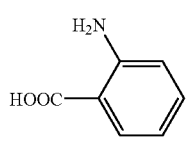

(o-Aminobenzoic acid)

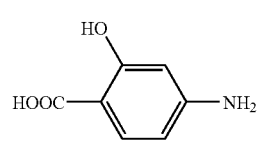

(4-Aminosalicylic acid)

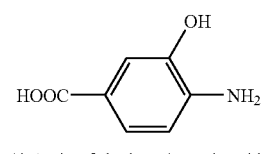

(4-Amino-3-hydroxybenzoic acid)

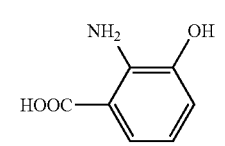

(3-Hydroxyanthranilic acid)

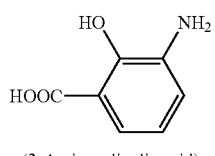

(3-Aminosalicylic acid)

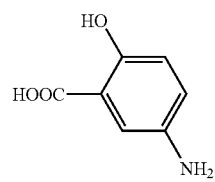

(5-Aminosalicylic acid)

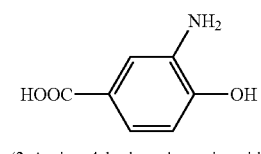

(3-Amino-4-hydroxybenzoic acid)

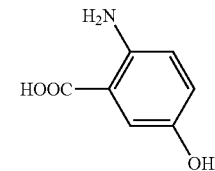

(5-Hydroxyanthranilic acid)

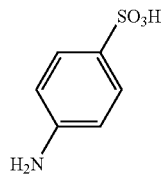

(p-Sulfanilic acid)

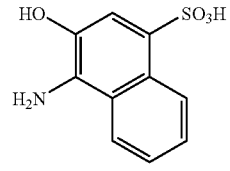

(1-Amino-2-naphthol-4-sulfonic acid)

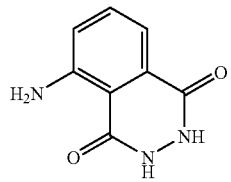

(5-Amino-2,3-dihydro-1,4-phthalazinedione)

TABLE 23-continued

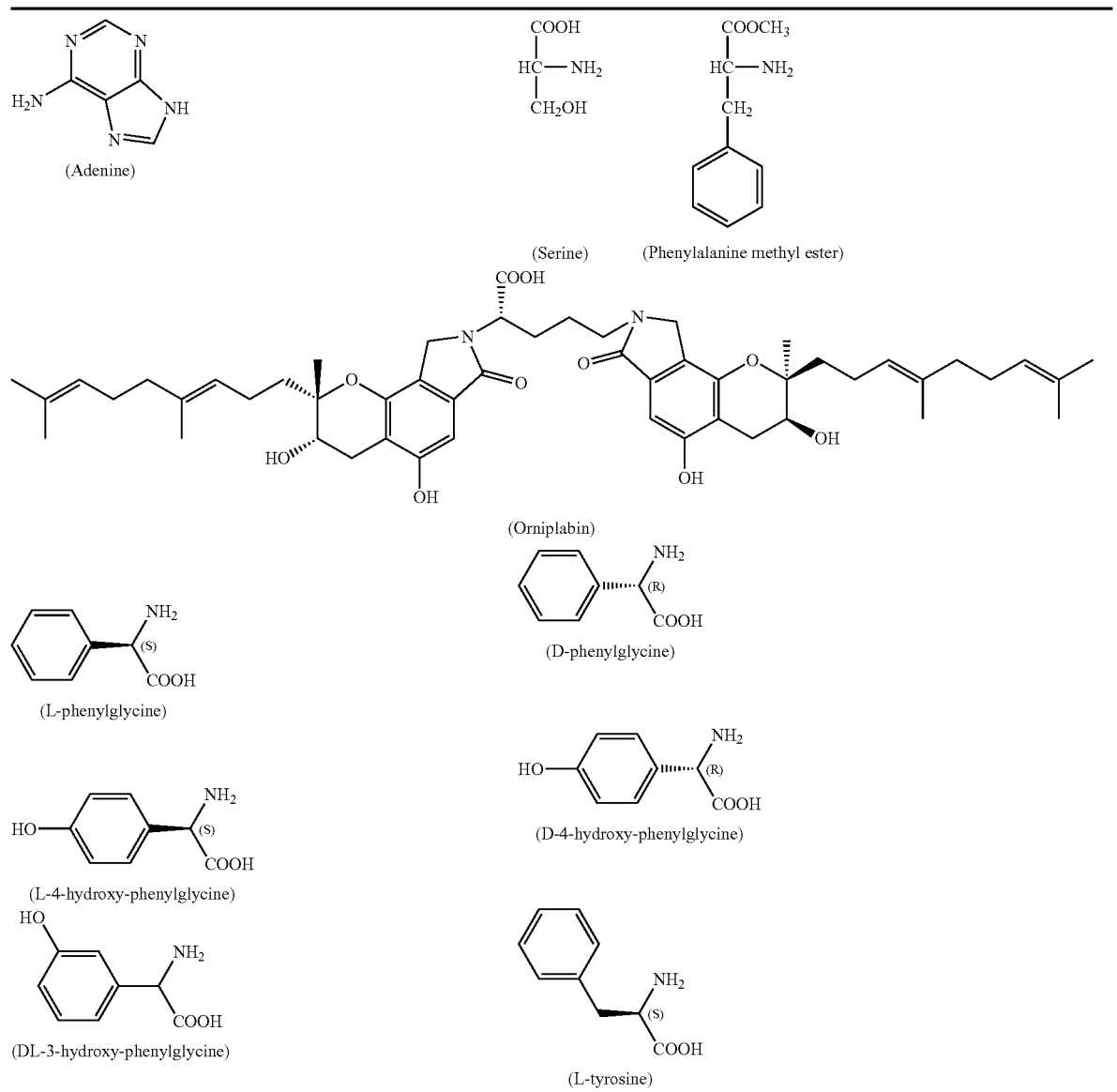

The property of plasmin of cutting the peptide bond of a synthetic chromogenic substrate VLK-pNA (Val-Leu-Lys-p-nitroanilide) to generate p-nitroaniline (pNA), was used to measure the yellow coloration of pNA which is absorbed at 405 nm, and thereby the plasminogen activation enhancing activity of a sample is measured. An MTP-500 type microplate reader (Corona Electric Co., Ltd.) was employed as the measuring device, and measurement was performed with a 96-well round bottom microplate.

The measurement was performed under the conditions of kinetic measurement at 37° C. with dual wavelength of 405 nm (activity) to 595 nm (background), for 60 times in every minute.

The purified samples were each made into a DMSO solution or an aqueous solution of sodium salt. This solution was diluted with TBS/T (50 mM Tris-HCl, 100 mM NaCl and 0.01% Tween80, pH 7.4) to provide a sample for measurement. To 15 µl of the sample, 35 µl each of the reaction liquid (adjusted with TBS/T such that the final concentrations were achieved at 0.1 mM VLK-pNA, 50 nM Glu-plg and 50 U/ml u-PA, respectively) was added to result in 50 µl/well, and measurement was performed in triplicate for each concentration.

Furthermore, as a blank, a reaction was performed using a reaction liquid not containing u-PA, and the value obtained therefrom was subtracted from the values obtained from the reactions described above. The absorbance was plotted against the square of time, and the slope was defined as the initial rate of reaction. A reaction solution not added with any triprenyl phenol compound was taken as the control and was compared with the samples, to determine the degree of activity of the respective compounds.

The term "concentration of 10-fold enhancing activity" indicates the concentration at which 10-fold enhancing activity is obtained in the case where the value obtained by using a reaction solution not containing any SMTP compound (control) is taken as 1. The term "maximum enhancing activity" indicates the concentration at which the enhancement of plasminogen activation by an SMTP compound reaches the maximum.

The results are presented in Table 24.

TABLE 24

| Compound | | Molecular weight | 10-Fold enhancing activity | | Maximum enhancing activity | | |
|---|---|---|---|---|---|---|---|
| | | | Concentration by weight (μg/ml) | Concentration by mole (μM) | Multiplication factor | Concentration by weight (μg/ml) | Concentration by mole (μM) |
| I-1 | SMTP-18 | 477 | 86 | 180 | 18 | 95 | 200 |
| I-2 | SMTP-19 | 505 | 42 | 83 | 126 | 81 | 160 |
| I-3 | SMTP-20 | 505 | 102 | 202 | 52 | 151 | 300 |
| I-4 | SMTP-21 | 505 | 67 | 133 | 51 | 101 | 200 |
| I-5 | SMTP-22 | 521 | 52 | 100 | 158 | 101 | 200 |
| I-6 | SMTP-23 | 521 | 68 | 131 | 65 | 151 | 290 |
| I-7 | SMTP-24 | 521 | 90 | 173 | 37 | 151 | 290 |
| I-8 | SMTP-25 | 521 | 37 | 71 | 91 | 52 | 100 |
| I-9 | SMTP-26 | 521 | NA* | NA* | 8 | 63 | 120 |
| I-10 | SMTP-27 | 521 | 98 | 188 | 43 | 151 | 290 |
| I-11 | SMTP-28 | 521 | 66 | 127 | 65 | 101 | 200 |
| I-16 | SMTP-32 | 503 | NA* | NA* | 5 | 200 | 398 |
| I-17 | SMTP-36 | 545 | 52 | 95 | 45 | 95 | 174 |
| I-18 | SMTP-37 | 607 | 50 | 82 | 60 | 150 | 247 |
| I-19 | SMTP-42 | 541 | 74 | 137 | 60 | 163 | 300 |
| I-20 | SMTP-43 | 519 | 46 | 89 | 402 | 150 | 289 |
| I-21 | SMTP-43D | 519 | 54 | 104 | 44 | 150 | 289 |
| I-22 | SMTP-44 | 535 | 113 | 211 | 18 | 160 | 299 |
| I-23 | SMTP-44D | 535 | 177 | 331 | 22 | 215 | 402 |
| I-24 | SMTP-45-I | 535 | 74 | 138 | 112 | 107 | 200 |
| I-25 | SMTP-45-II | 535 | 123 | 230 | 29 | 215 | 402 |
| I-26 | SMTP-14 | 549 | 42 | 77 | 76 | 110 | 200 |
| Orniplabin | | 868 | 56 | 65 | 100 | 78 | 90 |
| X-1 | | 473 | NA** | NA** | 1 | NA** | NA** |
| X-2 | | 547 | NA** | NA** | 1 | NA** | NA** |

*Not measurable because of low solubility or low activity.
**Not applicable because the enhancing activity is absent.

The triprenyl phenol compounds of I-1 to I-11 and I-16 to I-19 were compounds obtained by adding aminophenol or aminobenzoic acid, adenine, adenosine, aminodihydrophthalazinedione, aminonaphtholsulfonic acid, sulfanilic acid or a derivative thereof. In these compounds, an aromatic group having a carboxyl group or a hydroxyl group as a substituent is directly connected to the triprenyl phenol skeleton.

The triprenyl phenol compounds of I-20 to I-26 are compounds obtained by adding phenylglycine or tyrosine. In these compounds, there are one or two methyl groups disposed between the aromatic ring and the triprenyl phenol skeleton.

As shown in Table 24, all of these compounds were recognized to have plasminogen activation enhancing activity, thus being useful as a thrombolytic agent like orniplabin. Further, since these compounds are all low molecular weight compounds, an absorbability superior to that of orniplabin is expected.

In particular, compounds I-2, I-5, I-8, I-20, I-24 and I-26 exhibited equivalent or higher plasminogen activation enhancing activity compared to orniplabin, and thus it was suggested that these compounds could be used as thrombolytic agents which are better than orniplabin, from the viewpoint of absorbability.

Therefore, it is obvious that the compounds of the present Examples can be used as effective thrombolytic agents with good absorbability and high activity.

The invention claimed is:

1. A triprenyl phenol compound of the following formula (II) or (III):

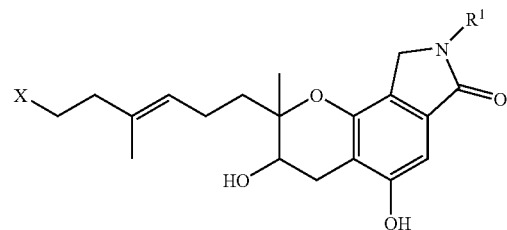

(II)

wherein, in Formula (II), $R^1$ is an aromatic group having as a substituent or as a part of a substituent at least one group selected from the group consisting of a carboxyl group, a hydroxyl group, a sulfonic acid group and a secondary amino group,

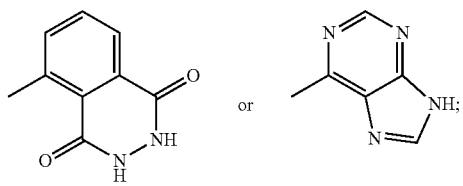

X is —CHY—C(CH$_3$)$_2$Z; and Y and Z are respectively —H or —OH, or together form a single bond;

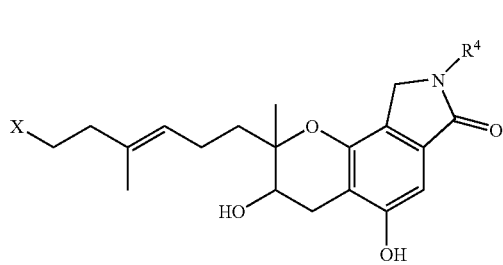

(III)

wherein, in Formula (III), $R^4$ is an aromatic amino acid residue of the following formula (III-1) (provided that tyrosine and phenylalanine residue are excluded); X is —CHY—C(CH$_3$)$_2$Z; and Y and Z are respectively —H or —OH, or together form a single bond,

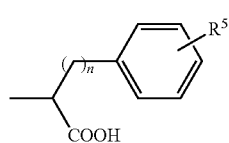

(III-1)

wherein $R^5$ is a substituent which may be present or absent and which is selected from the group consisting of a hydroxyl group, a carboxyl group and an alkyl group having 1 to 5 carbon atoms, and wherein n represents an integer of 0 or 1.

2. The triprenyl phenol compound of claim 1, wherein the triprenyl phenol compound is of Formula (II).

3. The triprenyl phenol compound of claim 2, wherein the aromatic group is of the following formula (II-1):

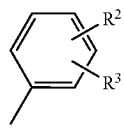

(II-1)

wherein $R^2$ and $R^3$ respectively are a carboxyl group, a hydroxyl group or a sulfonic acid group, or are joined together to form a cyclic group containing a secondary amino group.

4. The triprenyl phenol compound of claim 2, wherein the aromatic group is selected from the following:

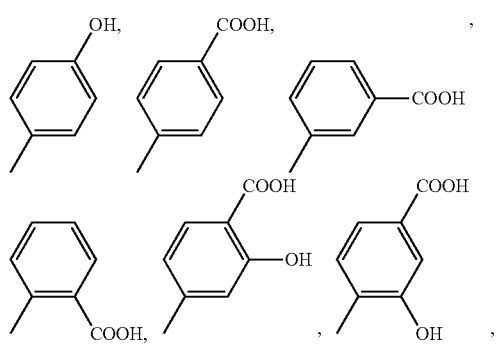

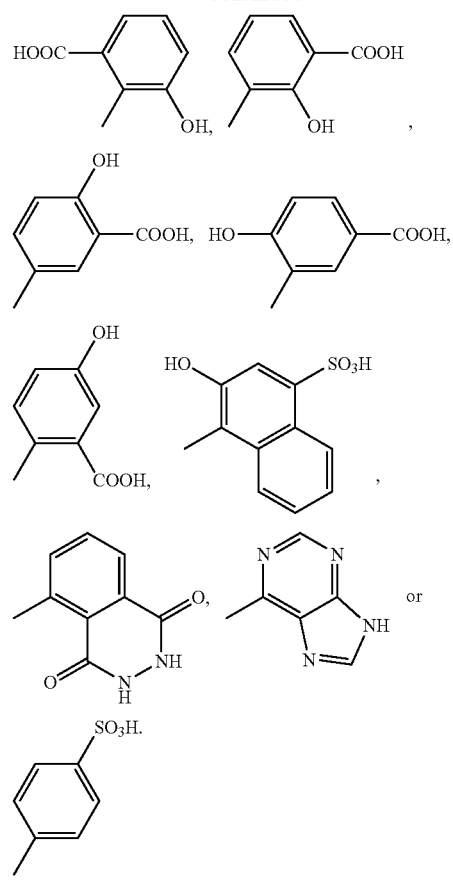

5. The triprenyl phenol compound of claim 1, wherein the triprenyl phenol compound is of Formula (III).

6. The triprenyl phenol compound of claim 5, wherein $R^4$ in Formula (III) is selected from the following:

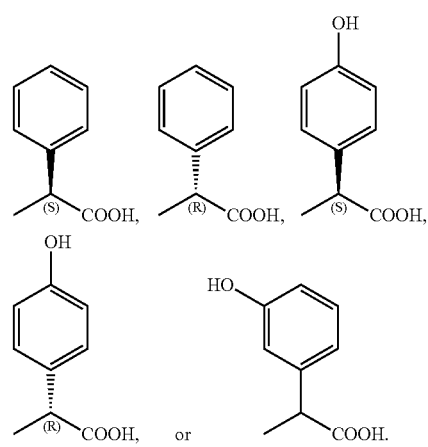

7. A thrombolysis enhancer comprising the triprenyl phenol compound of claim 1 as an active ingredient, and an excipient or a solvent.

* * * * *